United States Patent
Svendsen et al.

(10) Patent No.: US 10,927,106 B2
(45) Date of Patent: Feb. 23, 2021

(54) BENZOTHIAZOLE DERIVATIVES AS DYRK1 INHIBITORS

(71) Applicant: PHARMASUM THERAPEUTICS AS, Kvaløysletta (NO)

(72) Inventors: John Sigurd Svendsen, Kvaløysletta (NO); Wenche Stensen, Kvaløysletta (NO); Roderick Alan Porter, Ashwell (GB)

(73) Assignee: PHARMASUM THERAPEUTICS AS, Kvaløysletta (NO)

( * ) Notice: Subject to any disclaimer, the term of this patent is extended or adjusted under 35 U.S.C. 154(b) by 0 days.

(21) Appl. No.: 16/341,630

(22) PCT Filed: Oct. 12, 2017

(86) PCT No.: PCT/EP2017/076118
§ 371 (c)(1),
(2) Date: Apr. 12, 2019

(87) PCT Pub. No.: WO2018/069468
PCT Pub. Date: Apr. 19, 2018

(65) Prior Publication Data
US 2019/0375742 A1  Dec. 12, 2019

(30) Foreign Application Priority Data

Oct. 12, 2017 (GB) ..................................... 1617339

(51) Int. Cl.
*C07D 417/04* (2006.01)
*C07D 513/04* (2006.01)
*C07D 417/14* (2006.01)

(52) U.S. Cl.
CPC ......... *C07D 417/04* (2013.01); *C07D 417/14* (2013.01); *C07D 513/04* (2013.01)

(58) Field of Classification Search
CPC ... C07D 417/04; C07D 513/04; C07D 417/14
USPC ..................................................... 546/270.1
See application file for complete search history.

(56) References Cited

U.S. PATENT DOCUMENTS

| 6,130,217 | A | 10/2000 | Arnold et al. |
| 6,136,831 | A | 10/2000 | Aotsuka et al. |
| 7,495,106 | B1 | 2/2009 | Tan et al. |
| 7,847,101 | B2 * | 12/2010 | Zhang ................. A61K 31/428 544/135 |
| 8,163,928 | B2 * | 4/2012 | Gravenfors ........... C07B 59/002 546/270.1 |
| 2007/0258887 | A1 | 11/2007 | Tamagnan et al. |
| 2009/0197862 | A1 | 8/2009 | Steinig et al. |
| 2011/0171739 | A1 | 7/2011 | Kemp et al. |

FOREIGN PATENT DOCUMENTS

| CN | 1623992 A | 6/2005 |
| DE | 9930926 C | 7/1955 |
| EP | 2873668 A1 | 5/2015 |
| GB | 2311010 A | 9/1997 |
| JP | 2011/079774 A | 4/2011 |
| JP | 2014/111558 A | 6/2014 |
| JP | 2014/208695 A | 11/2014 |
| KR | 101292478 B1 | 7/2013 |
| WO | 94/022846 A1 | 10/1994 |
| WO | 98/046594 A1 | 10/1998 |
| WO | 2002/030895 A1 | 4/2002 |
| WO | 2007/009236 A1 | 1/2007 |
| WO | 2007/010085 A2 | 1/2007 |
| WO | 2007/064773 A2 | 6/2007 |
| WO | 2007/086800 A1 | 8/2007 |
| WO | 2008/121407 A1 | 10/2008 |
| WO | 2008/137816 A2 | 11/2008 |
| WO | 2009/027475 A1 | 3/2009 |
| WO | 2009/066152 A2 | 5/2009 |
| WO | 2010/022121 A1 | 2/2010 |
| WO | 2010/034982 A1 | 4/2010 |
| WO | 2011/043404 A1 | 4/2011 |
| WO | 2011/103441 A1 | 8/2011 |
| WO | 2012/110959 A1 | 8/2012 |
| WO | 2013/018928 A1 | 2/2013 |
| WO | 2013/066729 A1 | 5/2013 |
| WO | 2013/180194 A1 | 12/2013 |
| WO | 2014/037340 A1 | 3/2014 |
| WO | 2014/119494 A1 | 8/2014 |
| WO | 2014/119670 A1 | 8/2014 |
| WO | 2014/119672 A1 | 8/2014 |
| WO | 2014/119674 A1 | 8/2014 |
| WO | 2014/119679 A1 | 8/2014 |
| WO | 2014/119699 A1 | 8/2014 |
| WO | 2014/123206 A1 | 8/2014 |
| WO | 2014/125651 A1 | 8/2014 |

(Continued)

OTHER PUBLICATIONS

Lee et al., Asian Journal of Chemistry (2014), 26(13), 3937-3940.*
Liu et al., Yaoxue Xuebao (2013), 48(1), 83-88.*
Swahn et al., Bioorganic & Medicinal Chemistry Letters (2010), 20(6), 1976-1980.*
Saleh Bahashwan et al., "Androgen Receptor Antagonists and Anti-Prostate Cancer Activities of Some Newly Synthesized Substituted Fused Pyrazolo-, Triazolo- and Thiazolo-Pyrimidine Derivatives", International Journal of Molecular Sciences, vol. 15, No. 11, Nov. 24, 2014, pp. 21587-21602.
Rothweiler Ulli et al., "Luciferin and derivatives as a DYRK selective scaffold for the design of protein kinase inhibitors", European Journal of Medicinal Chemistry, Editions Scientifique Elsevier, Paris, FR, vol. 94, Feb. 25, 2015, pp. 140-148.

(Continued)

*Primary Examiner* — Niloofar Rahmani
(74) *Attorney, Agent, or Firm* — Fox Rothschild LLP

(57) ABSTRACT

The present invention relates to compounds of Formula (I), which are DYRK1A and/or DYRK1B inhibitors, and their use in the treatment of neurodegenerative disorders such as Alzheimer's disease (AD) and Parkinson's disease (PD), metabolic disorders such as Metabolic Syndrome or diabetes mellitus, and cancer.

15 Claims, 7 Drawing Sheets

(56) References Cited

FOREIGN PATENT DOCUMENTS

Figure 1:
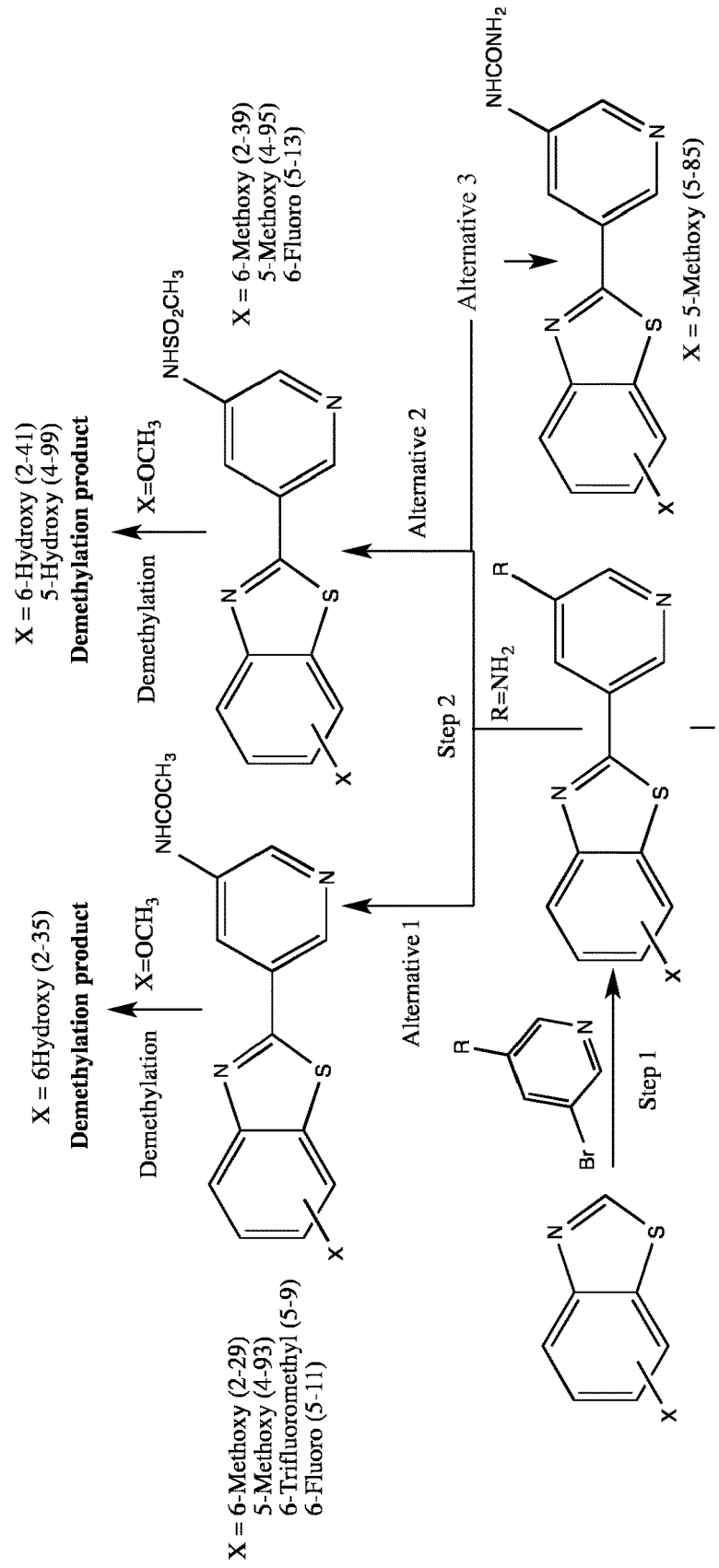

| WO | 2015/071180 A1 | 5/2015 |
| WO | 2015/118026 A1 | 8/2015 |
| WO | 2016/033460 A1 | 3/2016 |
| WO | 0322746 B1 | 3/2016 |

OTHER PUBLICATIONS

Smith et al., "Recent Advances in the Design, Synthesis, and Biological Evaluation of Selective DYRK1A Inhibitors: A New Avenue for a Disease Modifying Treatment of Alzheimer's?", ACS Chem. Neurosci. (2012) 3, 857-72.

Im and Chung, "Dyrk1A phosphorylates parkin at Ser-131 and negatively regulates its ubiquitin E3 ligase activity", J. Neurochem. (2015) 134, 756-68.

Shen et al., "Inhibition of DYRK1A and GSK3B induces human b-cell proliferation", Nat. Commun. (2015) 6, Article No. 8372.

Kassis et al., "Synthesis and biological evaluation of new 3-(6hydroxyindol-2-yl)-5-(Phenyl) pyridine or pyrazine V-Shaped molecules as kinase inhibitors and cytotoxic agents", Eur. J. Med. Chem. (2011) 46, 5416-34.

Hisano et al., "Synthesis of Benzoxazoles, Benzothiazoles and Benzimidazoles and Evaluation of Their Antifungal, Insecticidal and Herbicidal Activities", Chemical & Pharmaceutical Bulletin, 1982, 30(8), 2996-3004.

Hisano et al., "Synthesis of Organosulfur Compounds. VIII. Cyclization Products from the Modified Willgerodt-Kindler Reaction", Chemical & Pharmaceutical Bulletin, 1973, 21(3), 511-517.

Hisano et al., "Studies on Organosulfur Compounds. IX. Selective Cyclization to Benzothiazole by the Reaction between 4-Picoline and meta-Substituted Anilines under the Modified Willgerodt-Kindler Reaction", Yakugaku Zasshi, 1973, 93(10), 1356-1363.

Anderson et al., "Pyrido[2,3-d] pyrimidines: Discovery and preliminary Sar of a novel series of DYRK1B and DYRK1A inhibitors", Bioorganic & Medicinal Chemistry Letters, 23 (2013), 6610-6615.

Shavaleev et al., "Modulating the Near-Infrared Luminescence of Neodymium and Ytterbium Complexes with Tridentate Ligands Based on Benzoxazole-Substituted 8-Hydroxyquinolines", Inorganic Chemistry, 2009, 48(7), 2908-2918.

Nguyen et al., "Nitro-Methyl Redox Coupling: Efficient Approach to 2-Hetarylbenzothiazoles from 2-Halonitroarene, Methylhetarene, and Elemental Sulfur", Organic Letters, 2013, 15(16), 4218-4221.

Siddappa et al, "One-pot approach for the synthesis of 2-aryl benzothiazoles via a two-component coupling of gem-dibromomethylarenes and o-aminothiophenols", Tetrahedron Letters, 2011, 52(42), 5474-5477.

Bochatay et al., "Mechanistic Exploration of the Palladium-catalyzed Process for the Synthesis of Benzoxazoles and Benzothiazoles", Journal of Organic Chemistry, 2013, 78(4), 1471-1477.

Lim et al., "Microwave-Assisted Synthesis of Benzximidazoles, Benzoxazoles, and Benzothiazoles from Resin-Bound Esters", Journal or Combinatorial Chemistry, 2008, 10(4), 501-503.

Liu et al., "Synthesis and antitumor activity of 5-substituted-2-(pyridyl)benzothiazole compounds", Yaoxue Xuebao, 2013, 48(1), 83-88.

Volchkov et al., "Fluorescence Study of the Relaxation Process in Excited Fletarylthiazole Cations", Journal of Fluoresence, 2000, 10(2), 161-165.

Gromov et al, "Reactions of quinazolinium salts with quaternary heterocyclic salts yielding 3-hetarylquinolines", Russian Chemical Bulletin, 1998, 47(6), 1179-1185.

Lee et al., "Conversion of Thioamide to Benzothiazole with Oxidizing Agents", Asian Journal of Chemistry, 2014, 26(13), 3937-3940.

Tsuchiya et al., "Effects of Benzimidazoles on Mouse and Rat Limb Bud Cells in Culture", Toxicology Letters, 1987, 38 (1-2), 97-102.

Hisano et al., "Selective Cyclization in the Modified Willgerodt-Kindler Reaction", Organic Preparations and Procedures International, 1972, 4(3), 105-111.

Tong et al., "A simple approach to benzothiazoles from 2-chloronitrobenzene, elemental sulfur, and aliphatic amine under solvent-free and catalyst-free conditions", Tetrahedron Letters, 2014, 55(40), 5499-5503.

Rezazadeh et al., "Synthesis of substituted 2-heteroarylbenzazol-5-ol derivatives as potential ligands for estrogen receptors", Tetrahedron, 2013, 69(30), 6076-6082.

Swahn et al., "Synthesis and evaluation of 2-pyridylbenzothiazole, 2-pyridylbenzoxazole and 2-pyridylbenzofuran derivatives as 11C-Pet imaging agents for b-amyloid plaques", Bioorganic & Medicinal Chemistry Letters, 2010, 20(6), 1976-1980.

Kamal et al., "Synthesis and study of benzothiazole conjugates in the control of cell proliferation by modulating Ras/MEK/ERK-dependent pathway in MCF-7 cells", Bioorganic & Medicinal Chemistry Letters, 2013, 23(20), 5733-5739.

Hilal et al, "A QSAR study for 2-(4-aminophenyl)benzothiazoles: using DFT optimisation of geometry of molecules", Molecular Simulation, 2011, 37(1), 62-71.

Bertini et al., "Synthesis of heterocycle-based analogs of resveratrol and their antitumor and vasorelaxing properties", Bioorganic & Medicinal Chemistry Letters, 2010, 18(18), 6715-6724.

Cole et al., "Specific estrogen sulfotransferase (SULT1E1) substrates and molecular imaging probe candidates", Proceedings of the National Academy of Sciences USA, 2010, 107(14), 6222-6227.

Serdons et al., "11C-labelled PIB analogues as potential tracer agents for in vivo imaging of amyloid b in Alzheimer's disease", European Journal of Medicinal Chemistry, 2009, 44(4), 1415-1426.

Huang et al., "Searching for New Cures for Tuberculosis: Design, Synthesis, and Biological Evaluation of 2-Methylbenzothiazoles", Journal of Medicinal Chemistry, 2009, 52(21), 6757-6767.

Lee et aL., "Chemometric Studies on Brain-uptake of PET Agents via VolSurf Analysis", Bulletin of the Korean Chemical Society, 2008, 29(1), 61-68.

Lee et aL., "Synthesis and evaluation of stilbenylbenzoxazole and stilbenylbenzothiazole derivatives for detecting b-amyloid fibrils", Bioorganic & Medicinal Chemistry Letters, 2008, 18(4), 1534-1537.

Kim et al., "3D-QSAR of PET Agents for Imaging ?-Amyloid in Alzheimer's Disease", Bulletin of the Korean Chemical Society, 2007, 28(7), 1231-1234.

Henriksen et al., "Metabolically Stabilized Benzothiazoles for Imaging of Amyloid Plaques", Journal of Medicinal Chemistry, 2007, 50(6), 1087-1089.

Arasappan et al., "5-Benzothiazole substituted pyrimidine derivatives as HCV replication (replicase) inhibitors", Bioorganic & Medicinal Chemistry Letters, 2012, 22(9), 3229-3234.

Fu et al- "Dual Cell activations of electron-deficient heteroarenes: palladium-catalyzed oxidative cross coupling of thiazoles with azine N-oxides", Tetrahedron, 2013, 69(22), 4436-4444.

Park et al., "Synthesis of Benzothiazoles through Copper-Catalyzed One-Pot Three-Component Reactions with Use of Sodium Hydrosulfide as a Sulfur Surrogate", European Journal of Organic Chemistry, 2012, 2012(10), 1984-1993.

Yoshida et al., "Chemiluminescent properties of some luminol-related compounds—Part 3", Dyes and Pigments, 2000, 47(3), 239-245.

* cited by examiner

BENZOTHIAZOLE DERIVATIVES AS DYRK1 INHIBITORS

The present invention relates to novel DYRK1A (dual-specificity tyrosine-(Y)-phosphorylation-regulated kinase 1A) inhibitors and their use in the treatment of neurodegenerative disorders, in particular Alzheimer's disease (AD) and Parkinson's disease (PD), and in the treatment of diabetes mellitus (DM).

AD is the most common form of dementia and no treatment exists which can stop, let alone reverse, progression of the disease. The memory and other mental health implications of AD are well known but the disease is also a killer; the average life expectancy after diagnosis is about seven years as bodily functions are gradually lost. This is a common degenerative condition, generally affecting people over sixty five, and it is recognised as placing a significant burden on careers, health services and society in general as life expectancy continues to rise and the numbers of people affected by AD increases.

AD is characterised by loss of neurons and synapses in the cerebral cortex and some subcortical regions. Amyloid plaques and neurofibrillary tangles are observed in the brains of those with AD.

Amyloid plaques form on the outside of neurons and are made up of peptides of thirty nine to forty three amino acids called beta-amyloid ($A_\beta$), these are fragments of amyloid precursor protein, a trans-membrane protein that penetrates the neuron's membrane and is critical to neuron growth, survival and repair.

Neurofibrillary tangles are aggregates of the microtubule-associated protein tau (MAPT, also known as tau) which have become hyperphosphorylated and accumulated in the neurons. In healthy neurons, tau serves to stabilise the microtubules of the neuronal cytoskeleton. Certain conditions are characterised by an increase in these tau tangles and this group of conditions are referred to as tauopathies. Tauopathies include PD (discussed in further detail below), Pick's disease and progressive supranuclear palsy, as well as AD. While an increase in amyloid plaques may be seen decades before the onset of symptoms of AD, the symptoms of AD are often observed just after a noticeable increase in tau protein is seen.

While it is generally accepted that these two proteins have a role in AD, the pathological mechanism and the causal events are not known. It had been postulated that the formation of amyloid plaques caused AD but therapies which successfully reduced plaque formation did not give significant improvement in symptoms such as dementia.

Current medication for AD shows limited benefit. Acetylcholinesterase inhibitors such as tacrine and donepezil are used to decrease the rate at which acetylcholine is broken down in the brain, in order to counteract the reduction in cholinergic neuron activity which is associated with AD. These therapies have shown some benefit, at least in mild to moderate AD. The NMDA receptor antagonist memantine has been shown to have very modest efficacy in the treatment of moderate to severe AD.

Amyloid plaques are a focus of AD research and numerous compounds have been proposed as binders of these plaques and of use in imaging techniques, for example in U.S. Pat. No. 8,163,928. It has also been speculated that binding to plaques may offer therapeutic potential but this has not been substantiated.

PD is a long term disorder of the central nervous system that mainly affects the motor system. The motor symptoms of the disease result from the death of cells in the *Substantia nigra*. This results in not enough dopamine in these areas. The reason for this cell death involves the build-up of proteins into Lewy bodies in the neurons.

There is no cure for PD. Initial treatment is typically with the levodopa, with dopamine agonists being used once levodopa becomes less effective. As the disease progresses and neurons continue to be lost, these medications become less effective while at the same time they produce a complication marked by involuntary writhing movements.

In 2013 PD was present in fifty three million people and resulted in about 103,000 deaths globally. PD typically occurs in people over the age of sixty, of which about one percent are affected. The average life expectancy following diagnosis is between seven and fourteen years.

Parkin is the first known gene to cause autosomal recessive familial PD. Homozygous mutations in parkin are responsible for early-onset autosomal recessive juvenile Parkinsonism, and its heterozygous mutations are responsible for late-onset sporadic PD. Loss of parkin function would result in the impairment of substrate degradation and be expected to induce dopaminergic cell death.

Diabetes mellitus (DM), is a group of metabolic diseases in which there are high blood sugar levels over a prolonged period. Symptoms of high blood sugar include frequent urination, increased thirst, and increased hunger. If left untreated, diabetes can cause many complications. Acute complications can include diabetic ketoacidosis, nonketotic hyperosmolar coma, or death. Serious long-term complications include heart disease, stroke, chronic kidney failure, foot ulcers, and damage to the eyes.

There are two main types of long term DM, namely type 1 DM and type 2 DM. Type 1 DM results from the pancreas's failure to produce enough insulin. By contrast type 2 DM begins with insulin resistance, a condition in which cells fail to respond to insulin properly. As the disease progresses a lack of insulin may also develop. The primary cause of type 2 DM is excessive body weight and not enough exercise. Type 1 DM must be managed with insulin injections, whilst type 2 DM may be treated with medications with or without insulin. All forms of DM are associated with a decrease in pancreatic β-cell mass. Patients with type 1 DM have a dramatic reduction in β-cell mass, leading to insulin insufficiency and hyperglycaemia. In type 2 DM, insulin resistance causes a compensatory expansion of β-cells and increased plasma insulin levels. However, frank DM develops over time as β-cell mass decreases. Notably, a majority of genes identified in genome-wide association studies of type 2 DM are regulators of β-cell mass and/or β-cell function. Finally, insufficient β-cell mass and insulin secretion also cause mature onset diabetes of the young and gestational diabetes. Therefore, approaches to increase functional pancreatic β-cell mass may lead to improved therapeutic options for treatment of many forms of diabetes.

As of 2015, an estimated 415 million people had diabetes worldwide, with type 2 DM making up about 90% of the cases. This represents 8.3% of the adult population, with equal rates in both women and men. As of 2014, trends suggested the rate would continue to rise. Diabetes at least doubles a person's risk of early death. From 2012 to 2015, approximately 1.5 to 5.0 million deaths each year resulted from diabetes. The global economic cost of diabetes in 2014 was estimated to be US$612 billion.

β-cell replication maintains functional β-cell mass in adult mice and humans, and several studies have shown proliferation in primary β-cells following a variety of genetic or pharmacologic interventions. While a large number of hormones, small molecules, growth factors and nutrients are capable of inducing primary rodent β-cell replication, only harmine has been demonstrated to stimulate an increase in proliferation of adult primary human β-cells.

There is undoubtedly an urgent need for further therapeutic options in the treatment of AD, PD and other neurodegenerative conditions, whether to slow or halt disease progression, improve symptoms or delay onset; the tools available to the clinician at present are completely inadequate. Similarly, there is a need for further therapeutic options in the treatment of DM in order to provide patients with more adequate blood glucose control so that long term complications can be reduced.

The present inventors have developed compounds which act as inhibitors of DYRK1A, a kinase thought to be important in neonates and in the early stages of life. DYRK1A is a kinase whose over-activity has recently been implicated in the pathogenesis of AD and other tauopathies, PD and DM. The DYRK1A gene is copied in triplicate in patients that have Down Syndrome (DS), who are themselves more likely to develop AD; between 50 and 70% of DS patients develop dementia by the age of sixty and nearly all DS patients have amyloid plaques and neurofibrillary tangles above the age of thirty. DYRK1A is thought to play a role in the development of AD, both by increasing amyloid plaque formation and increasing intracellular tau protein tangles. Studies have identified DYRK1A as the priming kinase of multiple phosphorylation of the tau protein and studies of the brains of patients with AD showed increased expression of DYRK1A in neurons affected by tau tangles (Smith et al., *ACS Chem. Neurosci.* (2012) 3, pp 857-72). DYRK1A has also been found to directly phosphorylate the protein encoded by parkin at Ser-131 and consequently it inhibits the neuroprotective function of the gene (Im & Chung, *J. Neurochem.* (2015) 134, pp 756-68). Furthermore, the inhibition of DYRK1A has been found to stimulate the proliferation of rodent and human β-cells in vitro and in vivo (Shen et al., *Nat. Commun.* (2015) 6, Article Number: 8372)

There is a further DYRK kinase, DYRK1B (also referred to as Minibrain-Related Kinase—MIRK), which is highly related to DYRK1A, sharing 85% identity at the amino acid level. Many of the inhibitors of DYRK1A which have been developed by the present inventors are also inhibitors of DYRK1B and in certain scenarios, such dual activity is preferred. Compounds of the invention will inhibit one or both of DYRK1A and DYRK1B. DYRK1B is implicated in cancer and metabolic disorders including metabolic syndrome (as well as in neurodegenerative disorders), thus opening up further therapeutic applications of the compounds of the invention.

Smith et al. (supra) provide a review of selective DYRK1A inhibitors, both naturally derived and synthetic. However, while confirming the significance of DYRK1A as a target, they conclude that in vivo data for even the most promising inhibitors suggests that their potential therapeutic use may still be partially limited by broad specificity and/or undesirable side-effects.

Kassis and co-workers (*Eur. J. Med. Chem.* (2011) 46, pp 5416-34) (one of the groups discussed in the Smith review) describe DYRK1A and cyclin-dependent kinase (CDK) inhibitors in the form of 3-(hydroxyindol-2-yl)-5-(phenyl) pyradines and pyrazines. The inhibition of CDK as well as DYRK1A by these compounds could lead to adverse drug reactions.

Harmine is a potent inhibitor of DYRK1A but is hallucinogenic.

Rothweiler et al. in *Eur. J. Med. Chem.* (2015) 94, pp 140-8 describe compounds based on D-luciferin as protein kinase inhibitors, in particular as inhibitors of DYRK1A. However the observed inhibitory effects are still modest in a therapeutic context.

Thus there is a need for alternative and/or improved inhibitors of DYRK1A. In particular there is a need for highly selective kinase inhibitors so that off-target effect on other kinases are reduced. The present inventors have identified a new class of DYRK1A inhibitor which possess some or all of these advantageous features. In preferred embodiments these molecules will also act as inhibitors of DYRK1B. Molecules as defined herein which inhibit DYRK1B but are only modestly active or inactive against DYRK1A are also encompassed by the present invention.

According to one aspect, the present invention provides a compound of Formula (I),

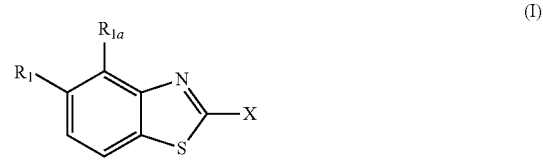

wherein $R_1$ is selected from the group consisting of fluorine, an $OR_2$ group, a $CONHR_3$ group, $CH_2C(O)NHR_3$ and —C≡$CR_2$, preferably $OR_2$;

$R_2$ is hydrogen or a $C_{1-3}$ alkyl group, preferably H or $CH_3$;

$R_3$ is hydrogen or a $C_{1-3}$ alkyl group, preferably H; and $R_{1a}$ is H;

or $R_1$ and $R_{1a}$ together form a 5- or 6-membered unsubstituted ring, optionally containing a heteroatom selected from N, O or S, preferably wherein $R_1$ and $R_{1a}$ together represent $OCH_2CH_2$, with the O atom in the $R_1$ position;

X is a five- or six-membered aromatic heterocyclic group, containing one or two nitrogen atoms in the ring, and which is substituted with a first substituent $R_4$, and optionally, a second substituent $R_5$, wherein $R_4$ and $R_5$, if present, are attached to a carbon atom in the heterocyclic group;

$R_4$ and $R_5$, which may be the same or different, are each a group represented by Formula (II),

wherein the covalent bonds V—W, W—Y, and Y—Z are single, double or triple bonds, preferably single bonds;

V represents C, N or F, if V is C, the C may be substituted by O, OH, F, $F_2$ or $F_3$, and if V is N, the N may be substituted by a $C_{1-3}$ alkyl group;

W represents C, N, O, S, or is absent, if W is C, the C may be substituted by O, OH, $CH_3$, F, $F_2$ or $F_3$, if W is N, the N may be substituted by a $C_{1-3}$ alkyl group, preferably methyl, and if W is S, the S is substituted by O or $(O)_2$, preferably $(O)_2$;

or

W represents a 5- or 6-membered carbocyclic group, or a 5- or 6-membered heterocyclic group having at least one ring N atom and optionally also a further heteroatom in the ring selected from N, O and S, preferably N and O, wherein W may optionally be substituted by one or two halogen atoms;

Y represents C, N, O, S or is absent, if Y is C, the C may be substituted by O, OH, $CH_3$, F, $F_2$ or $F_3$, if Y is S, the S is substituted by O or $(O)_2$, preferably $(O)_2$;

or

Y represents a 5- or 6-membered carbocyclic group, or a 5- or 6-membered heterocyclic group containing 1 or 2 nitrogen atoms in the ring, and optionally substituted by one or two groups, which may be the same or different, and are selected from OH, $NH_2$, $NH(CO)CH_3$, $CH_2NH_2$, $CH_2NHC_{1-3}$ alkyl and $CH_2N(C_{1-3}$ alkyl$)_2$, preferably $CH_2NHCH_3$ or $CH_2N(C_{1-3}$alkyl$)_2$, most preferably $CH_2N(CH_3)_2$;

Z represents C, N, O or is absent, if Z is C, the C may be substituted by O, OH, $NH_2$, or $CH_3$, if Z is N, the N may be substituted by $C(O)C_{1-4}$alkyl, $S(O)_2C_{1-4}$alkyl or $CHR^{4a}COOH$, wherein $R^{4a}$ is selected from H, $CH_3$, $CH(CH_3)_2$, $CH_2OH$ or $CH(OH)CH_3$, if Z is O, the O may be substituted by $C_{1-4}$alkyl;

wherein if W, Y and Z are absent from $R_4$ and $R_5$ is also absent, V is not unsubstituted N or C;

wherein $R_5$, if present, comprises six or fewer non-hydrogen atoms;

or a pharmaceutically acceptable salt, hydrate, solvate or tautomer thereof, but excluding the following compounds:

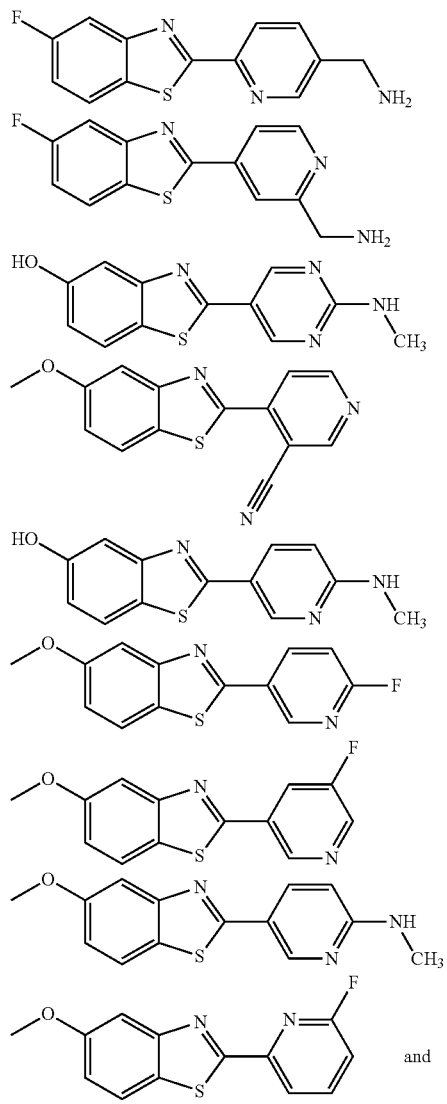

and

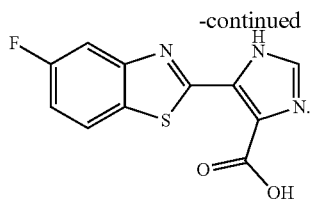

X is preferably a six-membered aromatic heterocyclic group, most preferably pyridine.

More preferably, X is selected from:

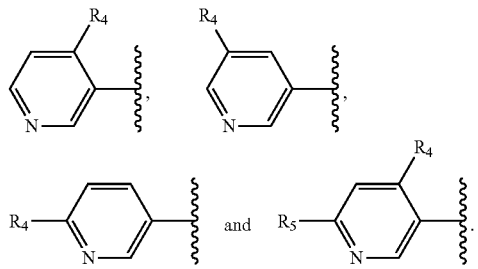

Most preferably X is selected from:

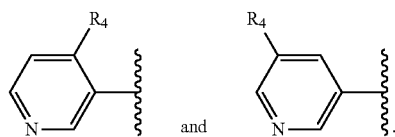

Preferably, V represents unsubstituted C or N, more preferably unsubstituted N.

Preferably, W represents unsubstituted C, unsubstituted N, C substituted by O, S substituted by $(O)_2$, a 6-membered carbocyclic group, or a 6-membered heterocyclic group having one ring N atom, more preferably unsubstituted N, C substituted by O or a 6-membered heterocyclic group having one ring N atom, and most preferably C substituted by O.

Preferably, Y represents unsubstituted N or C or C substituted by O or $CH_3$, more preferably unsubstituted C or C substituted by O.

The term "5- or 6-membered carbocyclic group" refers to any 5- or 6-membered cyclic group containing only carbon atoms, which may be saturated or unsaturated, and which may be aromatic. Examples of 5-membered carbocyclic groups include cyclopentyl. Examples of 6-membered carbocyclic groups include cyclohexyl, cyclohexenyl and phenyl.

Preferably, the 5- or 6-membered carbocyclic group is cyclohexyl or phenyl. More preferably, when Y represents a 5- or 6-membered carbocyclic group, Y represents phenyl, and/or when W represents a 5- or 6-membered carbocyclic group, W represents cyclohexyl.

The term "5- or 6-membered heterocyclic group" refers to any 5- or 6-membered heterocyclic group, which may be saturated or unsaturated, and which may be aromatic.

When W represents a 5- or 6-membered heterocyclic group, the heterocyclic group must contain at least one ring N atom, and may also contain a further N, O or S atom. Examples of suitable heterocyclic groups include piperidine, piperazine, morpholine, pyridine, pyrimidine, pyrazine, pyridazine, imidazole, thiazole, pyrrole, oxazole, isoxazole, pyrazole, and isothiazole. When W represents a 5- or 6-membered heterocyclic group, the ring may be substituted by one or two halogen atoms in addition to the Y substituent. If present, it is preferred that only one halogen substituent is present.

When Y represents a 5- or 6-membered heterocyclic group, the heterocyclic group must contain 1 or 2 N atoms. Examples of suitable heterocyclic groups include piperidine, piperazine, pyridine, pyrimidine, pyrazine, pyridazine, imidazole, pyrrole, and pyrazole.

Preferably the 5- or 6-membered heterocyclic group is piperidine or piperazine, most preferably piperidine.

The term "alkyl" refers to straight and branched saturated aliphatic hydrocarbon chains. $C_{1-4}$alkyl groups include methyl (Me), ethyl (Et), propyl (e.g., n-propyl and isopropyl) and butyl (e.g., n-butyl, isobutyl, t-butyl).

Preferred compounds are represent by Formula (III):

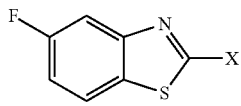

(III)

in which X is as defined above and the relevant disclaimers apply.

Further preferred compounds are represented by Formula (IV):

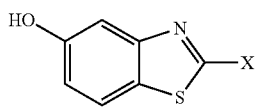

(IV)

in which X is as defined above and the relevant disclaimers apply.

Further preferred compounds are represented by Formula (V):

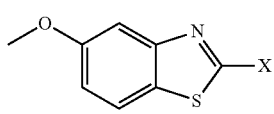

(V)

in which X is as defined above and the relevant disclaimers apply.

Preferred X, $R_4$ and $R_5$ moieties are also preferred in the context of each of formulae (III), (IV) and (V).

Reference hereinafter to compounds of the invention, to compounds of formulae (I), (II), (III), (IV) and (V) and to preferred embodiments thereof include salts, hydrates, solvates and tautomers of depicted structures.

Figure 3:
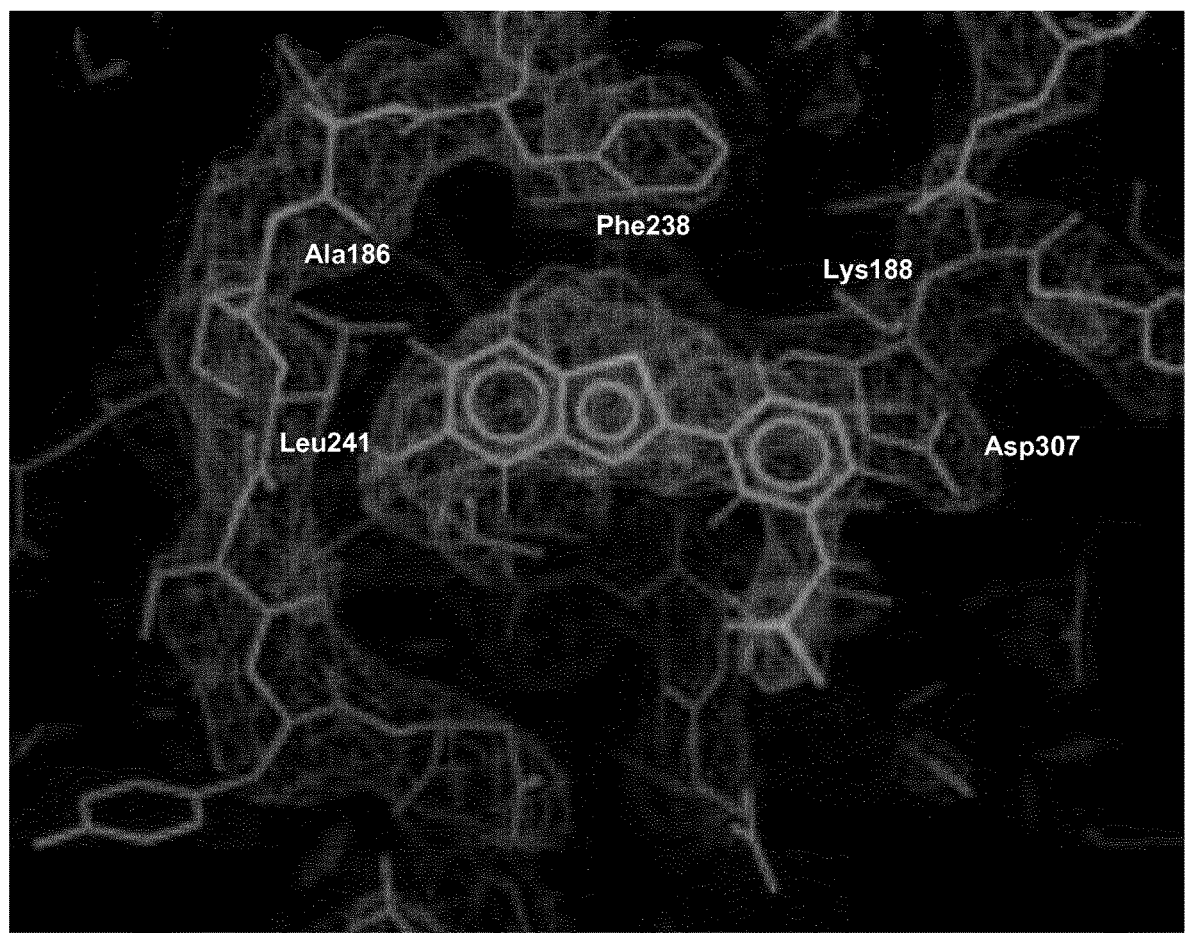

Some compounds of the present invention have been found to not only inhibit the protein kinase DYRK1A, but to inhibit DYRK1A specifically, i.e. to inhibit DYRK1A to a greater extent compared to (most) other protein kinases. This is shown in Table 6. This observation is highly surprising, as compounds (especially small molecules such as those claimed) often show a higher level of cross-reactivity. Without wishing to be bound by theory, this is thought to be due to the combination of the benzothiazole and the heterocyclic ring of X creating a tight fit within the DYRK1A ATP binding pocket (as shown in FIG. 3 and as discussed in Example D). It is well understood in the art that a cross-reactive therapeutic agent is more likely to cause adverse drug reactions when administered and for this reason it is important that the compounds such as those claimed as specific for their target, in this case inhibiting DYRK1A.

Many compounds of the invention are specific inhibitors of DYRK1A and DYRK1B, i.e. they inhibit these two kinases to a greater extent than other or most other kinases. Some compounds of the invention will be more effective inhibitors of DYRK1B than of DYRK1A.

Reference above to V, W, Y or Z being substituted (or unsubstituted) means covalently attached atoms or groups other than V, W, Y or Z themselves. Thus, if the group represented by formula (II) is —N(CH$_2$CH$_3$)CH$_2$CH$_2$CH$_3$, then V is N substituted by $C_2$ alkyl and W, Y and Z are all carbon, unsubstituted but with hydrogen atoms completing standard valencies.

Each of V, W, Y and Z may be substituted by multiple substituents, as valencies allow. Thus, a reference to "C substituted by CH$_3$" encompasses carbon substituted by 1 CH$_3$ group (e.g. —CH$_2$CH$_3$, —CH(CH$_3$)— etc.), 2 CH$_3$ groups (—CH(CH$_3$)$_2$, —C(CH$_3$)$_2$—, etc.), or 3 CH$_3$ groups (e.g. —C(CH$_3$)$_3$).

When not all valencies of an atom defined in the formulae of the present invention are explicitly accounted for, each spare valency may either be filled by a hydrogen atom or form an additional bond to an atom that it is already covalently linked to (i.e. to form double or triple bonds).

All of the atoms defined in the formulae of the present invention are stable isotopes, i.e. the compounds are not made up of any radioactive isotopes.

Preferably $R_4$ has no more than 14 non-hydrogen atoms, more preferably no more than 11 non-hydrogen atoms, even more preferably between 4 and 10 non-hydrogen atoms, and most preferably 4 or 5 non-hydrogen atoms.

In a further aspect the present invention provides a compound of formula (I) excluding the compounds identified above as excluded for use in therapy. The present invention further provides a compound of formula (I) as defined herein for use in the treatment or prevention of a neurodegenerative disorder. The treatment or prevention of a neurodegenerative disorder may be by inhibiting formation of neurofibrillary (tau) tangles and/or by inhibiting DYRK1A. In a further aspect the present invention provides a compound of formula (I) as defined herein for use in the treatment or prevention of a metabolic disorder, preferably Metabolic Syndrome or DM. In these specific uses and in the methods defined below, the uses and methods may extend to the compounds identified as excluded from the invention in the context of the compounds per se.

In a further aspect the present invention provides a compound of formula (I) as defined herein for use in the treatment or prevention of cancer, including cancer of the breast, esophagus, gastrointestinal tract, gastrointestinal stromal tumors, pancreas, prostate, biliary tract, bladder, basal cell carcinoma, medulloblastoma, rhabdomyosarcoma, glioma, small-cell lung cancer, oral squamous cell carcinoma, melanoma, colorectal cancer, non-small cell lung cancer, osteosarcoma, glioblastoma, chronic lymphacytic leukemia, chronic myeloid leukemia, multiple myeloma, acute myeloid leukemia, ovarian cancer, meningioma, and liver cancer.

The treatment or prevention of a neurodegenerative disorder may be by inhibiting DYRK1A phosphorylation of tau or the protein encoded by parkin.

In a further aspect, the present invention provides a method of treating or preventing a neurodegenerative disorder in a subject comprising administering to said subject a therapeutically effective amount of a compound of formula (I) as defined herein.

In a further aspect, the present invention provides a method of inhibiting formation of neurofibrillary (tau) tangles or inhibiting phosphorylation of tau or the protein encoded by parkin in a subject, the method comprising administering to said subject a therapeutically effective amount of a compound of formula (I) as defined herein.

In a further aspect, the present invention provides a method of treating or preventing a metabolic disorder in a subject comprising administering to said subject a therapeutically effective amount of a compound of formula (I) as defined herein.

In a further aspect, the present invention provides a method of treating or preventing cancer in a subject comprising administering to said subject a therapeutically effective amount of a compound of formula (I) as defined herein.

In a further aspect, the present invention provides the use of a compound of formula (I) in the manufacture of a medicament. The present invention provides the use of a compound of formula (I) in the manufacture of a medicament for the treatment or the prevention of a neurodegenerative disorder. Alternatively, the present invention provides the use of a compound of formula (I) in the manufacture of a medicament for the treatment or the prevention of a metabolic disorder or cancer.

Preferably, the linear $R_4$ and $R_5$ substituents comprise acetamido, ether, sulfonamide, nitrile and/or haloalkyl groups.

Preferably, $R_4$ is selected from the moieties depicted in Table 1 below:

TABLE 1

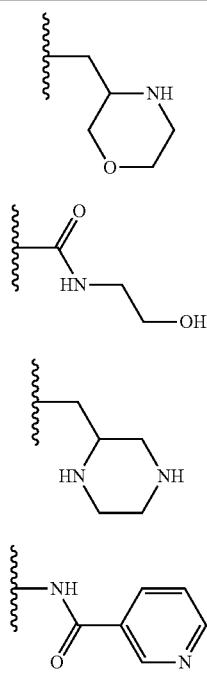

TABLE 1-continued

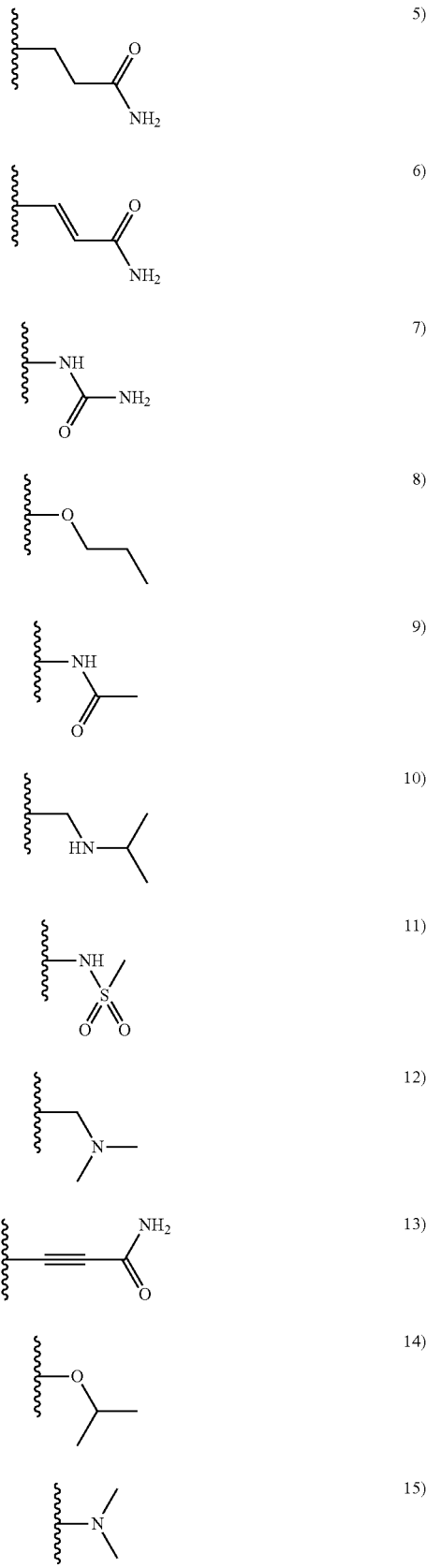

TABLE 1-continued
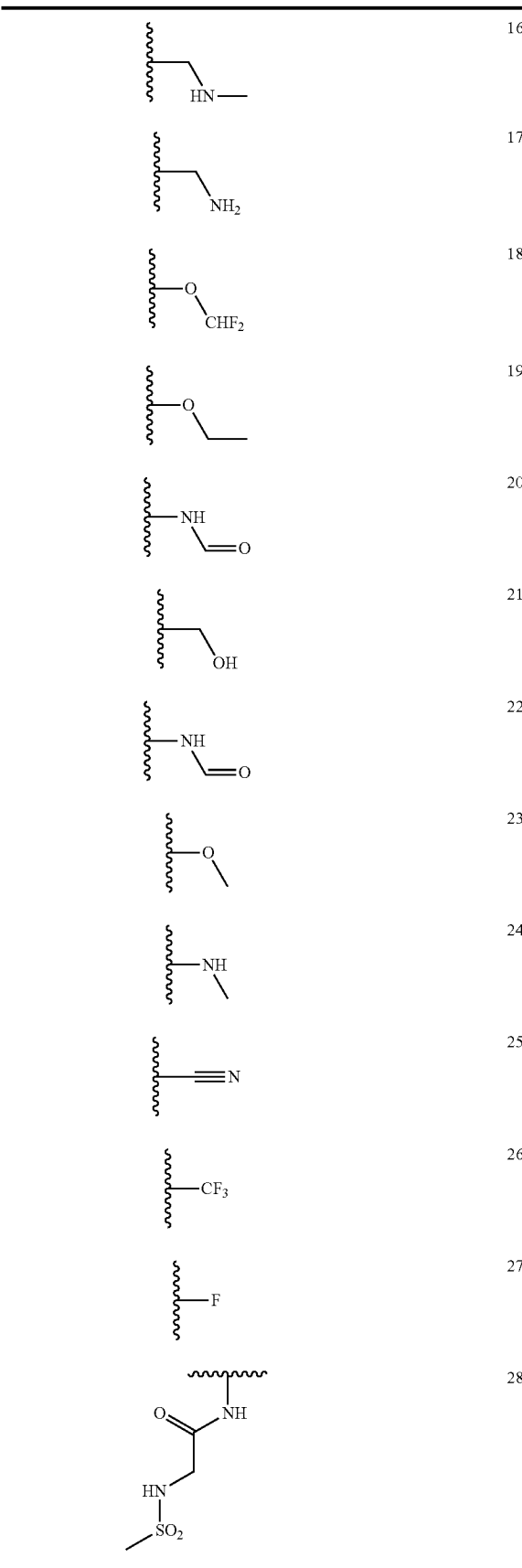
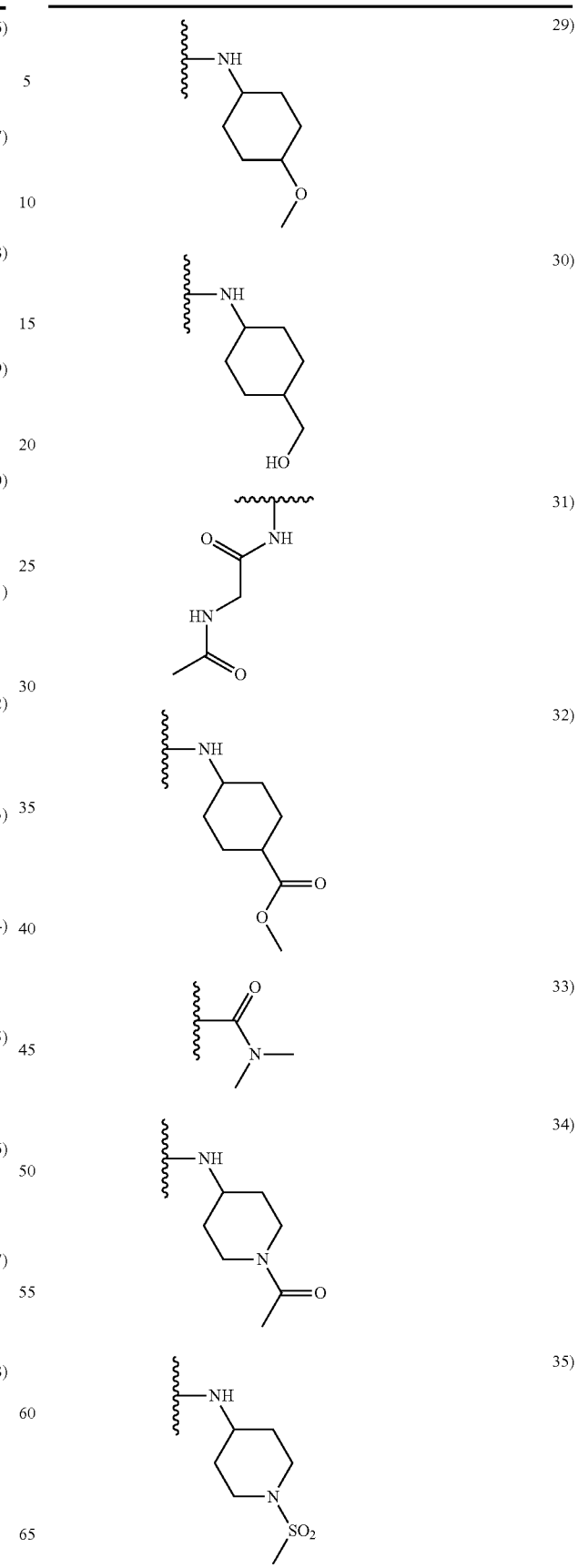

TABLE 1-continued
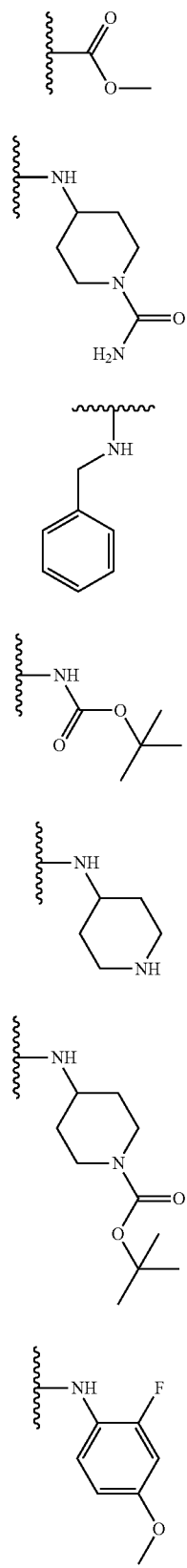
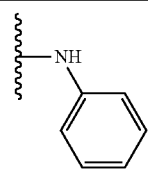
A preferred group of $R_4$ moieties are optionally alkyl substituted methylamino groups, i.e. $CH_2NH_2$, $CH_2NHC_{1-3}$ alkyl, preferably $CH_2NHCH_3$ or $CH_2N(C_{1-3}alkyl)_2$, preferably CH$_2$N(CH$_3$)$_2$. Such groups are also preferred examples of R$_5$ and R$_4$ and R$_5$ may both be selected from such groups.

In R$_5$, Y and Z are preferably absent, optionally W, Y and Z are absent. R$_5$ is preferably selected from the groups shown in Table 1 above, but excluding substituents 1, 3 and 4 as these substituents are too large for the second substituent. R$_5$ is conveniently selected from the group consisting of F, CH$_3$, NH$_2$, CH$_2$OH, N(CH$_3$)$_2$, CH$_2$NH$_2$, CH$_2$NHCH$_2$ and CH$_2$N(CH$_3$)$_2$, more preferably CH$_3$. In some preferred embodiments, R$_5$ is absent altogether.

Compounds of the invention may form stereoisomers and all such isomers are within the scope of the present invention.

Some suitable arrangements regarding the position of the heteroatom and the position of R$_4$, or of R$_4$ and R$_5$, are presented below in Table 2.

TABLE 2

1) 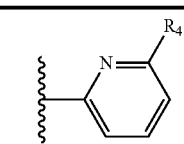

2) 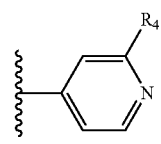

3) 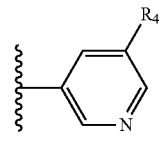

4) 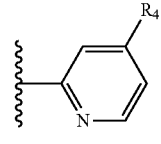

5) 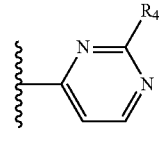

6) 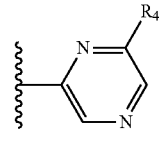

7) 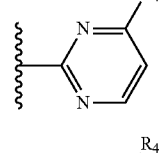

8) 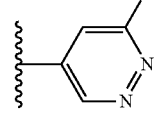

TABLE 2-continued

9) 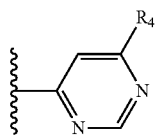

10) 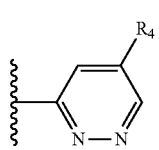

11) 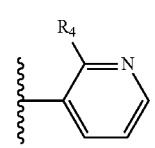

12) 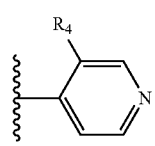

13) 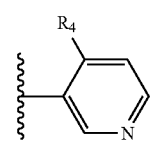

14) 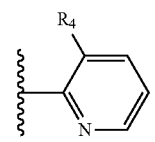

15) 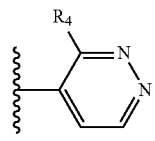

16) 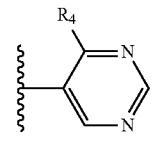

17) 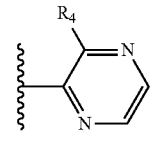

18) 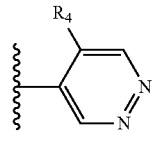

19) 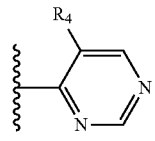

TABLE 2-continued
| | |
|---|---|
| 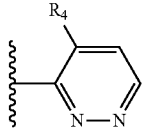 | 20) |
| 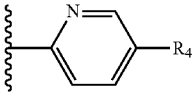 | 21) |
| 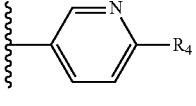 | 22) |
| 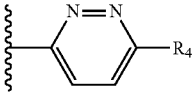 | 23) |
| 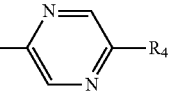 | 24) |
| 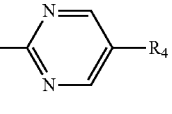 | 25) |
| 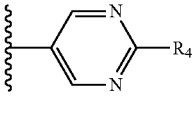 | 26) |
| 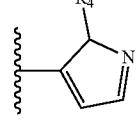 | 27) |
| 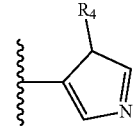 | 28) |
| 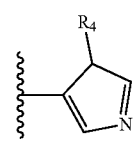 | 29) |
| 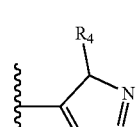 | 30) |
| 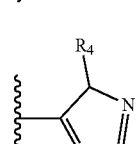 | 31) |
TABLE 2-continued
| | |
|---|---|
| 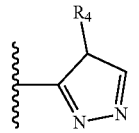 | 32) |
| 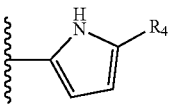 | 33) |
| 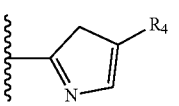 | 34) |
| 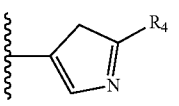 | 35) |
| 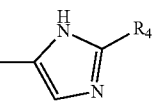 | 36) |
| 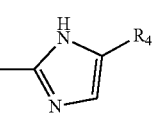 | 37) |
| 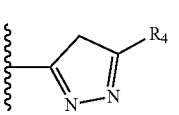 | 38) |
| 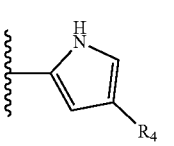 | 39) |
| 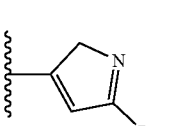 | 40) |
| 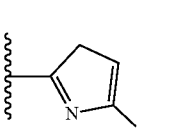 | 41) |
| 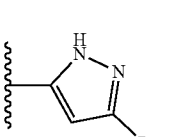 | 42) |
| 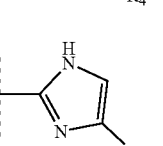 | 43) |

TABLE 2-continued
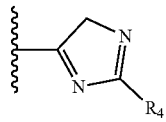 44)
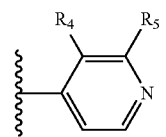 45)
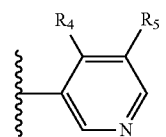 46)
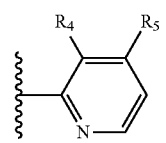 47)
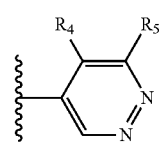 48)
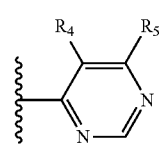 49)
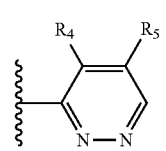 50)
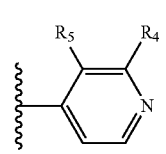 51)
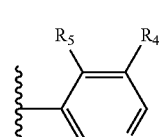 52)
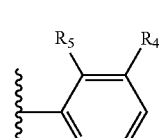 53)
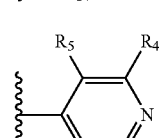 54)
TABLE 2-continued
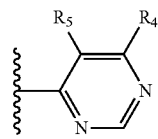 55)
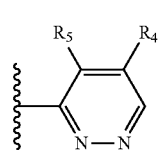 56)
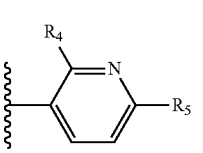 57)
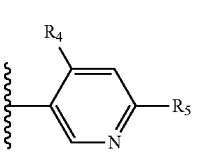 58)
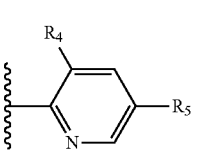 59)
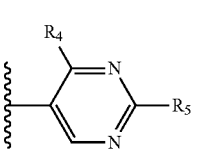 60)
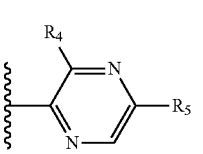 61)
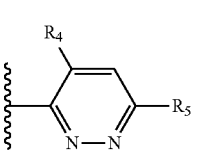 62)
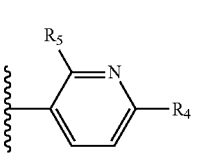 63)
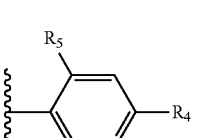 64)
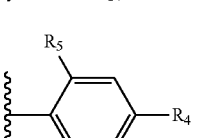 65)

TABLE 2-continued
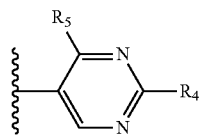 66)
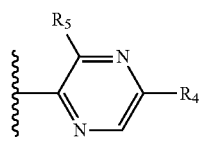 67)
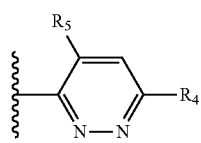 68)
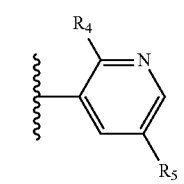 69)
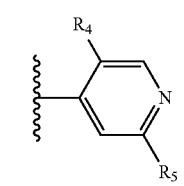 70)
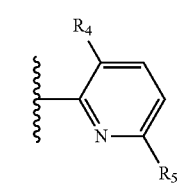 71)
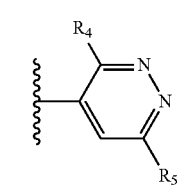 72)
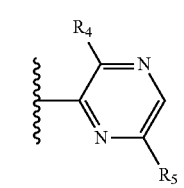 73)
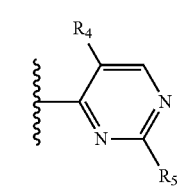 74)
TABLE 2-continued
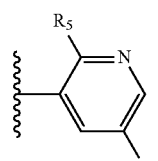 75)
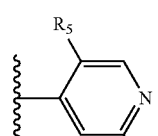 76)
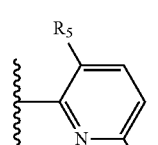 77)
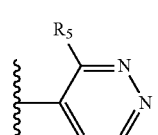 78)
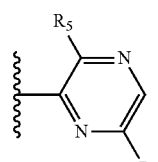 79)
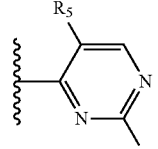 80)
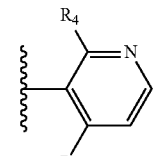 81)
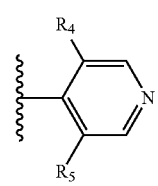 82)

TABLE 2-continued
| | |
|---|---|
| 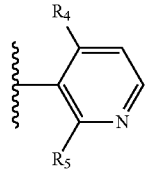 | 83) |
| 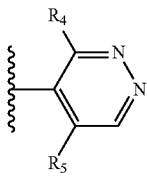 | 84) |
| 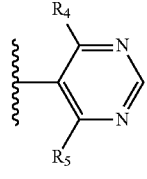 | 85) |
| 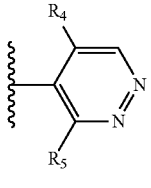 | 86) |
| 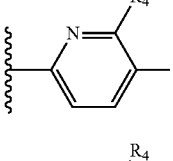 | 87) |
| 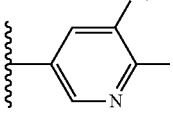 | 88) |
| 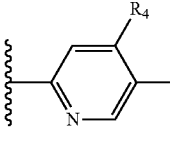 | 89) |
| 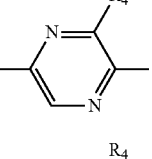 | 90) |
| 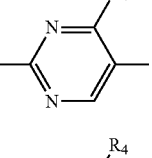 | 91) |
| 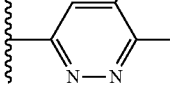 | 92) |
TABLE 2-continued
| | |
|---|---|
| 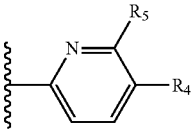 | 93) |
| 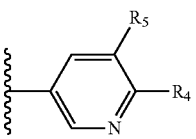 | 94) |
| 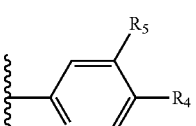 | 95) |
| 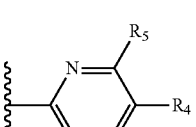 | 96) |
| 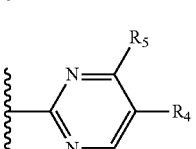 | 97) |
| 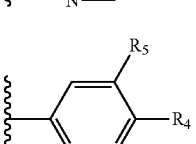 | 98) |
| 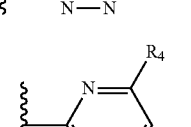 | 99) |
| 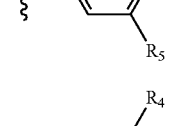 | 100) |
| 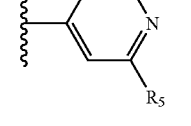 | 101) |
| 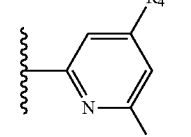 | 102) |

TABLE 2-continued
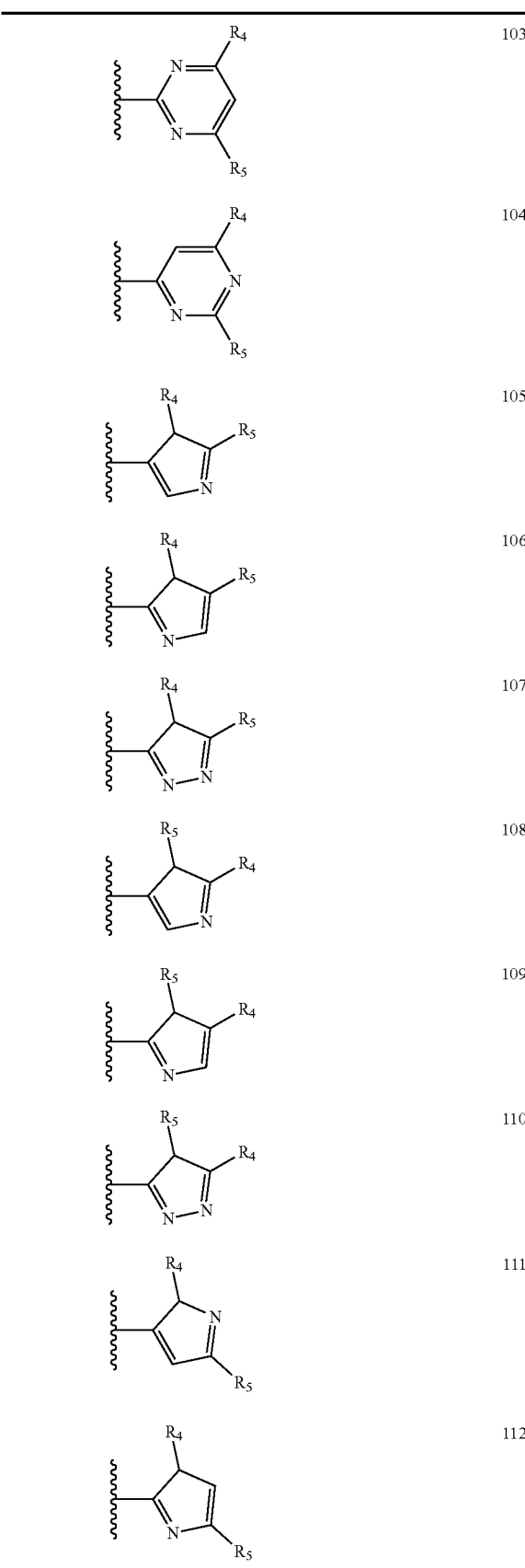
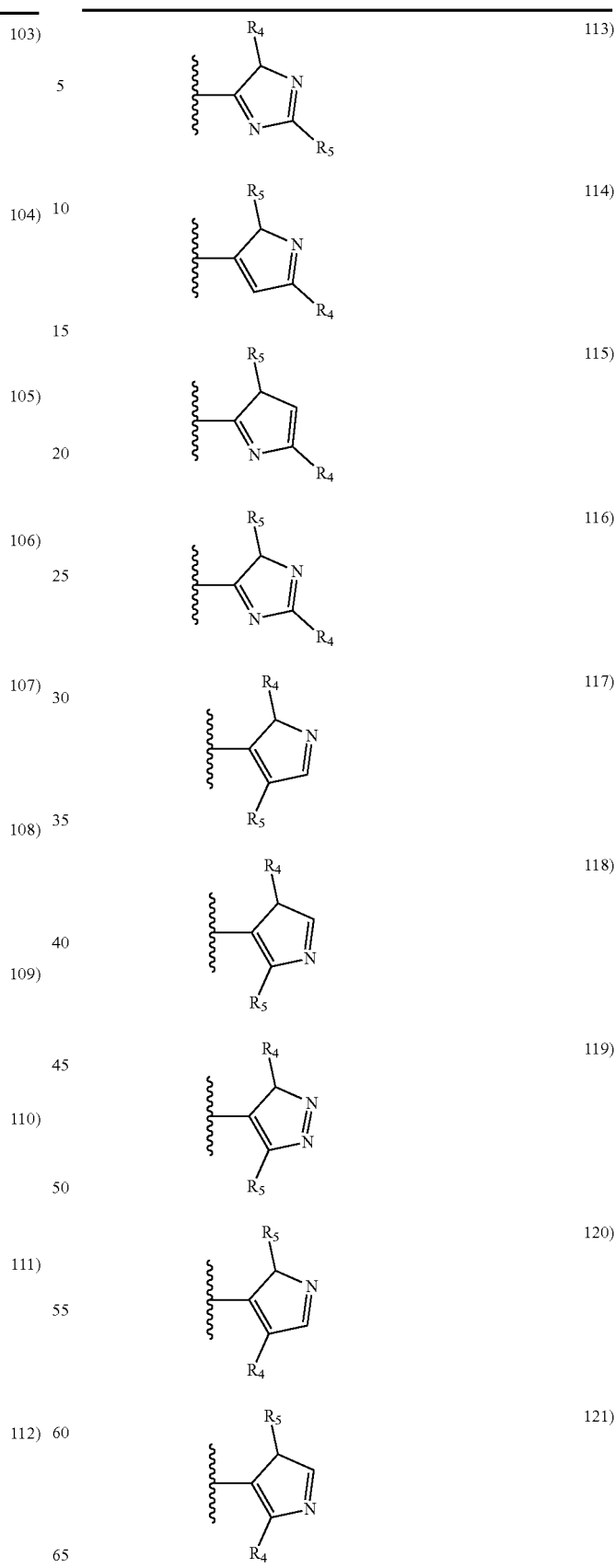

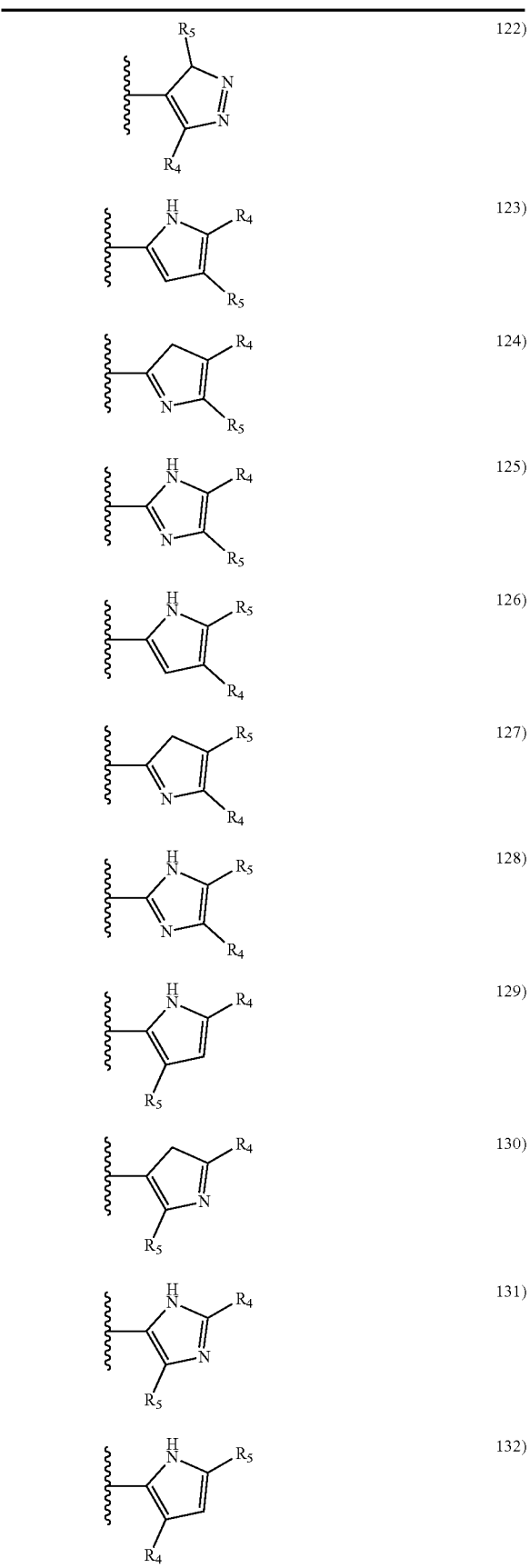
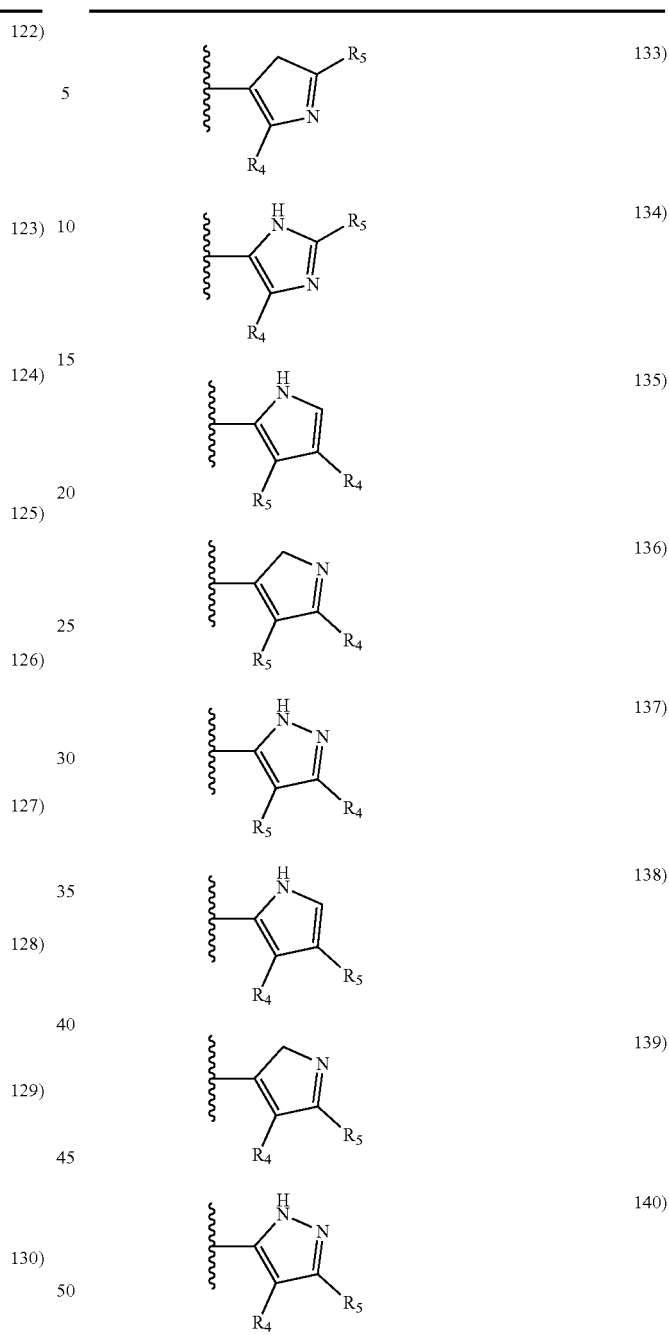

It is preferable that X is a six-membered heterocyclic group. Preferably, the six-membered heterocyclic group has at least one heteroatom present in the meta-position (i.e. members 3, 6, 8, 10, 11, 13, 15 to 18, 20, 22 to 24, 26, 46, 48, 50, 52, 54, 56 to 58, 60 to 64, 66 to 69, 72, 73, 75, 78, 79, 81, 83 to 86, 88, 90, 92, 94, 96 and 98 of Table 2), more preferably the six-member heterocyclic group has just one heteroatom and that is present in the meta-position (i.e. members 3, 11, 13, 22, 46, 52, 57, 58, 63, 64, 69, 75, 81, 83, 88 and 94 of Table 2) (in general $R_5$ is preferably absent).

Ortho and/or meta positions for $R_4$ and $R_5$ may be particularly preferred in some embodiments and meta may be especially preferred, particularly when X is pyridine, more particularly when the pyridine nitrogen is in the meta position i.e. the para position as a position for $R_4$ or $R_5$ is less favoured when X is pyridine with the pyridine nitrogen is in the meta position. These preferences apply in particular when $R_1$ is $OR_2$.

Particularly preferred compounds are those in which some or all of the moieties discussed above are in their preferred form; thus, for example, preferred $R_1$ groups are preferred in the context of all alternatives for X, $R_4$ and $R_5$, but particularly preferred compounds are those in which preferred $R_1$ groups are combined with preferred alternatives for X, $R_4$ and $R_5$, and so on.

Preferred combinations of X, $R_4$ and $R_5$ (where $R_5$ is absent) are presented in Table 3.

TABLE 3

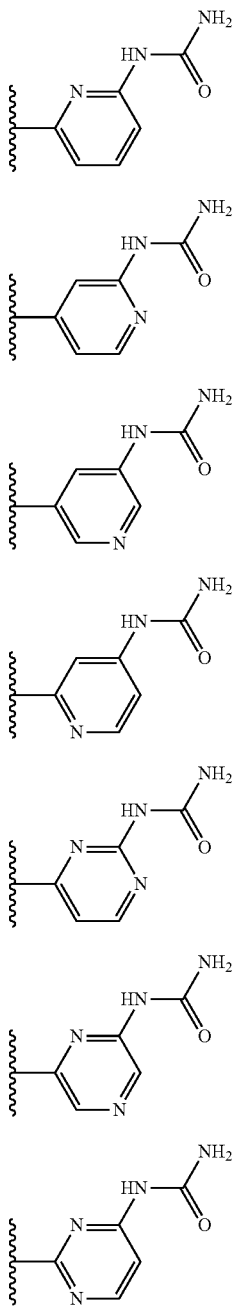

TABLE 3-continued

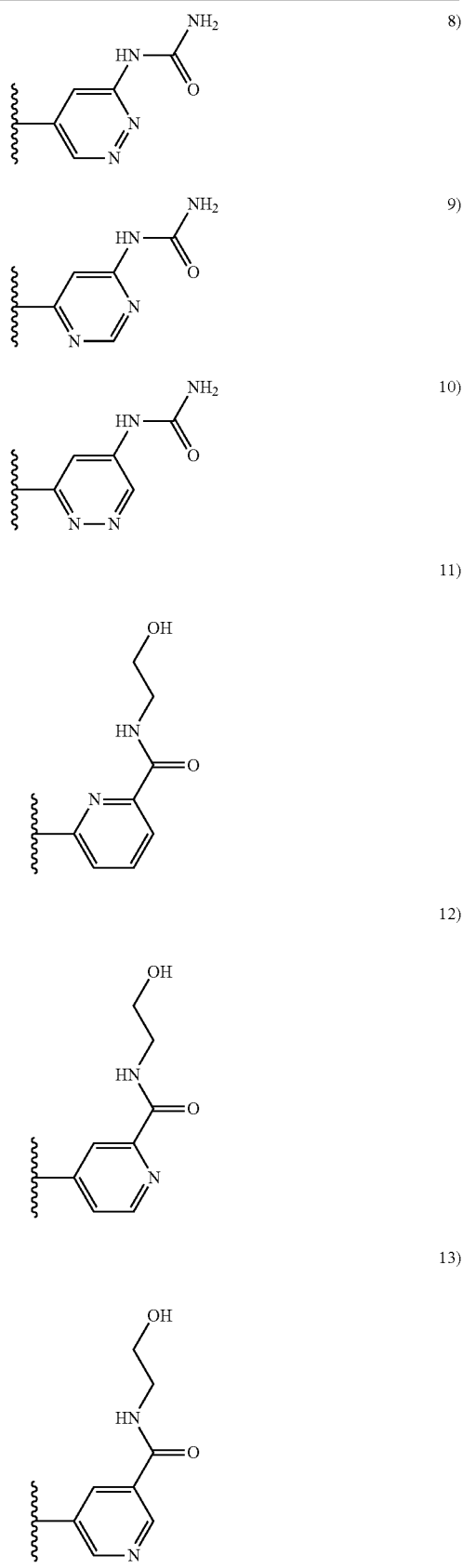

TABLE 3-continued
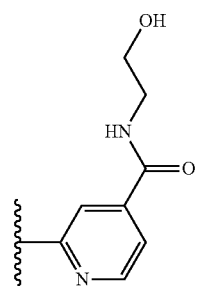 [SMILES: *c1cc(C(=O)NCCO)ccn1] 14)
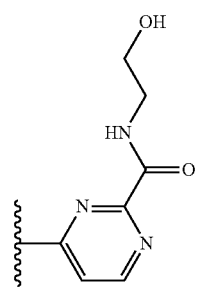 [SMILES: *c1ccnc(C(=O)NCCO)n1] 15)
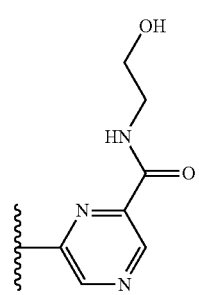 [SMILES: *c1cncc(C(=O)NCCO)n1] 16)
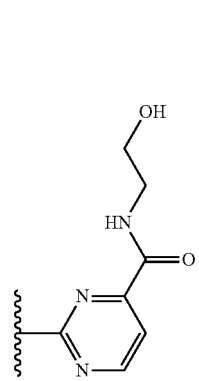 [SMILES: *c1nccc(C(=O)NCCO)n1] 17)
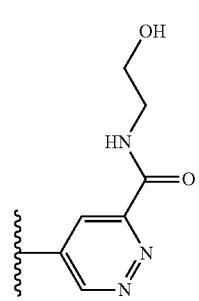 [SMILES: *c1cnnc(C(=O)NCCO)c1] 18)
TABLE 3-continued
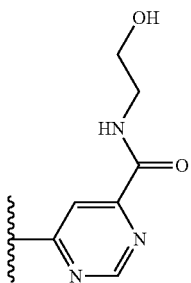 [SMILES: *c1cc(C(=O)NCCO)ncn1] 19)
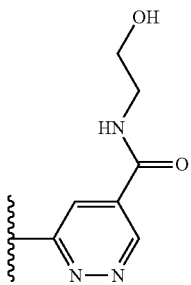 [SMILES: *c1cc(C(=O)NCCO)cnn1] 20)
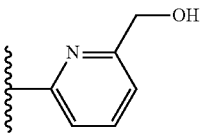 [SMILES: *c1cccc(CO)n1] 21)
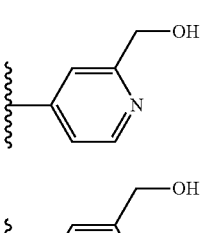 22)
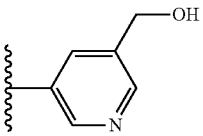 23)
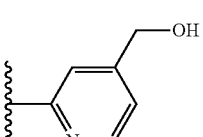 24)
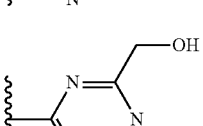 25)
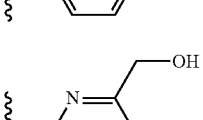 26)
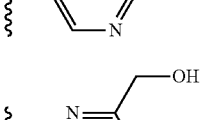 27)

TABLE 3-continued
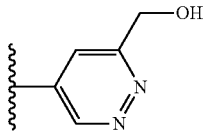 [SMILES: *c1cnnc(CO)c1] 28)
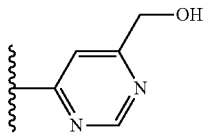 29)
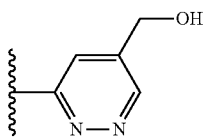 30)
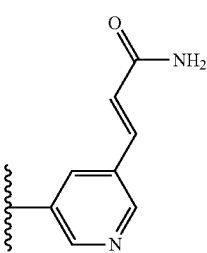 [SMILES: *c1cncc(/C=C/C(N)=O)c1] 31)
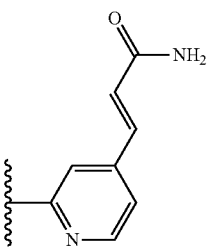 32)
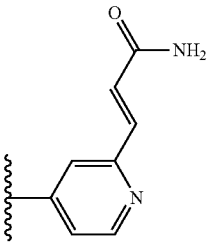 [SMILES: *c1ccnc(/C=C/C(N)=O)c1] 33)
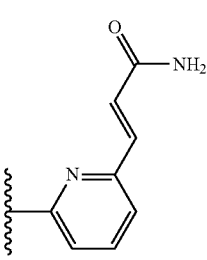 [SMILES: *c1cccc(/C=C/C(N)=O)n1] 34)
TABLE 3-continued
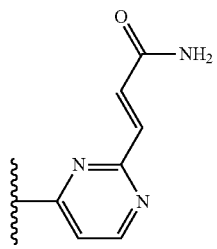 [SMILES: *c1ccnc(/C=C/C(N)=O)n1] 35)
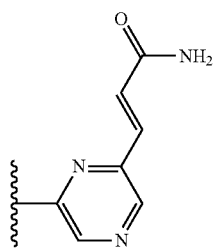 [SMILES: *c1cncc(/C=C/C(N)=O)n1] 36)
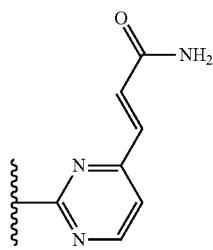 [SMILES: *c1nccc(/C=C/C(N)=O)n1] 37)
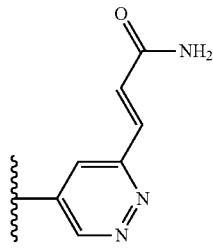 [SMILES: *c1cnnc(/C=C/C(N)=O)c1] 38)
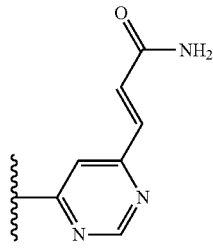 [SMILES: *c1cc(/C=C/C(N)=O)ncn1] 39)
40)

TABLE 3-continued
41) 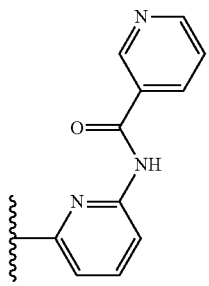 [SMILES: *c1cccc(NC(=O)c2cccnc2)n1]
42) 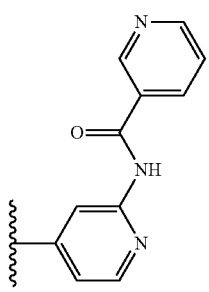 [SMILES: *c1ccnc(NC(=O)c2cccnc2)c1]
43) 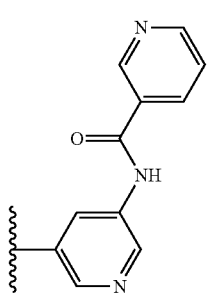 [SMILES: *c1cncc(NC(=O)c2cccnc2)c1]
44) 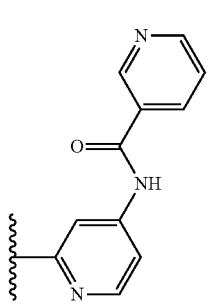 [SMILES: *c1cc(NC(=O)c2cccnc2)ccn1]
45) 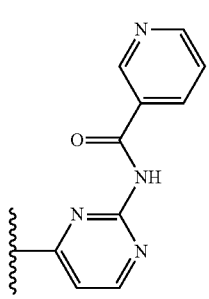 [SMILES: *c1ccnc(NC(=O)c2cccnc2)n1]
TABLE 3-continued
46) 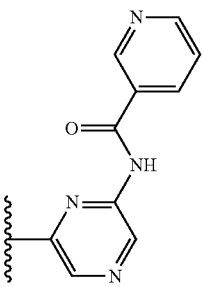 [SMILES: *c1cncc(NC(=O)c2cccnc2)n1]
47) 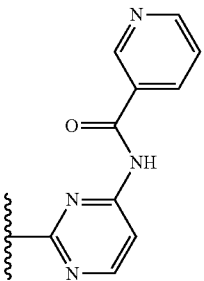 [SMILES: *c1nccc(NC(=O)c2cccnc2)n1]
48) 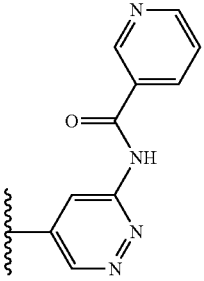 [SMILES: *c1cnnc(NC(=O)c2cccnc2)c1]
49) 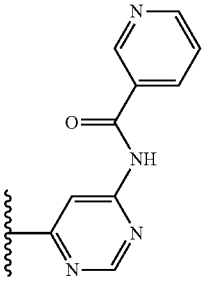 [SMILES: *c1cc(NC(=O)c2cccnc2)ncn1]
50) 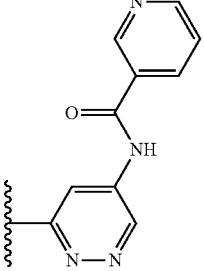
51) 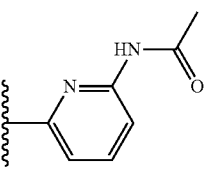

TABLE 3-continued
52) 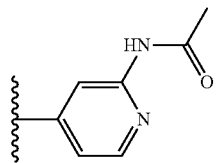
53) 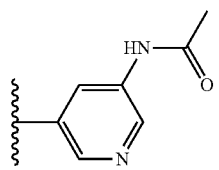
54) 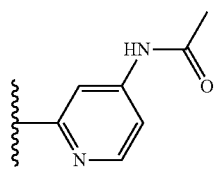
55) 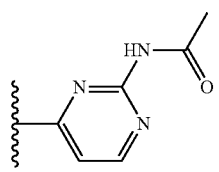
56) 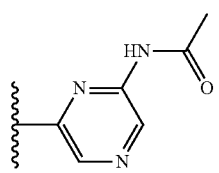 [SMILES: *c1cncc(NC(C)=O)n1]
57) 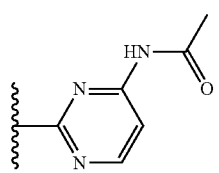 [SMILES: *c1nccc(NC(C)=O)n1]
58) 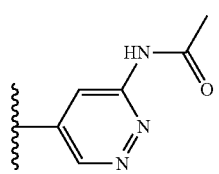 [SMILES: *c1cnnc(NC(C)=O)c1]
59) 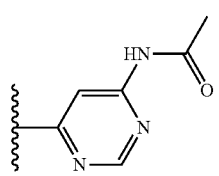 [SMILES: *c1cc(NC(C)=O)ncn1]
60) 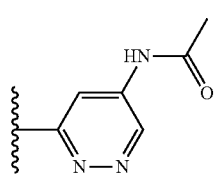
TABLE 3-continued
61) 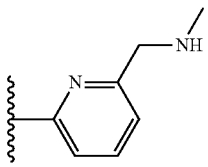
62) 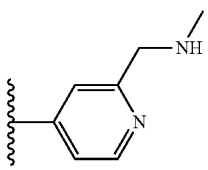
63) 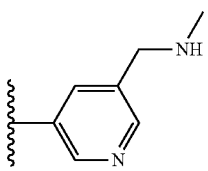
64) 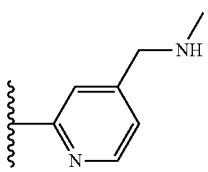
65) 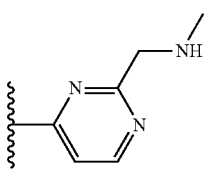 [SMILES: *c1ccnc(CNC)n1]
66) 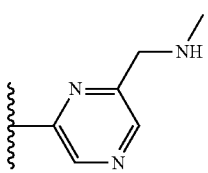 [SMILES: *c1cncc(CNC)n1]
67) 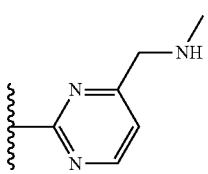 [SMILES: *c1nccc(CNC)n1]
68) 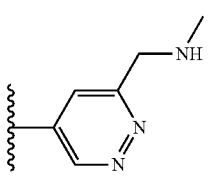 [SMILES: *c1cnnc(CNC)c1]
69) 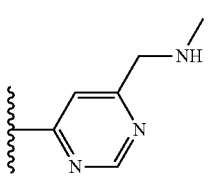

TABLE 3-continued
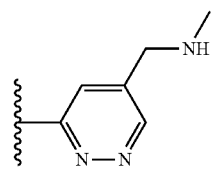 [SMILES: *c1cc(CNC)cnn1] 70)
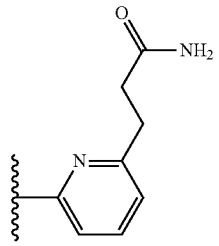 [SMILES: *c1cccc(CCC(N)=O)n1] 71)
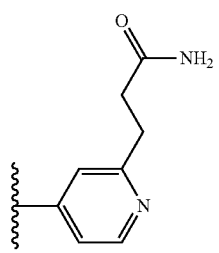 [SMILES: *c1ccnc(CCC(N)=O)c1] 72)
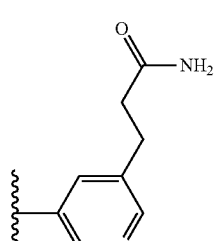 73)
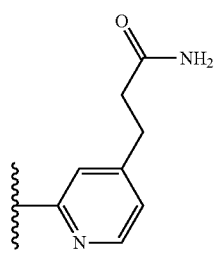 [SMILES: *c1cc(CCC(N)=O)ccn1] 74)
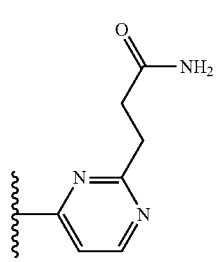 [SMILES: *c1ccnc(CCC(N)=O)n1] 75)
TABLE 3-continued
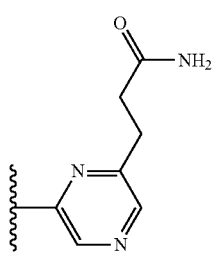 [SMILES: *c1cncc(CCC(N)=O)n1] 76)
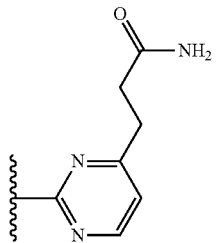 [SMILES: *c1nccc(CCC(N)=O)n1] 77)
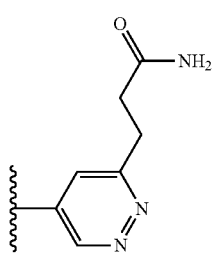 [SMILES: *c1cnnc(CCC(N)=O)c1] 78)
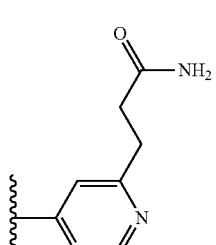 79)
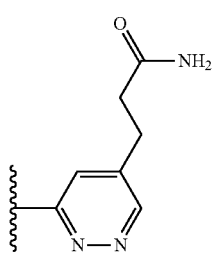 [SMILES: *c1cc(CCC(N)=O)cnn1] 80)
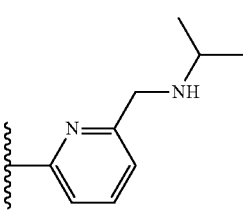 [SMILES: *c1cccc(CNC(C)C)n1] 81)

TABLE 3-continued
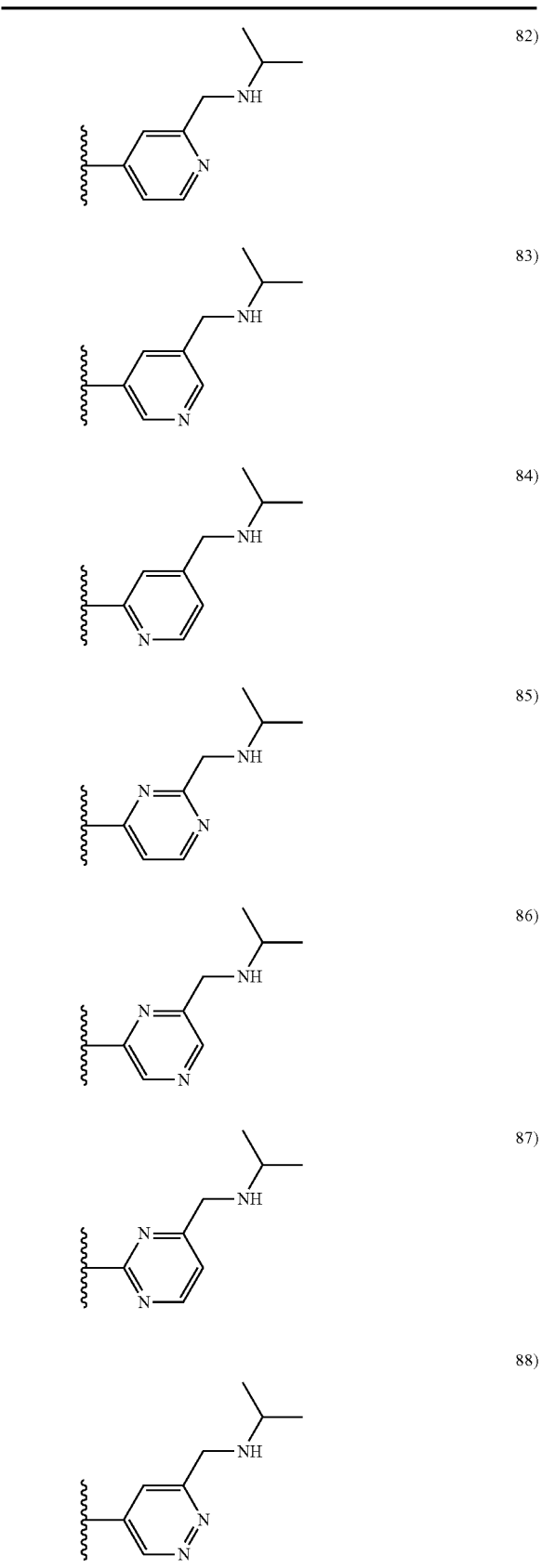
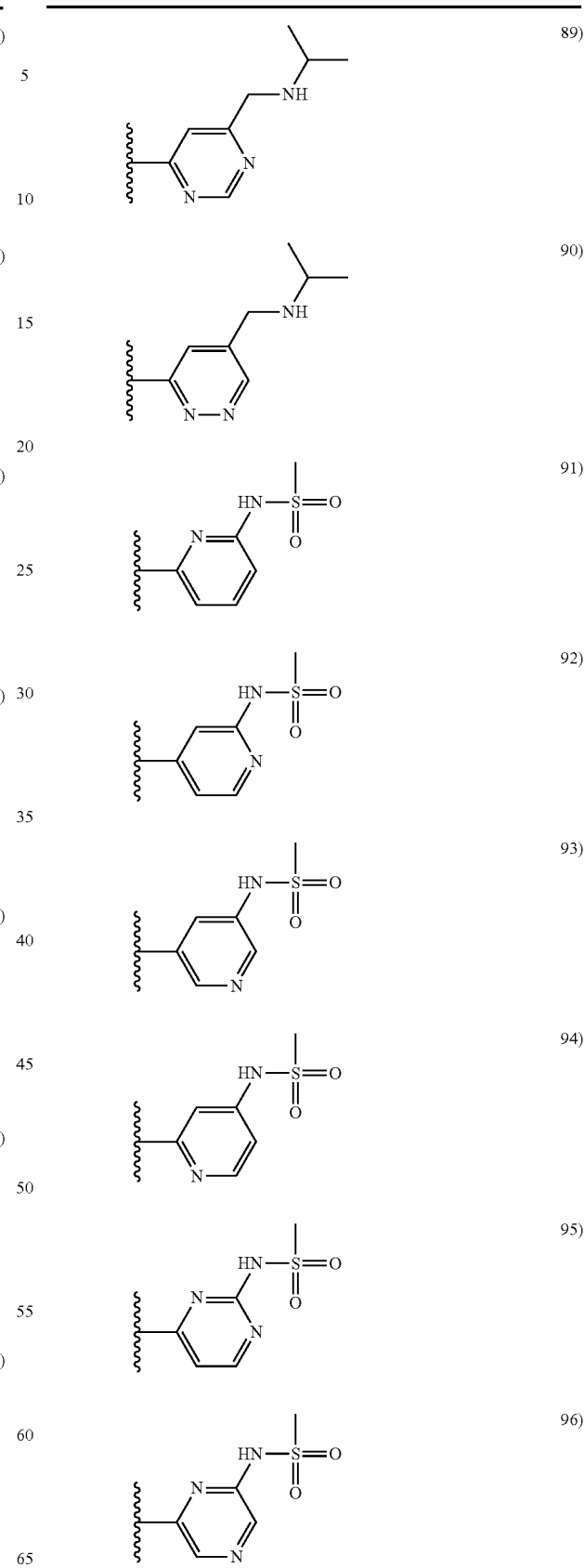

TABLE 3-continued
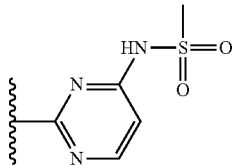 [SMILES: *c1nccc(NS(C)(=O)=O)n1] 97)
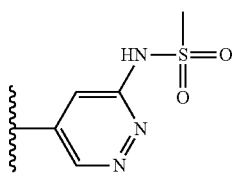 [SMILES: *c1cnnc(NS(C)(=O)=O)c1] 98)
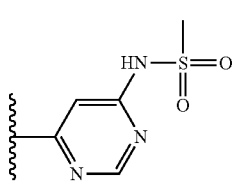 [SMILES: *c1cc(NS(C)(=O)=O)ncn1] 99)
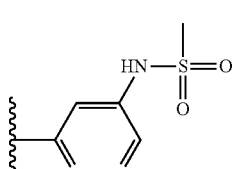 100)
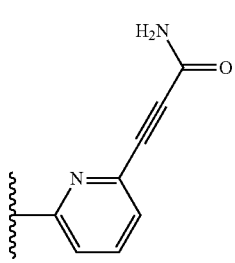 [SMILES: *c1cccc(C#CC(N)=O)n1] 101)
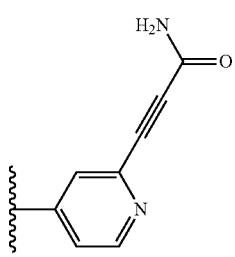 [SMILES: *c1ccnc(C#CC(N)=O)c1] 102)
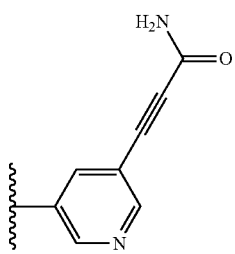 [SMILES: *c1cncc(C#CC(N)=O)c1] 103)
TABLE 3-continued
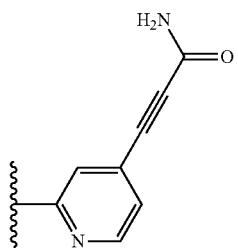 [SMILES: *c1cc(C#CC(N)=O)ccn1] 104)
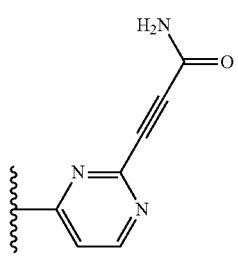 [SMILES: *c1ccnc(C#CC(N)=O)n1] 105)
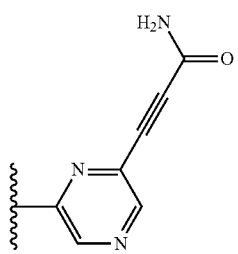 [SMILES: *c1cncc(C#CC(N)=O)n1] 106)
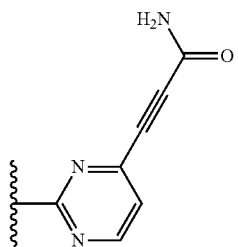 [SMILES: *c1nccc(C#CC(N)=O)n1] 107)
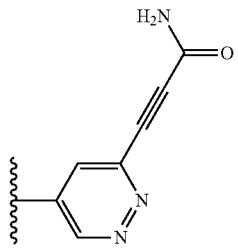 [SMILES: *c1cnnc(C#CC(N)=O)c1] 108)
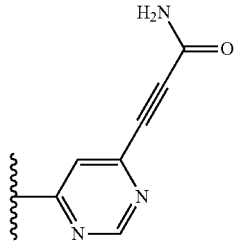 [SMILES: *c1cc(C#CC(N)=O)ncn1] 109)

TABLE 3-continued

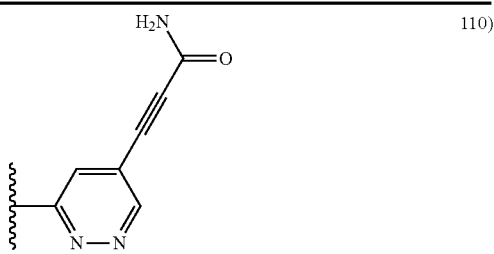
110)

As discussed above, preferably the six-membered heterocyclic group has at least one heteroatom present in the meta-position (i.e. members 3, 6, 8, 10, 13, 16, 18, 20, 23, 26, 28, 30, 31, 36, 38, 40, 43, 46, 48, 50, 53, 56, 58, 60, 63, 66, 68, 70, 73, 76, 78, 80, 83, 86, 88, 90, 93, 96, 98, 100, 103, 106, 108 and 110 of Table 3), more preferably the six-member heterocyclic group has one heteroatom present in the meta-position (i.e. members 3, 13, 23, 31, 43, 53, 63, 73, 83, 93 and 103 of Table 3).

Examples of especially preferred compounds are shown in Tables 4 and 7.

Neurodegenerative disorders according to the present invention include AD (including familial AD), PD (including postencephalitic parkinsonism), Pick's disease, progressive supranuclear palsy, corticobasal degeneration, cognitive deficit in Schizophrenia, mild cognitive impairment, age-associated memory impairment, age-related cognitive decline, cognitive impairement no dementia, multiple sclerosis, Huntington's Disease, amyotrophic lateral sclerosis, motor neuron diseases, Multiple System Atrophy, Corticobasal Degeneration, Progressive Supranuclear Paresis, Guillain-Barre Syndrome, Chronic Inflammatory Demyelinating Polyneuropathy, Frontotemporal dementia Parkinson's Type, Niemann-Pick's Disease, traumatic brain injury, dementia pugilistica, Creutzfeld-Jacob Disease, prion diseases and agyrophilic grain disease.

In particular the present invention concerns the treatment or prevention of AD, and the treatment or prevention of PD. Preferably, the subject has DS, more particularly the present invention concerns the treatment or prevention of AD in patients with DS. Inhibition of tau phosphorylation is a particular target for the treatment of AD and PD, and the inhibition of the phosphorylation of the protein encoded by parkin is also a particular target for the treatment of PD.

In a further aspect, the present invention provides an in vitro method of inhibiting phosphorylation of tau or the protein encoded by parkin or inhibiting the formation of neurofibrillary tangles or inhibiting DYRK1A comprising contacting a sample of or containing DYRK1A with a compound of formula (I).

In order to facilitate passage through the Blood Brain Barrier, it may be preferable that the V—W—Y—Z substituent does not comprise moieties known to have a charge at physiological pH, such as carboxylic acids.

Treatment includes an improvement in one or more of the symptoms of the disorder or a delay in onset of one or more symptoms as assessed by a clinician, optionally together with patient feedback. Symptoms of AD include memory loss, confusion, mood and personality changes, hallucinations, delusions and paranoia, problems with communication, weight loss, seizures, skin infections, difficulty in swallowing and lack of control of bowel and bladder. With respect to PD, early in the disease the most obvious signs are shaking, rigidity, slowness of movement, and difficulty with walking. Thinking and behavioural problems may also occur. Dementia becomes common in the advanced stages of PD. Other symptoms include sensory, sleep, and emotional problems.

Treatment includes slowing or halting disease progression and thus treatment may not result in significant observable benefits unless a comparison is made with expected (untreated) progression of the disorder. Likewise, treatment may be beneficial if an anticipated symptom is delayed in its appearance.

The subject will typically have been identified as in need of treatment. This may be determined based on assessment of cognitive performance or any other measure which leads to a diagnosis that the patient has a neurodegenerative disorder or is at risk of developing such a disorder. In the case of AD this determination may be achieved through microscopic histological or other investigations to observe the formation of amyloid plaques and/or neurofibrillary tangles. Subjects with DS are a preferred group who may be treated in accordance with the present invention.

Prevention of a neurodegenerative disorder may include prevention for a period of time, in other words delayed onset. Suitable patients for prevention include those with DS, in particular, DS patients over the age of twenty or thirty. Generally, if a patient has been shown to have one or more markers of a neurodegenerative disorder but no symptoms as yet, such a patient is considered to be "treated" in accordance with the present invention. "Prevention" assumes the patient has neither symptoms nor confirmed clinical markers of disease.

The present invention may enable inhibition of the formation of neurofibrillary tangles. These (tau) tangles can be assessed by any convenient method known in the art, for example using a microscope to observe the aggregates of the tau protein, a suitable method is described by Armstrong in *Folia Neuropathol.* 2008; 46 (1): 26-31.

Inhibition may be observed on treatment through a reduction in the size of the tangles or in the extent of their distribution. Their formation is "inhibited" even if the amount observed has not decreased on treatment, if the amount would have been expected to increase without treatment.

Alternatively viewed, the compounds described herein treat or prevent neurodegenerative disorders through inhibition of DYRK1A. A method to measure inhibition of DYRK1A is described in the Examples herein. A suitable assay could be performed using ADP-Glo™ kinase assay of Promega. This is applicable with respect to DM also, discussed below.

Proliferation of β-cells is a particular target for the treatment of DM. Proliferation of these cells can be measured through simple in vitro cell proliferation assays, such as the CellTiter-Glo assay by Promega, on reversibly immortilised β cells, such as R7T1 murine cells. Alternatively, β-cell division can be monitored through incorporating the modified thymidine analogue 5-ethynyl-2'-deoxyuridine (EdU) in order to measure DNA synthesis in the S phase. Insulin secretion can also be measured through using a commercially available enzyme-linked immunosorbent (ELISA) assay. These methods are discussed in Shen et al. surpra. In vivo, the effectiveness of the compounds of the present invention can be determined simply through assessing glycaemic control in an animal or patient (as is carried out routinely throughout the life of a diabetic patient).

DM can conveniently be diagnosed and monitored through assessing fasting plasma glucose levels (in a healthy patient this is less than 6.1 mmol/l and in a diabetic patient this is greater than 7.0 mmol/l), glucose tolerance (the plasma glucose level two hours after a 75 g glucose load) (in a healthy patient this is less than 7.8 mmol/l and in a diabetic patient this is greater than 11.0 mmol/l) and glycated haemoglobin ($HbA_{1C}$), a form of haemoglobin that can be measured in order to identify a three-month average plasma glucose concentration (in a healthy patient this is less than 42 mmol/mol and in a diabetic patient this is greater than 48 mmol/mol). Such assessments can be carried out on patients not yet showing signs or symptoms of DM but at risk of developing DM, and indeed such assessments can confirm that a patient is at risk of developing DM (such at risk patients could have a fasting plasma glucose level of between 6.1 and 7.0 mmol/l, or a glucose tolerance level of between 7.8 and 11.0 mmol/l, or a $HbA_{1C}$ of between 42 and 48 mmol/mol). Thus, the compounds of the present invention can be used to prevent the development of DM in, for example, a patient at risk of developing DM, or alternatively used to treat a patient that has been diagnosed with DM.

Metabolic Syndrome can be conveniently diagnosed and monitored through study of a patient's insulin resistance, abdominal obesity, blood sugar levels and serum triglyceride levels.

In a further aspect, the present invention provides a method of inhibiting DYRK1A or DYRK1B and/or a reaction catalysed by DYRK1A or DYRK1B, the method comprising contacting said kinase with a compound of formula (I) as defined herein. Such methods may be in vivo or ex vivo.

Animals which may be treated include domestic animals, in particular cats and dogs and livestock animals such as pigs, cows, sheep or goats as well as horses. Laboratory animals, mice, rabbits etc. may also be treated. Treatment of humans is nevertheless preferred.

Methods for the synthesis of compounds of the invention are described in the Examples hereto, non-exemplified compounds can be prepared by methods which are analogous to the schemes and protocols described herein.

Methods of synthesising compounds of the invention, in particular methods described in the Examples, constitute a further aspect of the present invention.

Pharmaceutical compositions containing the compounds of the present invention and a suitable carrier, diluent or excipient constitute a further aspect of the present invention.

The compositions according to the invention and compositions comprising a compound of formula (I) as defined herein for use according to the invention, may be presented, for example, in a form suitable for oral, nasal, parenteral, intravenal, or rectal administration.

The active compounds defined herein may be presented in the conventional pharmacological forms of administration, such as tablets, coated tablets, nasal sprays, inhalers, solutions, emulsions, liposomes, powders, capsules or sustained release forms. As used herein, the term "pharmaceutical" includes veterinary applications.

Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays administration may be formulated similarly in aqueous solution and packed into spray containers either with an aerosol propellant or provided with means for manual compression.

Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Tablets for oral administration are preferred.

Pharmaceutical compositions comprising a compound of formula (I) may additionally comprise further active ingredients, including, for example, other active agents for the treatment or prevention of a neurodegenerative disorder or for the treatment of DM. Likewise the medical uses and methods of treatment may additionally comprise further active ingredients, including, for example, other active agents for the treatment or prevention of a neurodegenerative disorder (for example AD or PD) or for the treatment or prevention of DM.

Pharmaceutical packs comprising a compound of formula (I) and a further active agent for the treatment or prevention of a neurodegenerative disorder or for the treatment of DM not in admixture are a further aspect of the present invention. All such combination products and therapies which also comprise a second active agent for the treatment or prevention of a neurodegenerative disorder or for the treatment of DM may employ a compound "disclaimed" above in the context of compounds per se of the invention.

In employing such compositions systemically (intra-muscular, intravenous, intraperitoneal), the active molecule is generally present in an amount to achieve a serum level of the active molecule of at least about 1-10 micromolar Such serum levels may be achieved by incorporating the bioactive molecule in a composition to be administered systemically at a dose of from 50 mg-250 mg.

It is appreciated that appropriate dosages will vary from patient to patient dependent on age, sex, previous treatments, severity of symptoms presented etc.

The above description describes numerous features of the present invention and in most cases preferred embodiments of each feature are described. It will be appreciated that each preferred embodiment of a given feature may provide a molecule, use, method etc. of the invention which is preferred, both when combined with the other features of the invention in their most general form and when combined with preferred embodiments of other features. The effect of selecting multiple preferred embodiments may be additive or synergistic. Thus all such combinations are contemplated unless the technical context obviously makes them mutually exclusive or contradictory. In general each feature and preferred embodiments of it are independent of the other features and hence combinations of preferred embodiments may be presented to describe sub-sets of the most general definitions without providing the skilled reader with any new concepts or information as such.

The invention will now be further described in the following Examples and with reference to the figures which show the following:

FIG. 1 Scheme showing how some of the benzothiazolylpyridines in Table 4 can conveniently be prepared using a palladium catalysed coupling of a substituted benzo-1,3-thiazole and a suitably substituted bromopyridine derivative.

Figure 2:
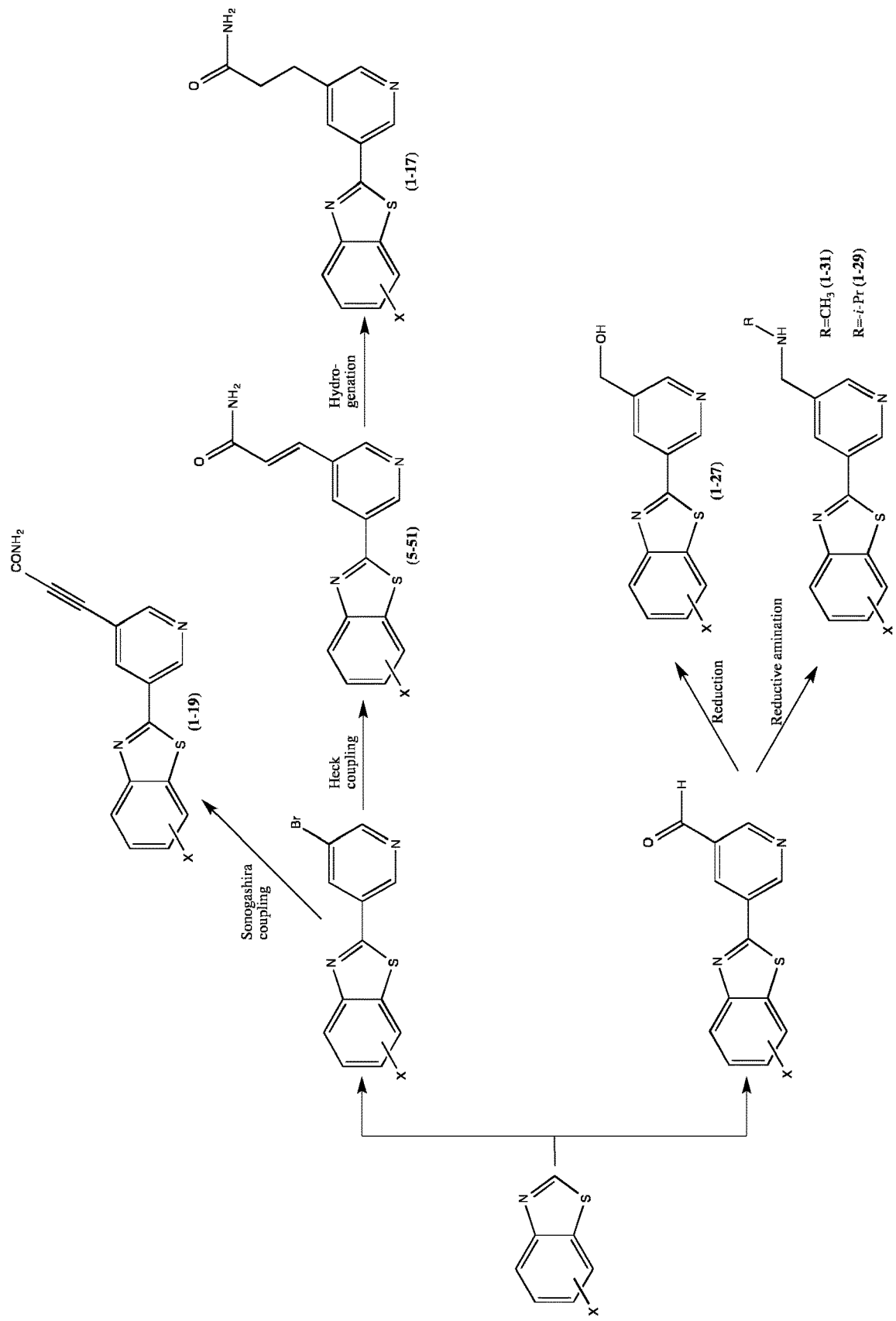

FIG. 2 Scheme showing how some of the benzothiazolylpyridines presented in Table 4 are available from benzothiazolylformylpyridines.

FIG. 3 Binding poses of benzothiazolylpyridine derivative N-(5-(5-Hydroxybenzo[d]thiazol-2-yl)pyridin-3-yl)methanesulfonamide (4-99) in the DYRK1A ATP binding pocket.

Figure 4:
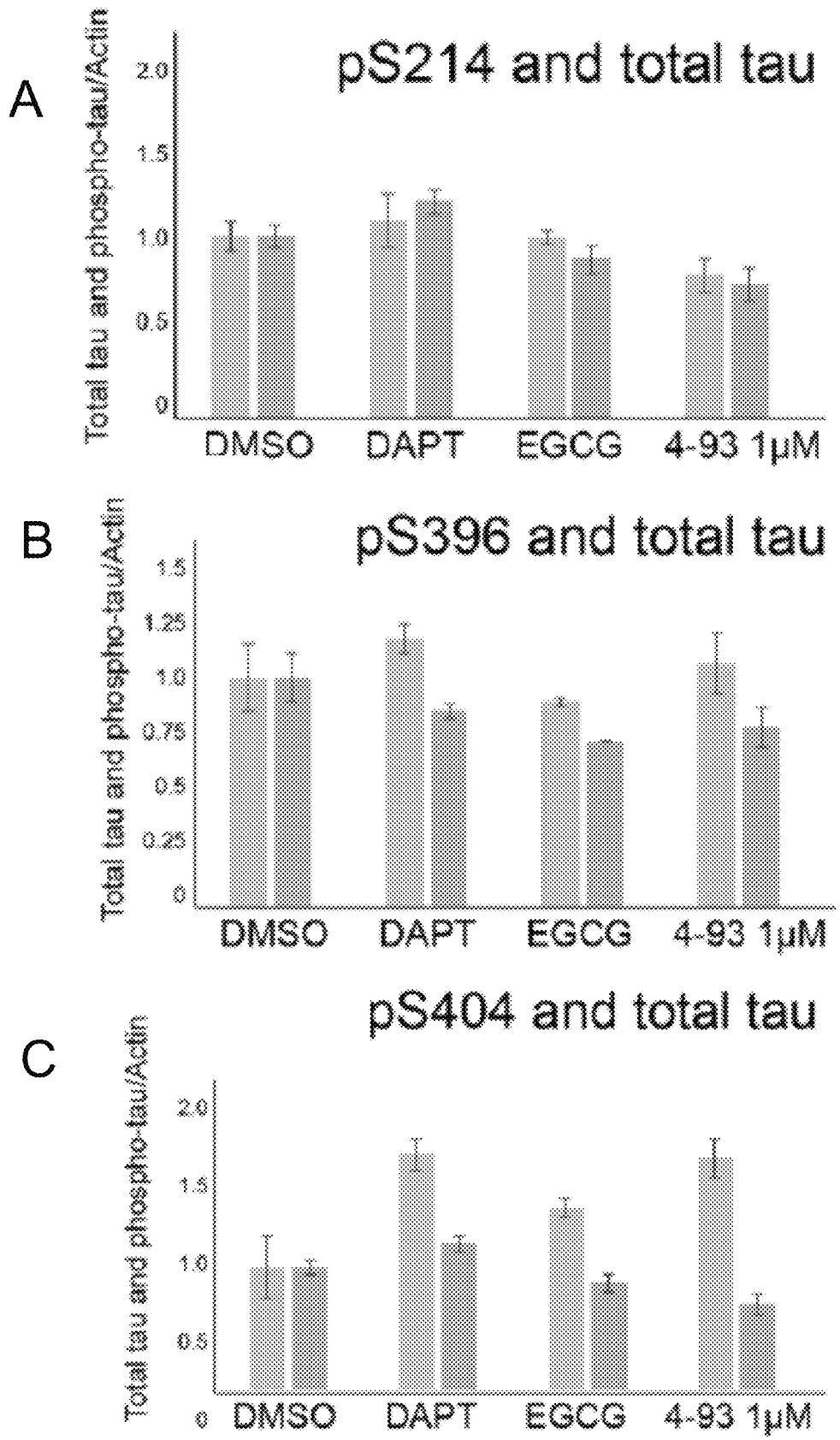

FIG. 4 Treatment of control neurons with DAPT and DYRK1A inhibitors did not increase total tau levels (right hand bars) but resulted in a non-significant increase in tau/MAPT phosphorylation (left hand bars) compared to DMSO treated controls. Tau phosphorylation was measured at the following sites: serine 214 (FIG. 4A), serine 396 (FIG. 4B) and serine 404 (FIG. 4C). Increasing tau phosphorylation is consistent with compounds increasing neurogenesis. Phospho-tau and total tau signal was normalised to β-actin. (Error bars=SEM). DAPT is a γ-secretase inhibitor with known effect on tau-phosphorylation, EGCG is epigallocatechin gallate, a naturally occurring polyphenol that is a known DYRK1A inhibitor.

Figure 5:
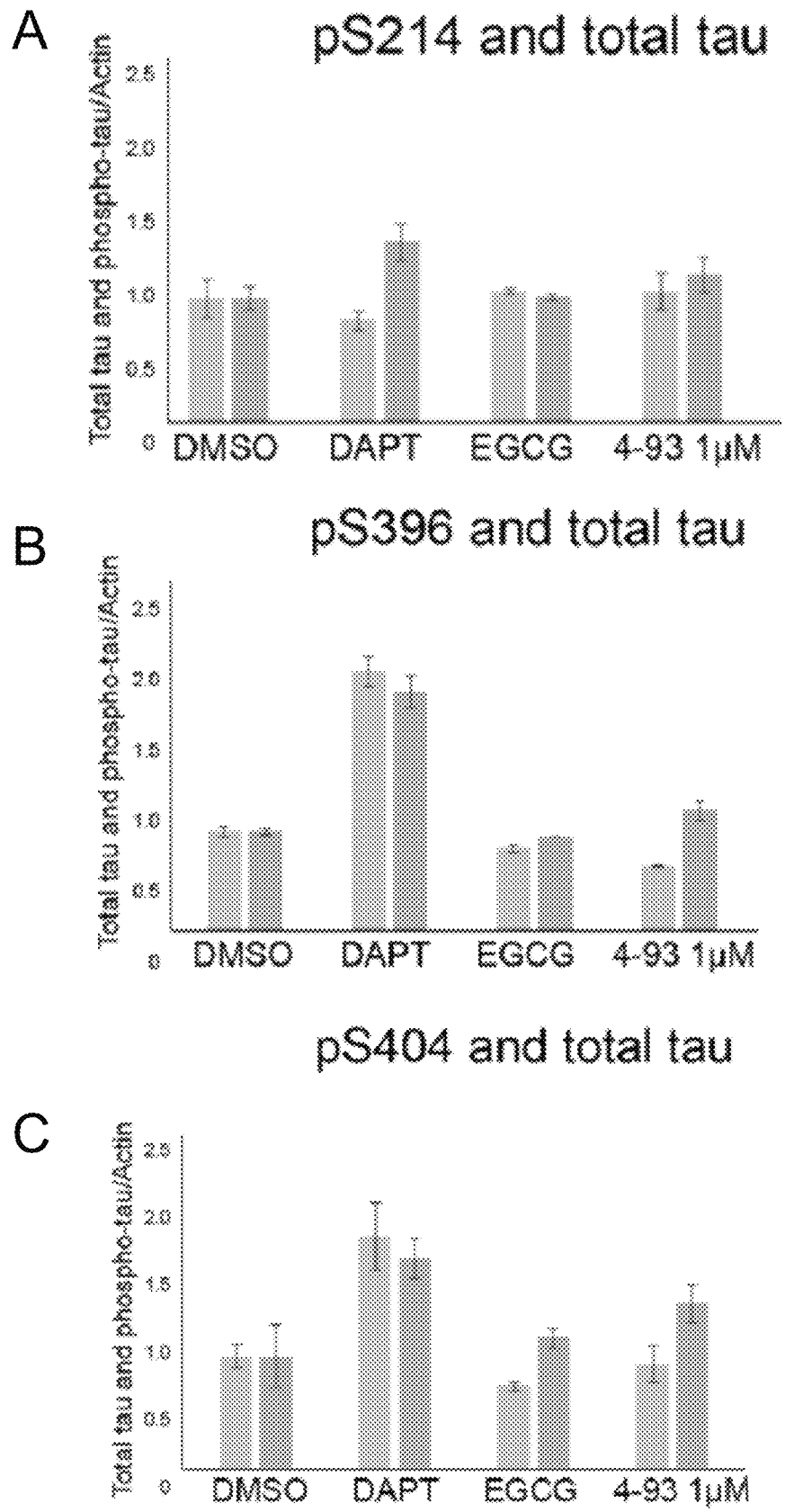

FIG. 5 Treatment of TS21 neurons with DYRK1A inhibitors gave a striking reduction in tau/MAPT phosphorylation (right hand bars) at sites that are highly phosphorylated in TS21 neurons and in Alzheimer's diseased brain and an increase in total tau (left hand bars). Inhibitor 4-93 at non-toxic concentrations significantly reduced tau phosphorylation at serine 396 (FIG. 5B) and serine 404 (FIG. 5C) in TS21 neurons. Phosphorylation at serine 214 (FIG. 5A), a site that is not phosphorylated by DYRK1A, was unaffected by DYRK1A inhibition. Phospho-tau and total tau levels were normalised to β-actin. (Error bars=SEM). DAPT is a γ-secretase inhibitor with known effect on tau-phosphorylation, EGCG is epigallocatechin gallate, a naturally occurring polyphenol that is a known DYRK1A inhibitor.

Figure 6:
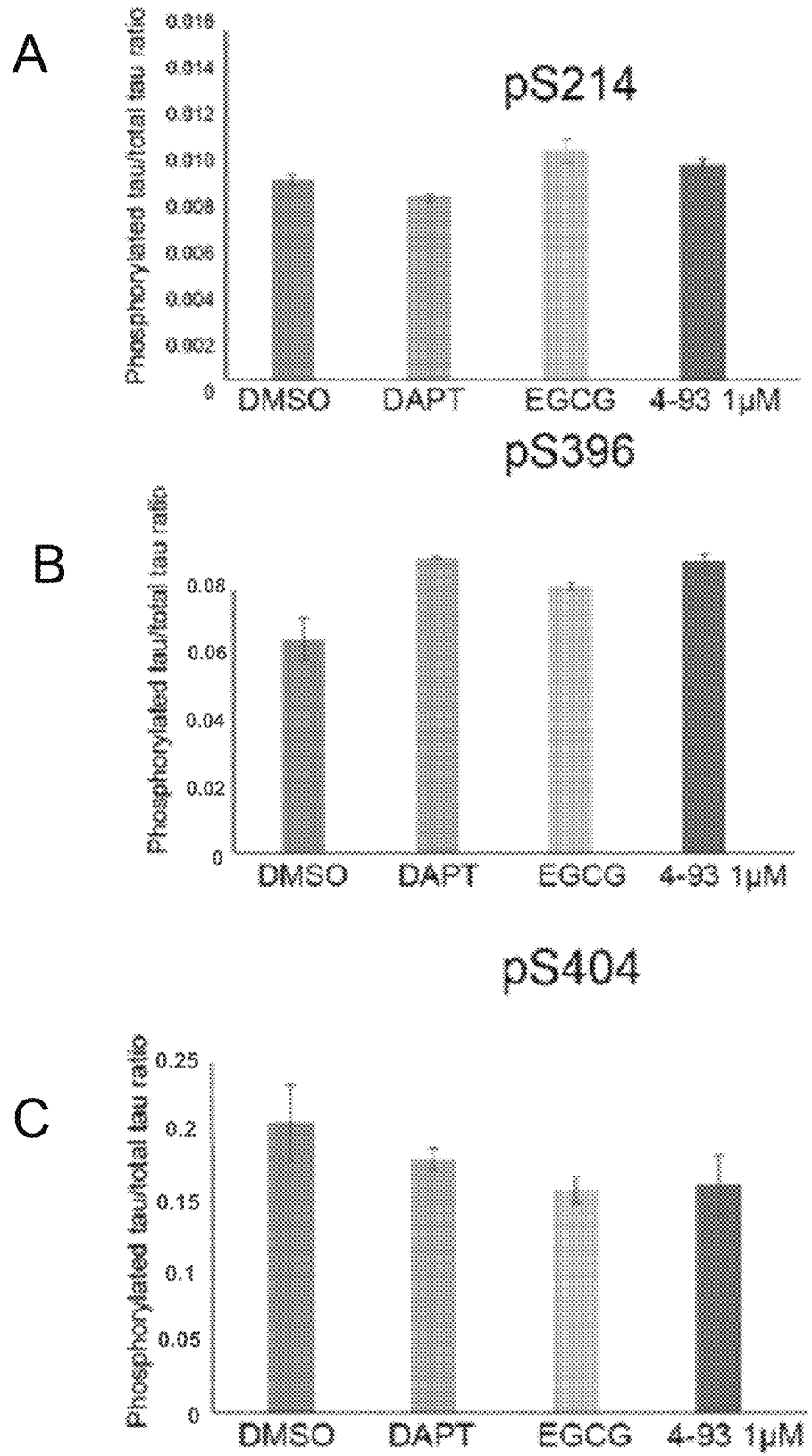

FIG. 6 Quantification of phosphorylated tau normalised to total tau levels in control neurons following ten days treatment with control compounds and DYRK1A inhibitors. Levels of tau/MAPT phosphorylated at serine 214 (FIG. 6A), serine 396 (FIG. 6B) and serine 404 (FIG. 6C) were unaffected by DYRK1A inhibition when normalised to total tau/MAPT levels.

Figure 7:
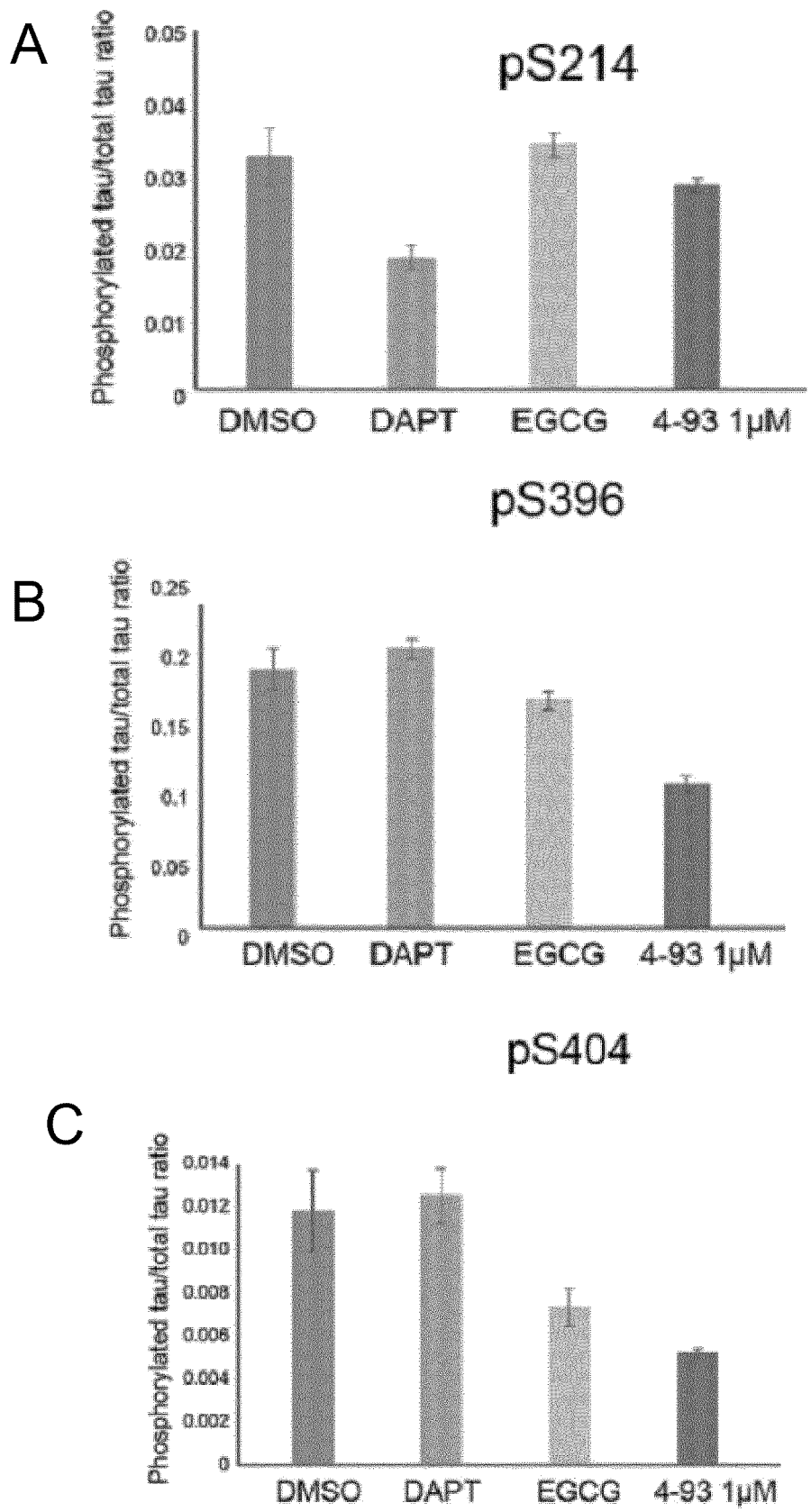

FIG. 7 Quantification of phosphorylated tau normalised to total tau levels in TS21 neurons following ten days treatment with control compounds and DYRK1A inhibitors. Levels of phosphorylated tau/MAPT at serine 396 (FIG. 7B) and serine 404 (FIG. 7C) but not serine 214 (FIG. 7A) in TS21 neurons treated with DYRK1A inhibitors were significantly lower than DMSO treated controls or DAPT treated positive controls when normalised to total tau/MAPT levels.

EXAMPLES

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes shown below and in the Figures. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds can be synthesized using the intermediates prepared in accordance to the general schemes and other materials, compounds and reagents are known to those skilled in the art. All such compounds thereof are intended to be encompassed within the scope of the present invention Example A A. Preparation of Benzothiazolylpyridine Derivatives The following compounds presented in Table 4 were prepared.

TABLE 4

| Structure | Compound Name |
|---|---|
| [Structure: CH$_3$O-benzothiazole-pyridine-NH-C(=O)-NH$_2$] | 5-85 |
| [Structure: CH$_3$O-benzothiazole-pyridine-CH=CH-C(=O)-NH$_2$] | 5-51 |
| [Structure: CH$_3$O-benzothiazole-pyridine-C≡C-C(=O)-NH$_2$] | 1-19 |
| [Structure: CH$_3$O-benzothiazole-pyridine-CH$_2$-NH-CH$_3$] | 1-31 |

TABLE 4-continued

| Structure | Compound Name |
|---|---|
| 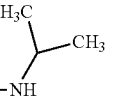 | 1-29 |
| 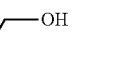 | 1-27 |
| 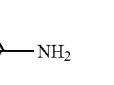 | 1-17 |
| 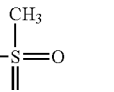 | 5-25 |
| 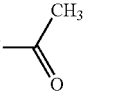 | 5-23 |
| 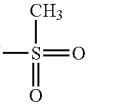 | 4-99 |
| 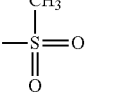 | 4-95 |
| 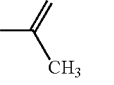 | 4-93 |

The different benzothiazolylpyridines in Table 4 can conveniently be prepared using a palladium catalysed coupling of a substituted benzo-1,3-thiazole and a suitably substituted bromopyridine derivative as shown as Step 1 in the scheme of FIG. 1. Depending on the R-group, several classes of benzothiazolylpyridines can be prepared. If R=NH$_2$, acetylation using an acid chloride (or anhydride) will give rise to benzothiazolylpyridines with an acylamido substituent on the pyridine ring (Alternative 1 of FIG. 1), whereas alkylsulfonylation using an alkylsulfonyl chloride furnishes benzothiazolylpyridines with a sulfonylamido substituent on the pyridine ring (Alternative 2 of FIG. 1). In addition, urea derivatives can be prepared from the same intermediate using isocyanates. If R=COOMe, carboxamides can be prepared, e.g. by ester-amide exchange or other methods well known to the skilled person.

The substituted benzo-1,3-thiazole derivative can be prepared by standard transformations (e.g. Sandmeyer reaction) of the corresponding 2-aminomethoxybenzo-1,3-thiazole.

Step 1 of FIG. 1

5-(5-methoxybenzo[d]thiazol-2-yl)pyridin-3-amine

5-Methoxybenzothiazole (6.34 g, 38.4 mmol), 3-amino-5-bromopyridine (7.41 g, 42.8 mmol), cesium carbonate (12.5 g, 38.4 mmol), copper(I)bromide (1.12 g) and Pd(OAc)$_2$ (0.56 g, 2.50 mmol) were suspended in dry DMF (200 ml) under argon. P(t-Bu)$_3$ (1.00 g, 4.94 mmol) dissolved in 10 ml dry DMF was added. The reaction mixture was heated at 150° C. for 1.5 hrs, cooled to room temperature and poured into EtOAc (100 ml). The organic phase was washed with water (100 ml) and the aqueous phase extracted with EtOAc (2×100 ml). The combined organic phase was washed with water, dried (MgSO$_4$), filtered and concentrated. Flash chromatography (Heptane:EtOAc 80:20—50:50—EtOAc) afforded 4.09 g (41%) of the title compound as a pale yellow solid.

$^1$H NMR (300 MHz, DMSO-d$_6$) δ 8.39 (s, 1H), 8.08 (s, 1H), 8.01 (d, J=8.8, 1H), 7.73-7.49 (m, 2H), 7.11 (dd, J=8.8, 2.5, 1H), 5.71 (s, 2H), 3.87 (s, 3H). MS (pos): 258 (M+H)

Likewise the following compound was prepared:

5-(5-Fluorobenzo[d]thiazol-2-yl)pyridin-3-amine $^1$H NMR (300 MHz, DMSO-d$_6$) δ 8.41 (s, 1H), 8.21 (dd, J=8.9, 5.3, 2H), 8.16-7.95 (m, 1H), 7.92 (dd, J=9.9, 2.5, 1H), 7.59 (s, 1H), 7.39 (td, J=9.1, 2.6, 1H), 5.73 (s, 2H)

Step 2 (Alternative 1) of FIG. 1. Acetylation of benzo[d]thiazol-2-yl pyridin-3-amine Derivatives N-(5-(5-Methoxybenzo[d]thiazol-2-yl)pyridin-3-yl) acetamide (4-93)

To a suspension of 5-(5-methoxybenzo[d]thiazol-2-yl) pyridin-3-amine (1.29 g, 5.00 mmol) in DCM (25 ml) was added pyridine (10 ml), followed by acetic anhydride (0.95 ml, 10.0 mmol). The reaction mixture was stirred at room temperature overnight, poured into water (100 ml) and the aqueous phase extracted with CHCl$_3$:MeOH (90:10) (3×100 ml). The combined organic extract was dried (Na$_2$SO$_4$), filtered and concentrated. The crude material was treated with EtOAc (75 ml), sonicated for 2 minutes and filtered. Drying allowed the isolation of 1.30 gram (73%) of the title compound as a beige solid from 1.54 g substrate.

¹H NMR (400 MHz, DMSO-d₆) δ 10.41 (s, 1H), 8.88 (s, 1H), 8.80 (s, 2H), 8.03 (d, J=8.8, 1H), 7.66 (d, J=2.3, 1H), 7.13 (dd, J=8.8, 2.4, 1H), 3.87 (s, 3H), 2.13 (s, 3H).

MS (pos): 322 (M+Na).

Likewise the following compound was prepared:

N-(5-(5-fluorobenzo[d]thiazol-2-yl)pyridin-3-yl) acetamide (5-23)

¹H NMR (400 MHz, DMSO-d₆) δ 10.43 (s, 1H), 8.91 (s, 1H), 8.88-8.74 (m, 2H), 8.24 (dd, J=8.9, 5.3, 1H), 7.97 (dd, J=9.8, 2.5, 1H), 7.42 (td, J=9.0, 2.6, 1H), 2.13 (s, 3H).

MS (neg): 285.9 (M−H).

Step 2 (Alternative 2) of FIG. 1. Alkylsulfonylation of benzo[d]thiazol-2-yl pyridin-3-amine Derivatives N-(5-(5-Methoxybenzo[d]thiazol-2-yl)pyridin-3-yl) methanesulfonamide (4-95)

To a suspension of 5-(5-methoxybenzo[d]thiazol-2-yl) pyridin-3-amine (0.77 g, 3.00 mmol) in DCM (15 ml) and pyridine (5 ml) was added methanesulfonyl chloride (0.28 ml, 3.60 mmol) at 0° C. The reaction mixture was allowed to reach room temperature and stirred overnight. The solvents were removed on the rotary evaporator and the residue redissolved in EtOAc:MeOH (80:20) (100 ml). The organic phase was washed with water and the aqueous layer extracted twice with EtOAc:MeOH (80:20) (2×100 ml). The combined organic extract was washed with brine (100 ml), dried (MgSO₄), filtered and concentrated. The residue was suspended in EtOAc (75 ml), sonicated for two minutes and filtered. Drying allowed the isolation of 0.89 gram (89%) of the title compound as a beige solid.

¹H NMR (400 MHz, DMSO-d₆) δ 10.33 (s, 1H), 8.95 (s, 1H), 8.57 (d, J=2.3, 1H), 8.27 (s, 1H), 8.06 (d, J=8.8, 1H), 7.68 (d, J=2.3, 1H), 7.15 (dd, J=8.8, 2.3, 1H), 3.88 (s, 3H), 3.16 (s, 3H).

MS (pos): 358 (M+Na).

HPLC (230 nm): 98.3% (area-%).

Likewise the following compound was prepared:

N-(5-(5-fluorobenzo[d]thiazol-2-yl)pyridin-3-yl) methanesulfonamide (5-25)

¹H NMR (400 MHz, DMSO-d₆) δ 10.34 (s, 1H), 8.97 (d, J=1.7, 1H), 8.60 (d, J=2.4, 1H), 8.29 (t, J=2.2, 1H), 8.26 (dd, J=8.9, 5.3, 1H), 8.00 (dd, J=9.8, 2.5, 1H), 7.44 (td, J=9.0, 2.5, 1H), 3.16 (s, 3H).

MS (neg): 322 (M−H).

N-(5-(5-Hydroxybenzo[d]thiazol-2-yl)pyridin-3-yl) methanesulfonamide (4-99)

To a suspension of N-(5-(5-methoxybenzo[d]thiazol-2-yl) pyridin-3-yl)methane-sulfonamide (0.52 g, 1.55 mmol) in DCM (20 ml) was added BBr₃ (2 ml, 20.8 mmol) at 0° C. The reaction mixture was allowed to reach room temperature and stirred overnight. To the reaction mixture was carefully added saturated NaHCO₃ (aq) and the aqueous phase was extracted with EtOAc:MeOH (90:10) (3×100 ml). The combined organic extract was dried (MgSO₄), filtered, concentrated and subjected to dry flash chromatography (heptane:EtOAc 50:50—EtOAc) to afford a 250 mg. HPLC and NMR showed presence of remaining starting material (identical R_f-values on TLC). Preparative HPLC allowed isolation of 100 mg of the title compound as a colourless solid.

¹H NMR (300 MHz, DMSO-d₆) δ 9.95 (bs, 1H), 8.84 (d, J=1.9, 1H), 8.50 (d, J=2.5, 1H), 8.28-8.14 (m, 1H), 7.94 (d, J=8.7, 1H), 7.42 (d, J=2.2, 1H), 7.01 (dd, J=8.7, 2.4, 1H), 3.08 (s, 3H).

MS (pos): 344 (M+Na).

MS (neg): 320 (M−H).

Step 2 (Alternative 3) of FIG. 1. Aminocarbonylation of benzo[d]thiazol-2-yl)pyridin-3-amine Derivatives 1-(5-(5-Methoxybenzo[d]thiazol-2-yl)pyridin-3-yl) urea (5-85)

To a suspension of 5-(5-methoxybenzo[d]thiazol-2-yl) pyridin-3-amine (256 mg, 0.99 mmol) in acetonitrile (20 ml) was added chlorosulfonyl isocyanate (98 μl) and the reaction mixture heated at 80° C. overnight. After cooling to room temperature, the reaction mixture was quenched with water, filtered and the precipitated material washed with methanol to afford 210 mg (70%) of the title compound as a yellow solid.

¹H NMR (400 MHz, DMSO) δ 9.32 (s, 1H), 9.04-8.66 (m, 2H), 8.07 (d, J=8.9, 1H), 7.68 (d, J=2.5, 1H), 7.16 (dd, J=8.9, 2.5, 1H), 3.88 (s, 3H).

In a second synthetic scheme benzothiazolylpyridines with a carbon-substituted pyridine ring can be prepared. The different benzothiazolylbromopyridines can conveniently be prepared using a palladium catalysed coupling of a substituted benzo-1,3-thiazole and a dibromopyridine derivative as shown in the scheme below. The different benzothiazolylbromopyridines can then be further functionalised through coupling methods (e.g. Shonogashira and Heck couplings) well known to the skilled person. The resulting products can then be further transformed to other derivatives using standard synthetic reactions (e.g. hydrogenation).

Another series of benzothiazolylpyridines presented in Table 4 are available from benzothiazolylformylpyridines as shown in the Scheme of FIG. 2. The formyl group can be further modified by reduction to the corresponding alcohol or to amine derivatives through reductive emanation using suitable amines.

2-(5-bromopyridin-3-yl)-5-methoxybenzo[d]thiazole

A mixture of 5-methoxybenzo[d]thiazole (4.02 g, 24.3 mmol) 3,5-dibromopyridine (9.52 g, 29.2 mmol), palladium (II)acetate (56.5 mg, 0.25 mmol), triphenylphosphine (3.20 g, 12.2 mmol), Cu(OAc)₂.H₂O (0.9722 g, 4.87 mmol) and potassium carbonate (6.6928 g, 48.4 mmol) in toluene (70 ml) was refluxed open to air for 21.5 hrs. The reaction mixture was cooled to room temperature, filtered and concentrated under reduced pressure. Dry-flash chromatography on silica gel (500 g) eluting with heptane—heptane (90:10) afforded 5.36 g of the impure title compound as a yellow solid.

¹H NMR (400 MHz, CDCl₃) δ 9.12 (d, J=1.9, 1H), 8.74 (d, J=2.2, 1H), 8.51 (t, J=2.1, 1H), 7.76 (d, J=8.8, 1H), 7.56 (d, J=2.5, 1H), 7.08 (dd, J=8.8, 2.5, 1H), 3.90 (s, 3H).

(E)-3-(5-(5-methoxybenzo[d]thiazol-2-yl)pyridin-3-yl)acrylamide (5-51)

A mixture of 2-(5-bromopyridin-3-yl)-5-methoxybenzo [d]thiazole (2.01 g, 6.25 mmol), DIPEA (3.8 ml, 21.8 mmol), Pd(OAc)₂ (71.3 mg, 0.32 mmol), Pd(oTol)₃ (0.6273 g, 2.06 mmol) and acrylamide (8.87 g, 124.8 mmol) in dry DMF (50 ml) was flushed with argon, capped and stirred at 120° C. for 2.5 hrs. The reaction mixture was cooled to room temperature and placed in the freezer overnight. The cooled reaction mixture was filtered and the collected solid was washed with methanol (20 ml) and dried under reduced pressure to afford 1.66 g (85%) of the title compound as a colorless solid.

$^1$H NMR (400 MHz, DMSO-d₆) δ 9.19 (d, J=1.9, 1H), 8.92 (d, J=1.7, 1H), 8.56 (m, 1H), 8.08 (d, J=8.8, 1H), 7.65 (d, J=2.4, 1H), 7.63 (bs, 1H), 7.57 (d, J=16.0, 1H), 7.28 (bs, 1H), 7.16 (dd, J=8.8, 2.4, 1H), 6.92 (d, J=16.0, 1H), 3.88 (s, 3H).

MS (pos): 334 (M+Na), 645 (2M+Na)

3-(5-(5-Methoxybenzo[d]thiazol-2-yl)pyridin-3-yl)propanamide (1-17)

To a solution of (E)-3-(5-(5-methoxybenzo[d]thiazol-2-yl)pyridin-3-yl)acrylamide (1.08 g, 3.47 mmol) in DMF (40 ml) and MeOH (40 ml) was added Pd(C) (1 g) and the mixture hydrogenated overnight at room temperature by use of a balloon. The reaction mixture was filtered and concentrated and the residue triturated with EtOAc, filtered and dried to afford 108 mg of the title compound as a beige solid.

$^1$H NMR (400 MHz, DMSO) δ 9.06 (d, J=2.1, 1H), 8.61 (d, J=2.0, 1H), 8.26 (t, J=2.1, 1H), 8.06 (d, J=8.8, 1H), 7.65 (d, J=2.4, 1H), 7.34 (s, 1H), 7.14 (dd, J=8.8, 2.5, 1H), 6.82 (s, 1H), 3.88 (s, 3H), 2.95 (t, J=7.4, 2H), 2.47 (t, J=7.4, 2H).

3-(5-(5-Methoxybenzo[d]thiazol-2-yl)pyridin-3-yl)propiolamide (1-19)

To a mixture of 2-(5-bromopyridin-3-yl)-5-methoxybenzo[d]thiazole (500 mg, 1.56 mmol), CuI (50 mg), CsCO₃ (500 mg, 1.56 mmol) and propiolamide (550 mg, 8 mmol) was added DMF (25 ml) followed by bis(triphenylphosphine)palladium (II) chloride (50 mg) under argon. The reaction mixture was heated to 80° C. for 2.5 hrs. After cooling, water and EtOAc were added. The aqueous phase was extracted with EtOAc (×2), dried (Na₂SO₄), filtered and concentrated. Flash chromatography (Heptane:EtOAc 70:30—EtOAc) afforded 400 mg of the product as a yellow solid.

$^1$H NMR (400 MHz, DMSO) δ 9.31 (d, J=2.0, 1H), 8.90 (d, J=1.7, 1H), 8.56 (t, J=2.1, 1H), 8.29 (s, 1H), 8.09 (d, J=8.9, 1H), 7.83 (s, 1H), 7.66 (d, J=2.5, 1H), 7.17 (dd, J=8.9, 2.5, 1H), 3.89 (s, 3H).

5-(5-methoxybenzo[d]thiazol-2-yl)nicotinaldehyde

A mixture of 5-methoxybenzo[d]thiazole (0.90 g, 5.40 mmol), 5-bromo-3-pyridinecarboxaldehyde (1.25 g, 6.72 mmol), Pd(OAc)₂ (15 mg), PPh₃ (0.70 g, 2.66 mmol), Cu(OAc)₂ (210 mg) and potassium carbonate (1.50 g, 10.8 mmol) in toluene (20 ml) were heated to reflux overnight. Water and EtOAc were added and the reaction mixture filtered. The aqueous phase was extracted with EtOAc (×2), the organic extract dried (Na₂SO₄), filtered and concentrated. Flash chromatography (heptane:EtOAc 70:30) afforded 0.70 g of the title compound as a yellow solid.

(5-(5-Methoxybenzo[d]thiazol-2-yl)pyridin-3-yl)methanol (1-27)

To a suspension of 5-(5-methoxybenzo[d]thiazol-2-yl)nicotinaldehyde (135 mg, 0.50 mmol) in NH₃ (MeOH, 7 M, 5 ml) was added sodium borohydride (21 mg, 0.56 mmol). The reaction mixture was stirred at room temperature overnight. The reaction mixture was filtered and the precipitated product washed with water and dried to afford 130 mg (96%) of the title compound as a beige solid.

$^1$H NMR (400 MHz, MeOD) δ 9.18 (s, 1H), 8.70 (s, 1H), 8.46 (s, 1H), 7.91 (d, J=8.9, 1H), 7.60 (d, J=2.4, 1H), 7.13 (dd, J=8.9, 2.5, 1H), 4.78 (s, 2H), 3.92 (s, 3H).

N-((5-(5-Methoxybenzo[d]thiazol-2-yl)pyridin-3-yl)methyl)propan-2-amine (1-29)

To a suspension of 5-(5-methoxybenzo[d]thiazol-2-yl)nicotinaldehyde (135 mg, 0.50 mmol) in MeOH (5 ml) was added isopropylamine (50 μl) and the reaction mixture heated at 80° C. for one hour. The reaction mixture was concentrated and the residue redissolved in MeOH (5 ml) followed by addition of sodium borohydride (21 mg, 0.56 mmol). The reaction mixture was stirred at room temperature for 2 hours and quenched by addition of water. Extraction with EtOAc (×3), drying (Na₂SO₄), filtration and concentration followed by DFC (EtOAc—EtOAc:MeOH) afforded 43 mg of the title compound as a beige solid.

$^1$H NMR (400 MHz, MeOD) δ 9.15 (s, 1H), 8.68 (s, 1H), 8.49 (t, J=2.0, 1H), 7.91 (d, J=8.9, 1H), 7.60 (d, J=2.4, 1H), 7.14 (dd, J=8.9, 2.5, 1H), 3.92 (d, J=1.5, 4H), 2.90 (dt, J=12.6, 6.3, 1H), 1.16 (d, J=6.3, 6H).

1-(5-(5-Methoxybenzo[d]thiazol-2-yl)pyridin-3-yl)-N-methylmethanamine (1-31)

To a suspension of 5-(5-methoxybenzo[d]thiazol-2-yl)nicotinaldehyde (100 mg, 0.37 mmol) in MeOH (5 ml) was added methylamine (5 ml, 41% in water) and the reaction mixture heated at 80° C. for one hour. The reaction mixture was concentrated and the residue redissolved in MeOH (5 ml) followed by addition of sodium borohydride (21 mg, 0.56 mmol). The reaction mixture was stirred at room temperature for 2 hours and quenched by addition of water. Extraction with EtOAc (×3), drying (Na₂SO₄), filtration and concentration followed by DFC (EtOAc—EtOAc:MeOH) afforded 71 mg of the title compound as a beige solid.

$^1$H NMR (400 MHz, MeOD) δ 9.16 (d, J=1.8, 1H), 8.66 (d, J=1.5, 1H), 8.47 (t, J=2.0, 1H), 7.91 (d, J=8.9, 1H), 7.59 (d, J=2.4, 1H), 7.13 (dd, J=8.9, 2.5, 1H), 3.92 (s, 4H), 2.47 (s, 3H), 1.90 (s, 2H).

B. IC$_{50}$ Determination

The principal method utilized is a radioactive filter binding assay using 33P ATP (Hastie, et al 2006. *Nat Protoc.* 2006; 1(2):968-71; Bain, et al2007. *Biochem J.* 2007 Dec. 15; 408(3):297-315). This method is sensitive, accurate and provides a direct measure of activity.

1. The compounds were diluted to the appropriate concentration
2. The compounds were added to a 'mother plate' consisting of samples, controls and blanks. These serve as the source for 'daughter plates' which are stored at −20° C. until assay initiation
3. Protein Kinases: Enzyme/Substrate mixture was added to the compound, and the compounds were incubated for five minutes at Room Temperature (RT).
4. 33P ATP was added to the compounds in order to initiate the assay.
5. Orthophosphoric acid was added to the compounds in order to halt the assay.

6. Assay components were harvested onto P81 filter plates, filter plates were air-dried, scintillation fluid was added to plates, and counts were read on a Topcount NXT. A mean percentage activity was calculated.

Table 5 below shows the measured $IC_{50}$ values (in μM) against DYRK1A for selected inhibitors.

TABLE 5

| Compound | $IC_{50}$ |
|---|---|
| 4-93 | 0.04 |
| 4-95 | 0.26 |
| 4-99 | 0.28 |
| 5-25 | 5.64 |
| 5-23 | 3.68 |
| 5-85 | 0.056 |
| 5-51 | 0.145 |
| 1-19 | 0.153 |
| 1-31 | 0.065 |
| 1-29 | 0.375 |
| 1-27 | 0.208 |
| 1-17 | 0.162 |

C. Kinase Profile of Benzothiazolylpyridine Derivatives

The determination of protein kinase inhibition was performed at the International Centre for Kinase Profiling at the University of Dundee, UK. The method used is a radioactive filter binding assay using $^{33}P$ ATP as described in the literature (Hastie, C. J.; McLauchlan, H. J.; Cohen, P. Assay of Protein Kinases Using Radiolabeled ATP: a Protocol. *Nat. Protc.* 2006, 1 (2), 968-971). The ATP concentrations were at or below the calculated Km for ATP for each particular kinase.

Table 6 below show the selectivity of protein kinase inhibition measured as percentage inhibition of 138 protein kinases at 1 micromolar inhibitor concentration. The data in relation to DYRK1A is highlighted in bold.

TABLE 6

| Kinase | Compound 4-93 | Compound 4-99 | Kinase | Compound 4-93 | Compound 4-99 |
|---|---|---|---|---|---|
| MKK1 | 0 | 0 | NEK6 | 0 | 0 |
| MKK2 | 25 | 0 | IKKb | 0 | 0 |
| MKK6 | 0 | 0 | IKKe | 0 | 0 |
| ERK1 | 0 | 0 | TBK1 | 0 | 0 |
| ERK2 | 0 | 0 | PIM1 | 2 | 0 |
| ERK5 | 28 | 7 | PIM2 | 0 | 0 |
| JNK1 | 0 | 0 | PIM3 | 7 | 0 |
| JNK2 | 0 | 0 | SRPK1 | 0 | 0 |
| JNK3 | 0 | 0 | EF2K | 0 | 0 |
| p38a MAPK | 0 | 0 | EIF2AK3 | 0 | 0 |
| p38b MAPK | 0 | 0 | HIPK1 | 0 | 0 |
| p38g MAPK | 0 | 0 | HIPK2 | 10 | 0 |
| p38d MAPK | 0 | 0 | HIPK3 | 0 | 0 |
| ERK8 | 11 | 0 | CLK2 | 78 | 44 |
| RSK1 | 1 | 0 | PAK2 | 0 | 0 |
| RSK2 | 0 | 0 | PAK4 | 0 | 0 |
| PDK1 | 0 | 0 | PAK5 | 0 | 0 |
| PKBa | 0 | 0 | PAK6 | 0 | 0 |
| PKBb | 0 | 0 | MST2 | 0 | 0 |
| SGK1 | 0 | 7 | MST3 | 0 | 0 |
| S6K1 | 0 | 0 | MST4 | 0 | 0 |
| PKA | 12 | 3 | GCK | 0 | 0 |
| ROCK 2 | 0 | 0 | MAP4K3 | 0 | 0 |
| PRK2 | 0 | 0 | MAP4K5 | 18 | 0 |
| PKCa | 0 | 0 | MINK1 | 0 | 0 |
| PKCy | 0 | 0 | MEKK1 | 0 | 0 |
| PKCz | 0 | 0 | MLK1 | 0 | 0 |

TABLE 6-continued

| Kinase | Compound 4-93 | Compound 4-99 | Kinase | Compound 4-93 | Compound 4-99 |
|---|---|---|---|---|---|
| PKD1 | 0 | 0 | MLK3 | 0 | 0 |
| STK33 | 0 | 0 | TESK1 | 0 | 0 |
| MSK1 | 0 | 0 | TAO1 | 0 | 0 |
| MNK1 | 0 | 0 | ASK1 | 0 | 0 |
| MNK2 | 0 | 0 | TAK1 | 52 | 8 |
| MAPKAP-K2 | 0 | 0 | IRAK1 | 0 | 0 |
| MAPKAP-K3 | 0 | 0 | IRAK4 | 12 | 8 |
| PRAK | 0 | 0 | RIPK2 | 0 | 24 |
| CAMKKb | 0 | 0 | OSR1 | 0 | 0 |
| CAMK1 | 0 | 0 | TTK | 12 | 0 |
| SmMLCK | 0 | 0 | MPSK1 | 0 | 11 |
| PHK | 0 | 0 | WNK1 | 0 | 0 |
| DAPK1 | 0 | 0 | ULK1 | 0 | 0 |
| CHK1 | 0 | 0 | ULK2 | 0 | 0 |
| CHK2 | 0 | 0 | TGFBR1 | 0 | 0 |
| GSK3b | 0 | 0 | Src | 0 | 0 |
| CDK2-Cyclin A | 0 | 6 | Lck | 7 | 0 |
| CDK9-Cyclin T1 | 0 | 0 | CSK | 0 | 0 |
| PLK1 | 0 | 0 | YES1 | 0 | 0 |
| Aurora A | 0 | 0 | ABL | 3 | 0 |
| Aurora B | 0 | 0 | BTK | 8 | 0 |
| TLK1 | 0 | 0 | JAK2 | 0 | 0 |
| LKB1 | 0 | 0 | SYK | 0 | 0 |
| AMPK (hum) | 1 | 0 | ZAP70 | 0 | 0 |
| MARK1 | 0 | 0 | TIE2 | 0 | 3 |
| MARK2 | 0 | 0 | BRK | 0 | 0 |
| MARK3 | 1 | 0 | EPH-A2 | 0 | 0 |
| MARK4 | 0 | 0 | EPH-A4 | 0 | 0 |
| BRSK1 | 0 | 0 | EPH-B1 | 0 | 0 |
| BRSK2 | 0 | 0 | EPH-B2 | 0 | 0 |
| MELK | 1 | 0 | EPH-B3 | 0 | 2 |
| NUAK1 | 0 | 0 | EPH-B4 | 0 | 0 |
| SIK2 | 0 | 0 | FGF-R1 | 0 | 0 |
| SIK3 | 0 | 0 | HER4 | 0 | 0 |
| TSSK1 | 0 | 0 | IGF-1R | 0 | 0 |
| CK1y2 | 0 | 0 | IR | 0 | 0 |
| CK1δ | 1 | 8 | IRR | 0 | 0 |
| CK2 | 0 | 6 | TrkA | 0 | 0 |
| TTBK1 | 0 | 0 | DDR2 | 2 | 0 |
| TTBK2 | 0 | 0 | VEG-FR | 0 | 0 |
| DYRK1A | 92 | 58 | PDGFRA | 0 | 0 |
| NEK2a | 0 | 0 | PINK | 0 | 0 |
| NEK6 | 0 | 0 | | | |

4-93 and 4-99 showed protein kinase inhibition that was specific for DYRK1A. Equivalent compounds without the heterocyclic ring on the right side of the structure do not show the same level of specificity (data not shown). It is noted in Table 6 that no CDK inhibition is seen, unlike the compounds as described by Kassis and co-workers (*Eur. J. Med. Chem.* (2011) 46, pp 5416-34).

D. X-Ray Crystallography Analysis of the Binding of the Benzothiazolylpyridine Derivatives with the DYRK1A Receptor Protein Production and Crystallization DYRK1A comprising the kinase domain (DYRK1A, residues 126-490) was produced in bacteria as a HIS-tagged fusion protein and purified as described in detail by Alexeeva et al. (*Acta Crystallogr. D Biol. Crystallogr.* 2015, 71 (Pt 5), 1207-1215).

Co-crystallization with the inhibitors followed the protocol described by Alexeeva et al. The kinase DYRK1A was concentrated to 7-10 mg/ml and mixed with inhibitor solutions in DMSO to achieve an approximately 10-50 fold molar excess of the inhibitors. The crystallization solution (100 mM potassium thiocyanate, 50-100 mM NaCl or KCl, 10-16% PEG 3350) gave octahedron-shaped crystals within 5-7 days at room temperature. Crystals were cryoprotected in crystallization solution modified to include 30% ethylene glycol and were flash-cooled in liquid nitrogen.

Structure Solution and Refinement

X-ray diffraction data were collected at the Helmholz Zentrum Berlin (Berlin Electron Storage Ring Society for Synchrotron BESSY II), Germany and the European Synchrotron Radiation Facility ESRF ID29, Grenoble, France. The images were integrated using the XDSapp software (Krug et al., *J. Appl. Crystallogr.* 2012, 45 (3), 568-572) and XDS (Kabsch, *Acta Crystallogr. D Biol. Crystallogr.* 2010, 66(Pt 2), 125-132). The structures were solved by molecular replacement with Phaser (McCoy et al., *J. Appl. Crystallogr.* 2007, 40 (4), 658-674) using the DYRK1A structure with PDB code 4NCT (Alexeeva et al.) as search model. The structures were refined by iterative cycles of PHENIX (Adams et al., *Acta Crystallogr. D Biol. Crystallogr.* 2010, 66 (Pt 2), 213-221) and the CCP4 (Winn et al., *Acta Ctystallogr. D Biol. Ctystallogr.* 2011, 67 (Pt 4), 235-242) program REFMAC5 (Murshudov et al., *Acta Ctystallogr. D Biol. Ctystallogr.* 2011, 67 (Pt 4), 355-367) followed by the manual refitting of residues and inhibitors into the electron-density between the refinement cycles and placement of water molecules using Coot v.0.7.2. PRODRG (Schuttelkopf et al., *Acta Ctystallogr. D Biol. Crystallogr.* 2004, 60(Pt 8), 1355-1363) was used to generate the cif files for inhibitors.

Results

FIG. 3 shows an interaction between the hydroxyl substituent of the benzothiazole part of 4-99 and leucine 241 of the DYRK1A receptor, a surprising sulphur-π interaction between the heterocyclic sulphur atom of the benzothiazole and phenylalanine 238 and an interaction between the pyridine ring and lysine 188. It is thought that the heterocyclic ring leads to a highly conserved interaction of 4-99 within the DYRK1A receptor and also a more favourable sulphur-π interaction (the phenylalanine 238 acts as a gatekeeper residue in this receptor). This may explain why the compounds of the invention are specific towards the DYRK1A kinase compared to other kinases.

E. Effects of N-(5-(5-Methoxybenzo[d]thiazol-2-yl)pyridin-3-yl)acetamide (4-93) on on Induced Human Pluripotent Stem Cells from Normal and Down Syndrome (DS) Individuals Individuals with DS/Trisomy 21 (TS21) have a very high incidence of Alzheimer's disease (AD) that is attributed in part to an extra copy of the gene encoding amyloid precursor protein (APP). Candidate genes in the DS critical region of chromosome 21 that also contribute to the risk of dementia include the gene encoding dual specificity tyrosine phosphorylation-regulated kinase DYRK1A, a kinase that phosphorylates tau/MAPT.

DYRK1A has been shown to phosphorylate tau at several sites that are hyperphosphorylated in Alzheimer's disease brain and thus elevated expression of DYRK1A in DS may contribute to disease pathology.

DYRK1A has been shown to phosphorylate tau/MAPT at several sites that are hyperphosphorylated in adult DS brains. In previous studies, an extra copy of DYRK1A in DS transgenic mouse brain or COS7 cells over-expressing DYRK1A also resulted in increased tau phosphorylation at a number of sites including serine (Ser) 202, threonine (Thr) 205, Thr 212, Ser 396 and Ser 404, but not at Ser 214. Overexpression of DYRK1A in DS is thought to account for increased tau phosphorylation by GSK3β and the increase in DYRK1A positive neurofibrillary tangles (NFTs) in the brains of people with DS and AD. Therefore therapeutic inhibition of DYRK1A activity in DS and AD may delay the progression of neurodegeneration in DS and AD. The following experiment on reduction of tau phosphorylation by inhibition of DYRK1A by inhibitor 4-93 was performed as described in the literature (Shi, Y. et al. A human stem cell model of early Alzheimer's disease pathology in Down syndrome. *Sci. Transl. Med.* 4, 124ra29 (2012)).

DYRK1A Inhibitors Reduce Tau Phosphorylation at S396 and S404 in Human TS21 Neurons Neuronal cultures at day 40 were treated with DYRK1A inhibitors and control compounds for 10 days. Total protein was extracted and total tau and phosphorylated tau/MAPT was quantified by Western blotting using antibodies to total tau and a number of phospho-tau epitopes.

In control neurons DAPT treatment increased tau/MAPT phosphorylation at Ser 396 and Ser 404, consistent with its effects on promoting neurogenesis. Treatment of control neurons with 4-93 gave a slight increase in tau/MAPT phosphorylation at pSer 396 and pSer 404 compared to DMSO treated controls. Increasing tau phosphorylation is consistent with compounds known to increase neuronal numbers, such as DAPT and EGCG (FIG. 4).

In TS21 neuronal cultures, DAPT treatment increased total tau protein levels and tau phosphorylation at Ser 396 and Ser 404, sites that are hyperphosphorylated by DYRK1A in DS. Treatment of neuronal cultures with inhibitor 4-93 gave a striking reduction in tau/MAPT phosphorylation at sites that are highly phosphorylated in TS21 neurons and in Alzheimer's disease brain. Inhibitor 4-93 at non-toxic concentrations significantly reduced tau phosphorylation at Ser 396 and Ser 404 in TS21 neurons (FIG. 5).

When normalised to total tau levels (FIGS. 6 and 7), levels of phosphorylated tau/MAPT in TS21 neurons at Ser 396 and Ser 404 were significantly lower than DMSO treated controls or DAPT treated positive controls suggesting that the decrease in phosphorylated tau is not simply a result of decreases in total tau protein levels (FIGS. 7B and C). Phosphorylation of Ser 214, a site reported not to be phosphorylated by DYRK1A, was unaffected by DYRK1A inhibition (FIG. 7A), increasing evidence in support of the reduced phosphorylation at Ser 396 and Ser 404 being specific to this DYRK1A inhibition by inhibitor 4-93.

Conclusion

DYRK1A has been shown to phosphorylate tau/MAPT at several sites, including Ser 396 and Ser 404, which are significantly hyperphosphorylated in adult DS brains. Inhibitor 4-93 significantly reduces tau phosphorylation in TS21 neurons at these sites, but do not affect phosphorylation at Ser 214, a site reported not to be phosphorylated by DYRK1A. DYRK1A inhibitors are effective in reducing tau/MAPT phosphorylation on at least two sites that contribute to tau pathology.

Example B

A. Preparation of Further Compounds of Formula (I)

The following compounds in Table 7 were prepared using the methodology set out below.

TABLE 7

| Compound Name | Structure |
|---|---|
| PST-288 | 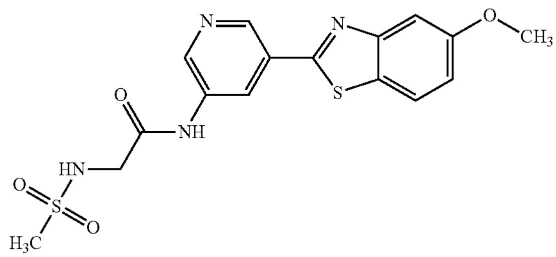 [SMILES: COc1ccc2sc(-c3cncc(NC(=O)CNS(C)(=O)=O)c3)nc2c1] |
| PST-206 | 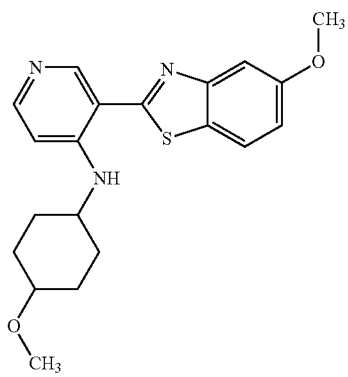 [SMILES: COc1ccc2sc(-c3cnccc3NC3CCC(OC)CC3)nc2c1] |
| PST-201 | 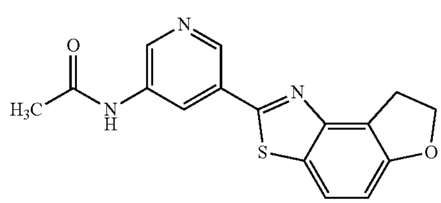 [SMILES: CC(=O)Nc1cncc(-c2nc3c4c(ccc3s2)OCC4)c1] |
| PST-173 | 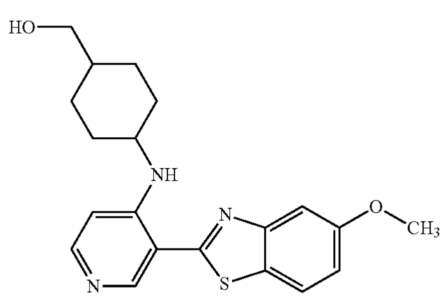 [SMILES: COc1ccc2sc(-c3cnccc3NC3CCC(CO)CC3)nc2c1] |

TABLE 7-continued

| Compound Name | Structure |
|---|---|
| PST-170 | (structure image) |
| PST-169 | (structure image) |
| PST-166 | (structure image) |
| PST-164 | (structure image) |
| PST-163 | (structure image) |
| PST-162 | (structure image) |

TABLE 7-continued

| Compound Name | Structure |
|---|---|
| PST-158 | *structure: 3-(5-methoxybenzothiazol-2-yl)-4-(methanesulfonamido)pyridine* |
| PST-157 | *structure: 4-acetamido-2-methyl-5-(5-methoxybenzothiazol-2-yl)pyridine* |
| PST-156 | *structure: 4-[(1-acetylpiperidin-4-yl)amino]-3-(6-methoxybenzothiazol-2-yl)pyridine* |
| PST-155 | *structure: 4-[(1-methanesulfonylpiperidin-4-yl)amino]-3-(5-methoxybenzothiazol-2-yl)pyridine* |
| PST-154 | *structure: methyl 5-(5-methoxybenzothiazol-2-yl)pyridine-2-carboxylate* |
| PST-151 | *structure: 4-[(1-carbamoylpiperidin-4-yl)amino]-3-(5-methoxybenzothiazol-2-yl)pyridine* |

TABLE 7-continued

| Compound Name | Structure |
| --- | --- |
| PST-150 | 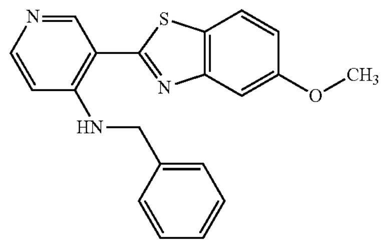 [SMILES: COc1ccc2sc(-c3cnccc3NCc3ccccc3)nc2c1] |
| PST-148 | 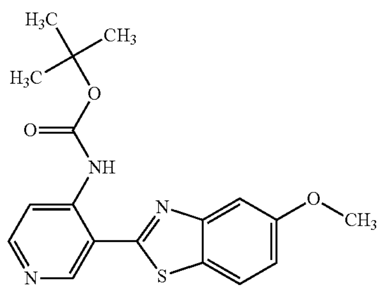 [SMILES: COc1ccc2sc(-c3cnccc3NC(=O)OC(C)(C)C)nc2c1] |
| PST-147 | 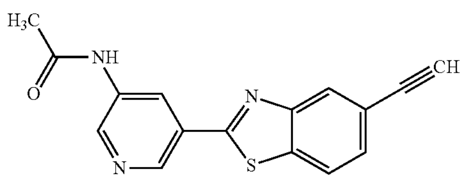 [SMILES: C#Cc1ccc2sc(-c3cncc(NC(C)=O)c3)nc2c1] |
| PST-141 | 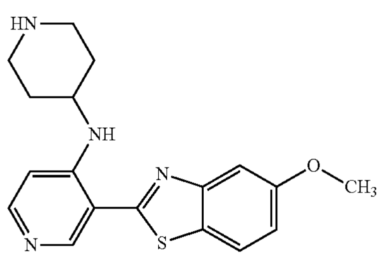 [SMILES: COc1ccc2sc(-c3cnccc3NC3CCNCC3)nc2c1] |
| PST-134 | 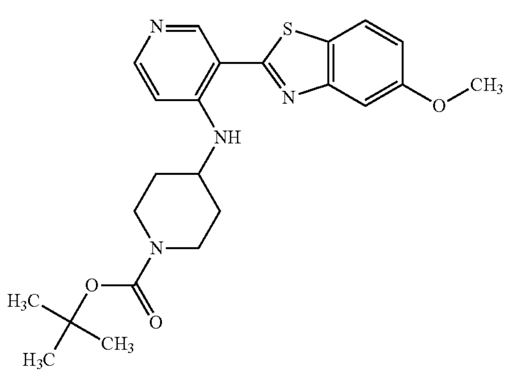 [SMILES: COc1ccc2sc(-c3cnccc3NC3CCN(C(=O)OC(C)(C)C)CC3)nc2c1] |

TABLE 7-continued
| Compound Name | Structure |
|---|---|
| PST-131 | 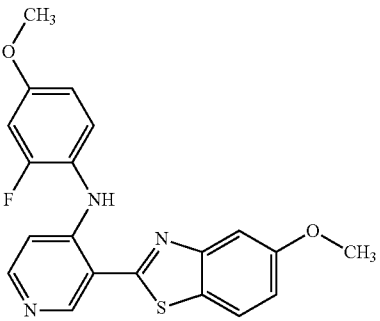 [SMILES: COc1ccc(Nc2ccncc2-c2nc3cc(OC)ccc3s2)c(F)c1] |
| PST-129 | 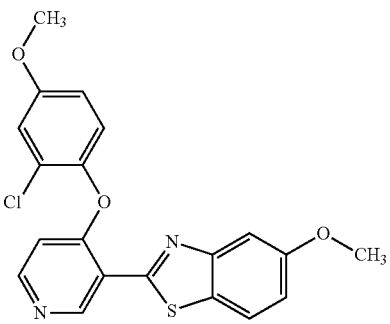 [SMILES: COc1ccc(Oc2ccncc2-c2nc3cc(OC)ccc3s2)c(Cl)c1] |
| PST-128 | 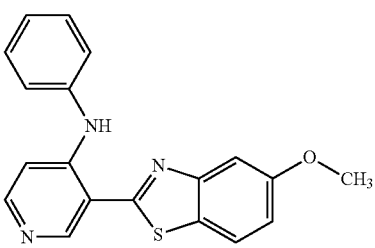 [SMILES: COc1ccc2sc(-c3cnccc3Nc3ccccc3)nc2c1] |
| PST-122 | 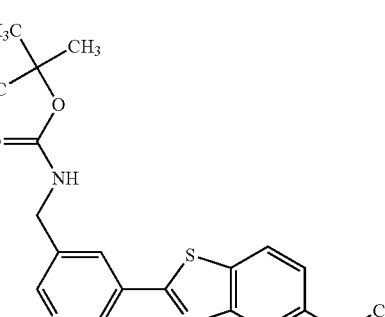 |
| PST-120 | 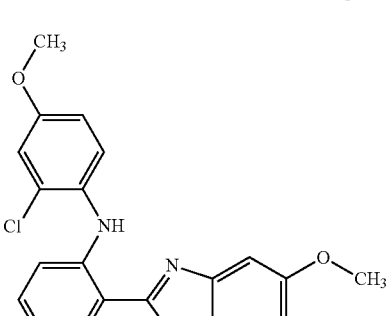 |

TABLE 7-continued

| Compound Name | Structure |
| --- | --- |
| PST-110 | 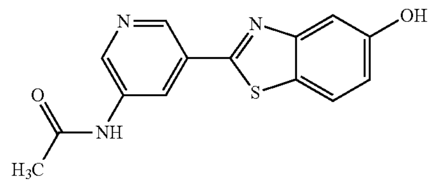 [SMILES: CC(=O)Nc1cncc(-c2nc3cc(O)ccc3s2)c1] |
| PST-098 | 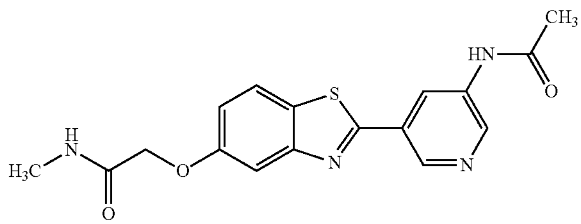 [SMILES: CNC(=O)COc1ccc2sc(-c3cncc(NC(C)=O)c3)nc2c1] |
| PST-097 | 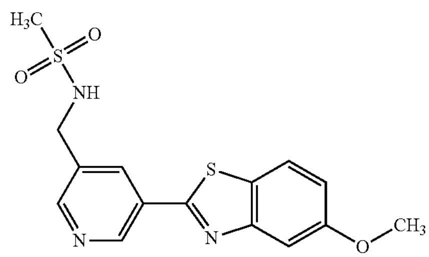 [SMILES: COc1ccc2sc(-c3cncc(CNS(C)(=O)=O)c3)nc2c1] |
| PST-096 | 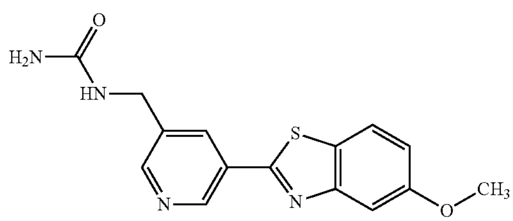 [SMILES: COc1ccc2sc(-c3cncc(CNC(N)=O)c3)nc2c1] |
| PST-095 | 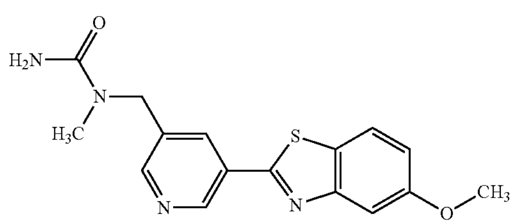 [SMILES: COc1ccc2sc(-c3cncc(CN(C)C(N)=O)c3)nc2c1] |
| PST-087 | 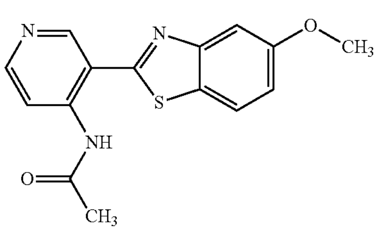 [SMILES: COc1ccc2sc(-c3cnccc3NC(C)=O)nc2c1] |
| PST-082 | 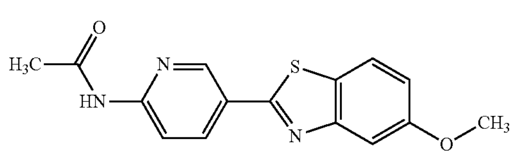 [SMILES: COc1ccc2sc(-c3ccc(NC(C)=O)nc3)nc2c1] |

TABLE 7-continued
| Compound Name | Structure |
| --- | --- |
| PST-077 | 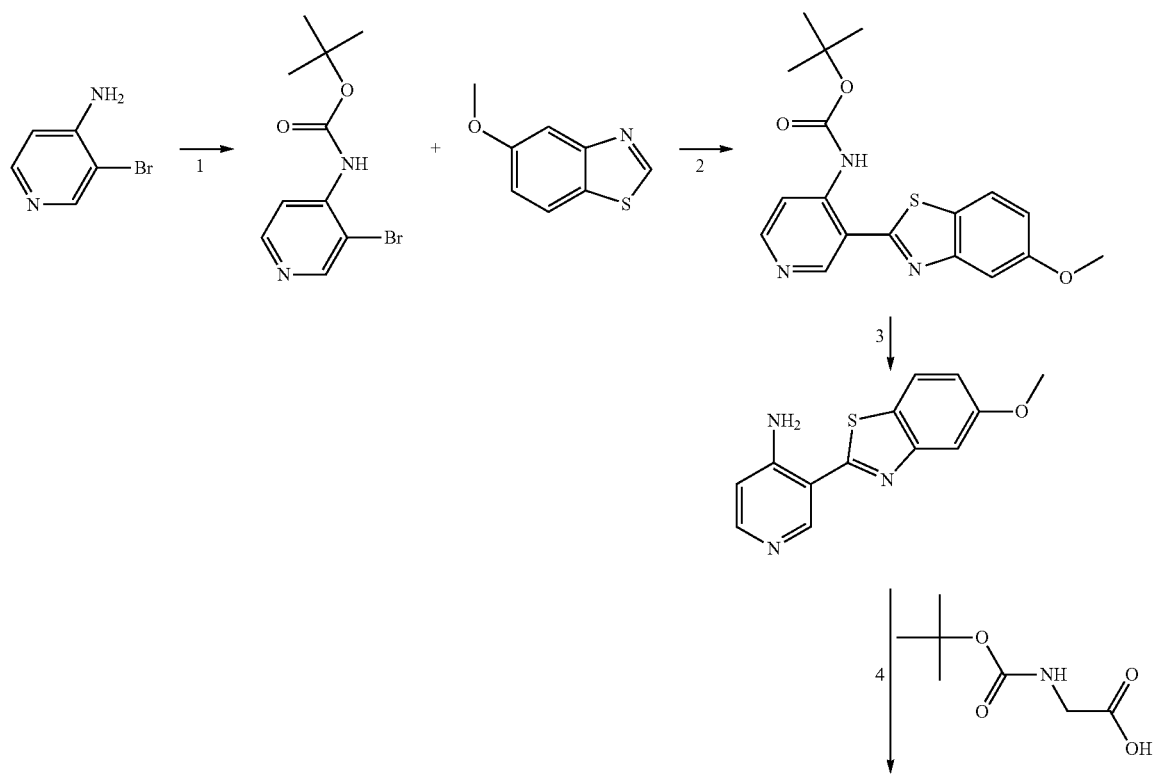 |
| PST-076 | 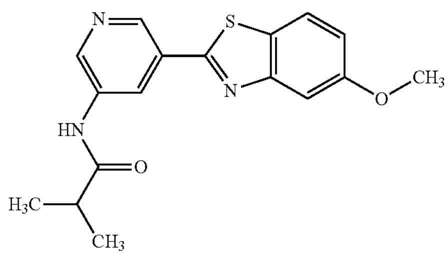 [SMILES: COc1ccc2sc(-c3cncc(NC(=O)C(C)C)c3)nc2c1] |
| PST-075 | 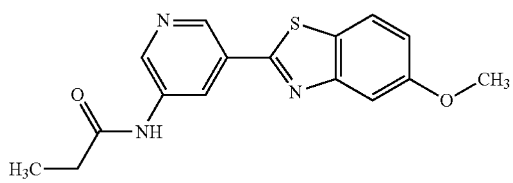 [SMILES: CCC(=O)Nc1cncc(-c2nc3cc(OC)ccc3s2)c1] |
Scheme-1

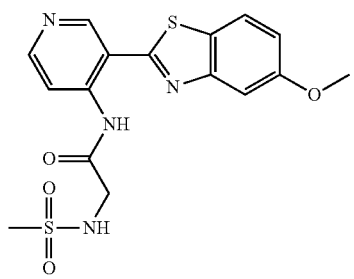 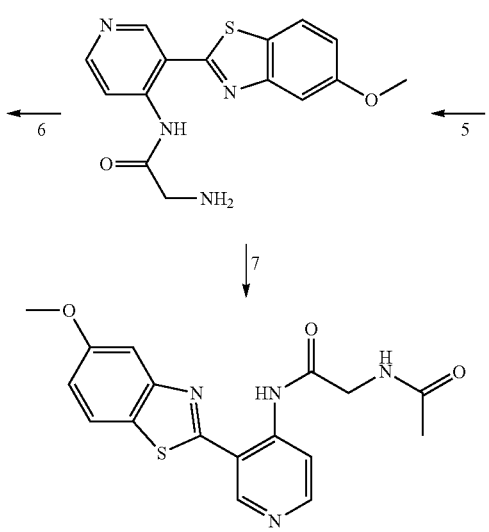 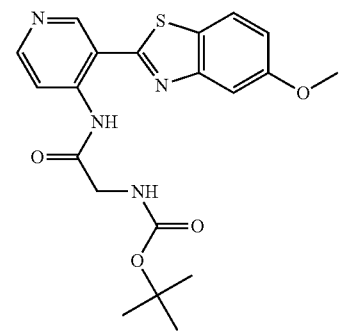

Example 1A 2-amino-N-(3-(5-methoxybenzo[d]thiazol-2-yl)pyridin-4-yl)acetamide hydrochloride (PST-163)

Step 1 Tert-butyl (3-bromopyridin-4-yl)carbamate

To stirred a solution of 4-amino 3-bromo pyridine (10.0 g, 57.803 mmol) in THF (500 ml) were added triethylamine (8.8 g, 86.705 mmol) and Boc anhydride (37.89 g, 173.410 mmol). The reaction mixture was stirred for 2 h, before pouring into water (700 ml) and extracted with EtOAc (500 ml×2), yielding tert-butyl (3-bromopyridin-4-yl)carbamate (37.0 g, 136.029 mmol). MS: 274.95 (M+2).

Step 2 Tert-butyl (3-(5-methoxybenzo[d]thiazol-2-yl)pyridin-4-yl)carbamate

To a stirred solution of 5-methoxybenzo[d]thiazole (5 g, 30.299 mmol) and tert-butyl(3-bromopyridine-4-yl)carbamate (24.7 g, 90.802 mmol) in toluene was added $K_2CO_3$.Cu(I)Br (1.7 g, 11.846 mmol), Pd(OAc)$_2$ (0.8 g, 3.563 mmol) and xantphose (3.5 g, 6.049 mmol) were added to the reaction mixture before heating to 110° C. for 16 h. The resulting reaction mixture was poured in to water (500 ml) and extracted with EtOAc (500 ml). The resulting crude material was purified by column chromatography (20% EtOAc in Hexane) yielding tert-butyl (3-(5-methoxybenzo[d]thiazole-2-yl) pyridine-4-yl) carbamate (PST-148) (2.5 g, 7.002 mmol). MS: ES+ 358 (M+1); 1H NMR (400 MHz, DMSO-d$_6$) δ ppm: 11.68 (s, 1H), 9.03 (s, 1H), 8.54 (d, J=5.6 Hz, 1H), 8.30 (d, J=5.6 Hz, 1H), 8.10 (d, J=9.2 Hz, 1H), 7.50 (d, J=2.4 Hz, 1H), 7.20 (dd, J=8.8, 2.4 Hz, 1H), 3.90 (s, 3H), 1.55 (s, 9H).

Step 3 3-(5-methoxybenzo[d]thiazol-2-yl)pyridin-4-amine

To a stirred solution of tert-butyl (3-(5-methoxybenzo[d]thiazole-2-yl) pyridine-4-yl) carbamate (2.5 g, 7.000 mmol) in dichloromethane (50 ml) was added trifluoro acetic acid (8 gm, 70.156 mmol) and stirred for 16 h. The reaction mixture was concentrated under reduced pressure and the residue was suspended in saturated NaHCO$_3$ solution (60 ml). The basic aqueous phase was extracted with EtOAc (70 ml) and dried yielding 3-(5-methoxybenzo[d]thiazol-2-yl) pyridin-4-amine (1.6 g, 6.223 mmol). MS: ES+ 258.15 (M+1); 1H NMR (400 MHz, DMSO-d$_6$) δ ppm: 9.73 (br s, 1H), 9.36 (br s, 1H), 8.96 (s, 1H), 8.21 (d, J=6.8 Hz, 1H), 8.10 (d, J=8.8 Hz, 1H), 7.72 (d, J=2.8 Hz, 1H), 7.15-7.23 (m, 2H), 3.86 (s, 3H).

Step 4 Tert-butyl (2-((3-(5-methoxybenzo[d]thiazol-2-yl)pyridin-4-yl)amino)-2-oxoethyl)carbamate To stirred a solution of BOC-glycine (CAS No. 4530-20-5) (0.5 g, 2.854 mmol) in THF (25 ml) were added HATU (1.62 g, 4.260 mmol) and DIPEA (1.47 g, 11.382 mmol) and stirred for 45 min. 3-(5-methoxybenzo[d]thiazol-2-yl)pyridin-4-amine (0.4 g, 1.556 mmol) was added in to the reaction mixture and stirred for 16 h. The resulting reaction mixture was poured in to water (100 ml) and extracted with EtOAc (100 ml×2). The resulting crude material was purified by flash chromatography (42% EtOAc in Hexane) yielding tert-butyl (2-((3-(5-methoxybenzo[d]thiazol-2-yl)pyridin-4-yl)amino)-2-oxoethyl)carbamate (0.55 g, 1.328 mmol). MS: ES+ 415.26 (M+1); 1H NMR (400 MHz, DMSO-d$_6$) δ ppm: 12.97 (s, 1H), 9.09 (s, 1H), 8.70 (d, J=6.0 Hz, 1H), 8.60 (d, J=5.6 Hz, 1H), 8.06-8.12 (m, 2H), 7.99 (d, J=2.4 Hz, 1H), 7.23 (dd, J=8.8, 2.4 Hz, 1H), 3.92 (s, 3H), 3.83 (d, J=5.2 Hz, 2H), 1.08 (s, 9H).

Step 5 2-amino-N-(3-(5-methoxybenzo[d]thiazol-2-yl)pyridin-4-yl)acetamide hydrochloride Tert-butyl (2-((3-(5-methoxybenzo[d]thiazol-2-yl)pyridin-4-yl)amino)-2-oxoethyl)carbamate (0.55 g, 1.328 mmol) was stirred in 4 M HCl in 1,4 dioxane (7 ml) for 18 h. The resulting reaction mixture was concentrated under reduced pressure and triturated by hexane (10 ml) yielding 2-amino-N-(3-(5-methoxybenzo[d]thiazol-2-yl)pyridin-4-yl)acetamide hydrochloride (0.48 g, 1.528 mmol). MS: ES+ 314.9 (M+1); 1H NMR (400 MHz, DMSO-d$_6$) δ ppm: 12.50 (s, 1H), 9.21 (s, 1H), 8.72 (d, J=6.0 Hz, 1H), 8.58 (d, J=6.0

Hz, 1H), 8.52 (br S, 2H), 8.14 (d, J=9.2 Hz, 1H), 7.84 (d, J=2.4 Hz, 1H), 7.23 (dd, 8.8, 2.4 Hz, 1H), 4.20 (d, J=4.4 Hz, 2H), 3.91 (s, 3H).

Step-6 N-(3-(5-methoxybenzo[d]thiazol-2-yl)pyridin-4-yl)-2-(methylsulfonamido) acetamide To a stirred solution of 2-amino-N-(3-(5-methoxybenzo[d]thiazol-2-yl)pyridin-4-yl)acetamide hydrochloride (0.2 g, 0.636 mmol) in THF were added $K_2CO_3$ (o.44 g. 3.183 mmol) and mesyl chloride (0.4 g, 3.491 mmol) and stirred for 1 h. The resulting reaction mixture was poured in to water (80 ml) and extracted with EtOAc (50 ml×2). The resulting crude was purified by PREP HPLC yielding N-(3-(5-methoxybenzo[d]thiazol-2-yl)pyridin-4-yl)-2-(methylsulfonamido)acetamide (PST-170) (0.050 g, 0.127 mmol). MS: ES+ 393.14 (M+1); 1H NMR (400 MHz, DMSO-$d_6$) δ ppm: 13.04 (s, 1H), 9.14 (s, 1H), 8.72 (d, J=5.6 Hz, 1H), 8.62 (d, J=5.6 Hz, 1H), 8.21 (t, J=6.4 Hz, 1H), 8.13 (d, J=2.4 Hz, 1H), 8.08 (d, J=8.8 Hz, 1H), 7.17 (dd, J=8.8, 2.8 Hz, 1H), 3.99 (d, J=6.4 Hz, 2H), 3.88 (s, 1H), 3.09 (s, 3H).

Example 1B 2-acetamido-N-(3-(5-methoxybenzo[d]thiazol-2-yl)pyridin-4-yl)acetamide (PST-169)

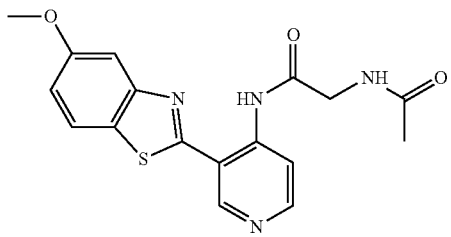 [SMILES: COc1ccc2sc(-c3cnccc3NC(=O)CNC(C)=O)nc2c1]

Step-7 2-acetamido-N-(3-(5-methoxybenzo[d]thiazol-2-yl)pyridin-4-yl)acetamide

To a stirred solution of 2-amino-N-(3-(5-methoxybenzo[d]thiazol-2-yl)pyridin-4-yl)acetamide hydrochloride (the product of step-5 of example 1A) (0.2 g, 0.636 mmol) in pyridine were added DMAP and acetyl chloride (0.25 g, 3.184 mmol) and stirred for 1 h before pouring into water (80 ml) and extracted with EtOAc (50 ml×2). The resulting crude was purified by PREP HPLC yielding 2-acetamido-N-(3-(5-methoxybenzo[d]thiazol-2-yl)pyridin-4-yl)acetamide (PST-169) (0.017 g, 0.047 mmol). MS: ES+ 357.1 (M+1); 1H NMR (400 MHz, DMSO-$d_6$) δ ppm: 12.49 (s, 1H), 9.10 (s, 1H), 9.03 (s, 1H), 8.58-8.67 (m, 2H), 8.10 (d, J=8.8 Hz, 1H), 7.93 (s, 1H), 7.20 (dd, J=8.8, 2.4 Hz, 1H), 4.04 (d, J=5.6 Hz, 2H), 3.92 (s, 3H), 1.92 (s, 3H).

Example 1C

N-(3-(5-methoxybenzo[d]thiazol-2-yl)pyridin-4-yl)methanesulfonamide (PST-158)

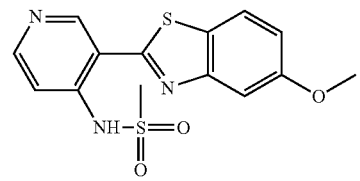 [SMILES: COc1ccc2sc(-c3cnccc3NS(C)(=O)=O)nc2c1]

Step-8 N-(3-(5-methoxybenzo[d]thiazol-2-yl)pyridin-4-yl)methanesulfonamide

To a stirred solution of 3-(5-methoxybenzo[d]thiazol-2-yl)pyridin-4-amine (the product of step-3 of example 1A) (0.2 g, 0.778 mmol) in acetonitrile (10 ml) $K_2CO_3$ (0.645 g, 4.666 mmol) and $MeSO_2Cl$ (0.356 g, 3.107 mmol) were added and stirred for 16 h. The resulting reaction mixture was poured in to water (100 ml) and extracted with EtOAc (80 ml×2). The resulting crude was purified by PREP HPLC yielding N-(3-(5-methoxybenzo[d]thiazol-2-yl)pyridin-4-yl)methanesulfonamide (0.075 g, 0.223 mmol). MS: ES+ 336.0 (M+1); 1H NMR (400 MHz, DMSO-$d_6$) δ ppm: 13.13 (s, 1H), 9.14 (d, J=1.2, 1H), 8.06 (dd, J=7.2, 1.2 Hz, 1H), 8.00 (d, J=8.0 Hz, 1H), 7.54 (d, J=2.4 Hz, 1H), 7.46 (d, J=7.2 Hz, 1H), 7.08 (dd, J=8.8, 2.4 Hz, 1H), 3.87 (s, 3H), 3.09 (s, 3H).

Scheme-2

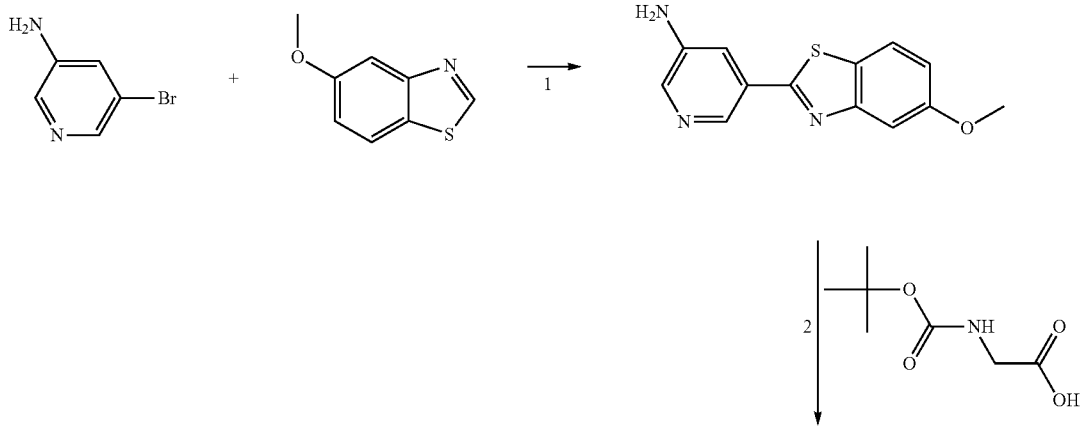

-continued

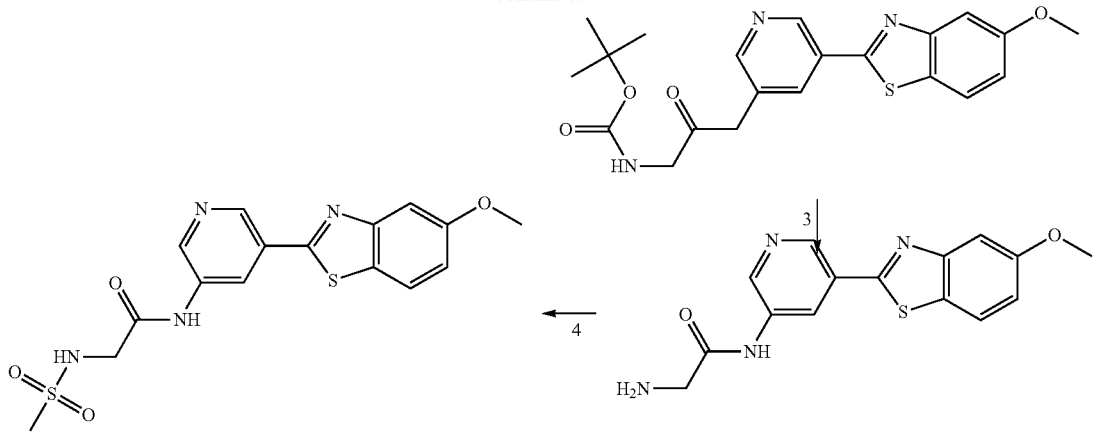

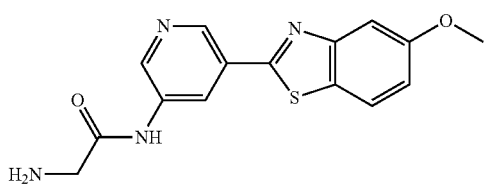 [SMILES: COc1ccc2sc(-c3cncc(NC(=O)CN)c3)nc2c1]

Example 2B
2-amino-N-(5-(5-methoxybenzo[d]thiazol-2-yl)pyridin-3-yl)acetamide hydrochloride (PST-077)

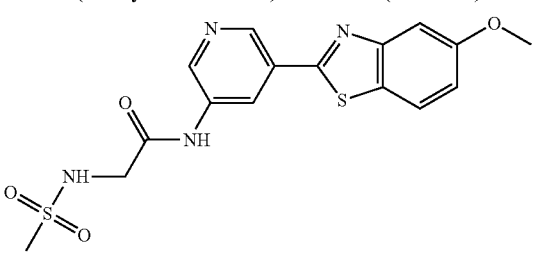

Example 2C
N-(5-(5-methoxybenzo[d]thiazol-2-yl)pyridin-3-yl)-2-(methylsulfonamido)acetamide (PST-288)

The title compound (PST-077) was synthesized via step-2 & 3 of Scheme 2, following similar synthetic procedures as mentioned for Example-1A whilst using 5-(5-methoxybenzo[d]thiazol-2-yl)pyridin-3-amine in step-4 instead of 3-(5-methoxybenzo[d]thiazol-2-yl)pyridin-4-amine.

MS: ES+ 315.02 (M+1); 1H NMR (400 MHz, DMSO-$d_6$) δ ppm: 11.60 (s, 1H), 8.97 (dd, J=12, 1.6 Hz, 2H), 8.88 (d, J=2.0 Hz, 1H), 8.36 (br s, 3H), 8.07 (d, J=8.8 Hz, 1H), 7.70 (d, J=2.4 Hz, 1H), 7.16 (dd, J=8.8, 2.4 Hz, 1H), 3.89-3.93 (m, 2H), 3.88 (s, 3H).

The title compound (PST-288) was synthesized via step-4 of Scheme 2, following similar synthetic procedures as mentioned for Example-1A whilst using 5-(5-methoxybenzo[d]thiazol-2-yl)pyridin-3-amine in step-4 instead of 3-(5-methoxybenzo[d]thiazol-2-yl)pyridin-4-amine.

MS: ES+ 292.99 (M+1); 1H NMR (400 MHz, DMSO-$d_6$) δ ppm: 10.72 (s, 1H), 8.97 (s, 1H), 8.90 (d, J=1.2 Hz, 2H), 8.08 (d, J=8.8 Hz, 1H), 7.69 (d, J=2.4 Hz, 1H), 7.62 (s, 1H), 7.16 (dd, J=8.8, 2.4 Hz, 1H), 3.96 (d, J=3.6 Hz, 2H), 3.88 (s, 3H), 3.02 (s, 3H).

Scheme-3

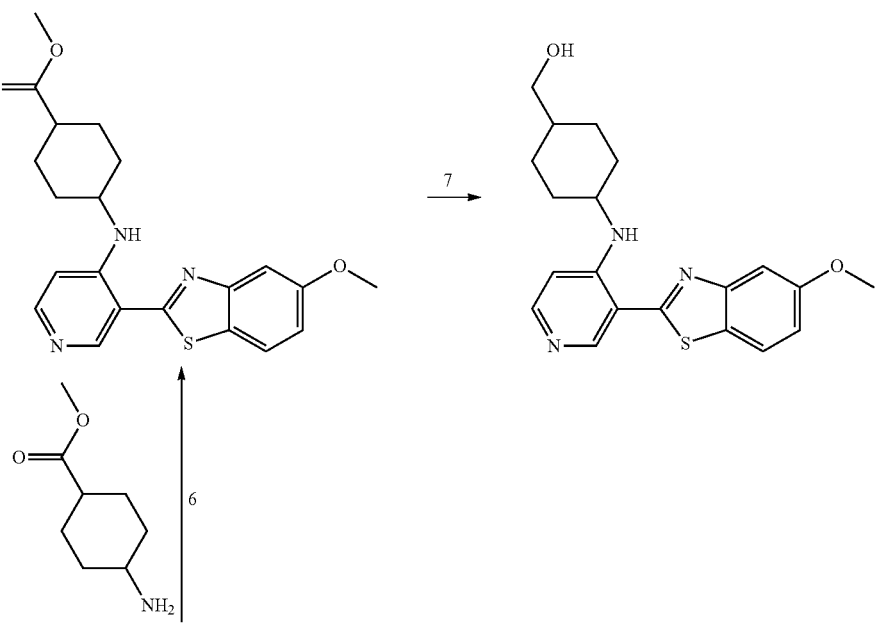

81
82
-continued
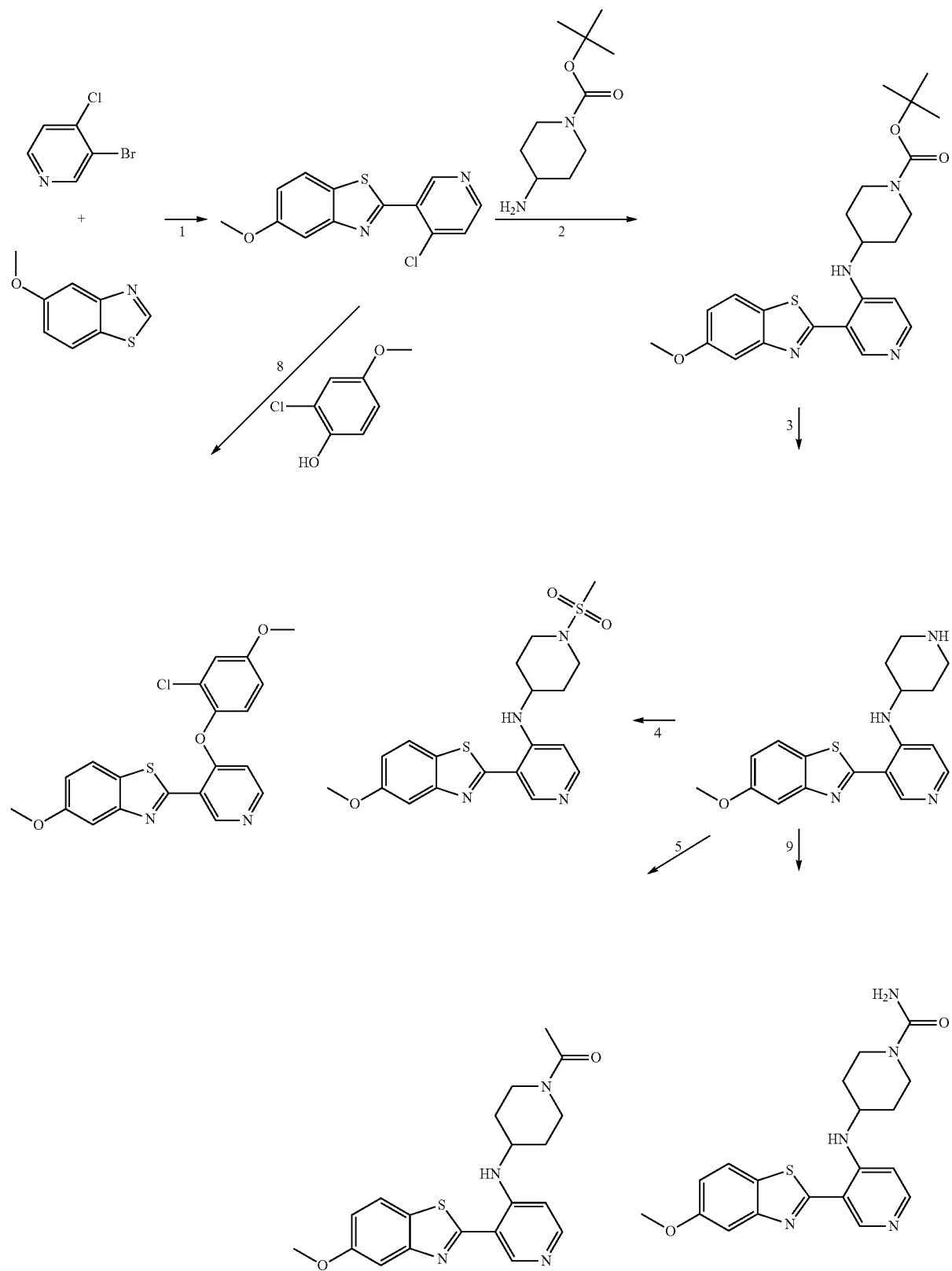

Example 3A. 3-(5-methoxybenzo[d]thiazol-2-yl)-N-(1-(methylsulfonyl)piperidin-4-yl)pyridin-4-amine (PST-155)

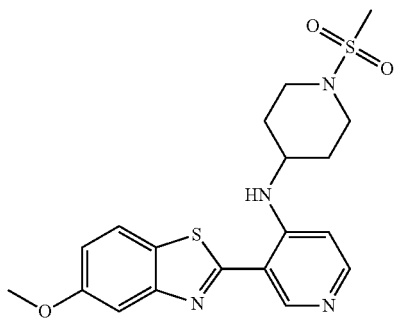 [SMILES: COc1ccc2sc(-c3cnccc3NC3CCN(S(C)(=O)=O)CC3)nc2c1]

Step-1 2-(4-chloropyridin-3-yl)-5-methoxybenzo[d]thiazole

To a stirred solution of 5-Methoxybenzo[d]thiazole (0.5 g, 3.029 mmol) in toluene (20 ml) were added $Cs_2CO_3$ (4.88 g, 15.145 mmol) and 3-bromo-4-chloropyridine (1.152 g, 6.058 mmol). Cu(I)Br (0.344 g, 2.423 mmol), $Pd(OAc)_2$ (0.152 g, 0.75 mmol) and Xantphos (0.694 g, 0.121 mmol) were added to the reaction mixture and heated at 60° C. for 6 h. The resulting reaction mixture was cooled to ambient temperature and poured into water (3×50 ml) and extracted with EtOAc (3×50 ml). The resulting crude material was purified by flash chromatography (14% EtOAc in hexane) yielding 2-(4-chloropyridin-3-yl)-5-methoxybenzo[d]thiazole (0.64 g, 2.320 mmol). MS: ES+ 276.99 (M+1); 1H NMR (400 MHz, DMSO-$d_6$) δ ppm: 9.32 (s, 1H), 8.68 (d, J=5.2 Hz, 1H), 8.11 (d, J=8.8 Hz, 1H), 7.82 (d, J=5.6 Hz, 1H), 7.71 (d, J=2.4 Hz, 1H), 7.19 (dd, J=8.8, 2.4 Hz, 1H), 3.89 (s, 3H).

Step-2 tert-butyl 4-((3-(5-methoxybenzo[d]thiazol-2-yl)pyridin-4-yl)amino)piperidine-1-carboxylate To a stirred solution of 2-(4-chloropyridin-3-yl)-5-methoxybenzo[d]thiazole ((0.25 g, 0.905 mmol in NMP (5 ml) were added $K_2CO_3$ (0.49 g, 3.62 mmol) and 1-Boc 4-aminopiperidine (0.90 g, 4.525 mmol) before heating at 150° C. for 18 hours. The resulting reaction mixture was poured into water (100 ml) and extracted with EtOAc (2×25 ml). The resulting crude material was purified by flash chromatography (60% EtOAc in hexane) yielding tert-butyl 4-((3-(5-methoxybenzo[d]thiazol-2-yl)pyridin-4-yl)amino)piperidine-1-carboxylate (PST-134) (0.26 g, 0.590 mmol). MS: ES+ 441.31 (M+1); 1H NMR (400 MHz, DMSO-$d_6$) δ ppm: 9.33 (d, J=8.0 Hz, 1H), 8.73 (s, 1H), 8.19 (d, J=6.0 Hz, 1H), 7.99 (d, J=8.8 Hz, 1H), 7.63-7.65 (m, 1H), 7.10 (dd, J=8.8, 2.4 Hz, 1H), 6.95 (d, J=6.0 Hz, 1H), 3.70-4.00 (m, 6H), 3.0-3.13 (m, 2H), 2.0-2.1 (m, 2H), 1.45-1.55 (m, 2H), 1.42 (s, 9H).

Step-3 3-(5-methoxybenzo[d]thiazol-2-yl)-N-(piperidin-4-yl)pyridin-4-amine

To a stirred solution tert-butyl 4-((3-(5-methoxybenzo[d]thiazol-2-yl)pyridin-4-yl)amino)piperidine-1-carboxylate (0.27 g, 0.613 mmol) in 1,4-dioxane (5 ml) were added HCl in dioxane (2.0 ml) and stirred for 2 h. The resulting reaction mixture was poured into saturated $NaHCO_3$ solution (50 ml) and extracted with EtOAc (2×50 ml) yielding 3-(5-methoxybenzo[d]thiazol-2-yl)-N-(piperidin-4-yl)pyridin-4-amine (PST-141) (0.203 g, 0.596 mmol). MS: ES+ 341.11 (M+1); 1H NMR (400 MHz, DMSO-$d_6$) δ ppm: 10.64 (d, J=7.6 Hz, 1H), 9.11-9.31 (m, 2H), 9.00 (s, 1H), 8.41 (d, J=7.6 Hz, 1H), 8.14 (d, J=8.8 Hz, 1H), 7.68 (d, J=2.4 Hz, 1H), 7.45 (d, J=7.2 Hz, 1H), 7.23 (dd, J=8.8, 2.4 Hz, 1H), 4.21-4.23 (m, 1H), 3.88 (s, 3H), 2.90-3.3 (m, 4H), 2.20-2.25 (m, 2H), 1.89-1.96 (m 2H).

Step-4 3-(5-methoxybenzo[d]thiazol-2-yl)-N-(1-(methylsulfonyl)piperidin-4-yl)pyridin-4-amine To a stirred solution 3-(5-methoxybenzo[d]thiazol-2-yl)-N-(piperidin-4-yl)pyridin-4-amine (0.045 g, 0.132 mmol) in THF (10 ml) were added $K_2CO_3$ (0.054 g, 0.396 mmol) and mesyl chloride (0.038 g, 0.264) at ambient temperature. The reaction mixture was stirred at ambient temperature for 2 h. The resulting reaction mixture was poured into water (50 ml) and extracted with EtOAc (2×10 ml). The resulting crude material was purified by flash chromatography (75% EtOAc in hexane) yielding 3-(5-methoxybenzo[d]thiazol-2-yl)-N-(1-(methylsulfonyl)piperidin-4-yl)pyridin-4-amine (PST-155) (0.040 g, 0.095 mmol). LCMS: Method C, 1.851 min, MS: ES+ 419.2 (M+1).

Example 3B 1-(4-((3-(5-methoxybenzo[d]thiazol-2-yl)pyridin-4-yl)amino)piperidin-1-yl)ethan-1-one (PST-156)

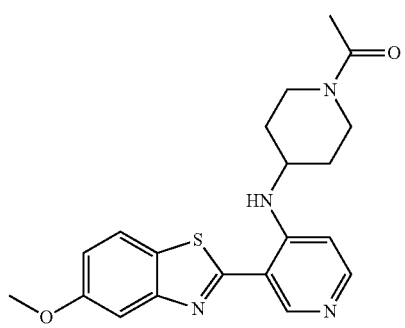 [SMILES: COc1ccc2sc(-c3cnccc3NC3CCN(C(C)=O)CC3)nc2c1]

Step-5 1-(4-((3-(5-methoxybenzo[d]thiazol-2-yl)pyridin-4-yl)amino)piperidin-1-yl)ethan-1-one To a stirred solution 3-(5-methoxy-1,3-benzothiazol-2-yl)-N-(piperidin-4-yl)pyridin-4-amine (the product of Step-1 of Example 3A) (0.11 g, 0.323 mmol) in THF (2.5 ml) were added $K_2CO_3$ (0.134 g, 0.96 mmol) and acetyl chloride (0.05 g, 0.646 mmol) and stirred for 18 h. The resulting reaction mixture was poured into saturated $NaHCO_3$ solution (100 ml) and extracted with EtOAc (2×50 ml). The resulting crude material was purified by flash chromatography (20% EtOAc in hexane) yielding 1-(4-((3-(5-methoxybenzo[d]thiazol-2-yl)pyridin-4-yl)amino)piperidin-1-yl)ethan-1-one (PST-156) (0.08 g, 0.209 mmol). MS: ES+ 383.12 (M+1).

Example 3C (4-((3-(5-methoxybenzo[d]thiazol-2-yl)pyridin-4-yl)amino)cyclohexyl)methanol (PST-173)

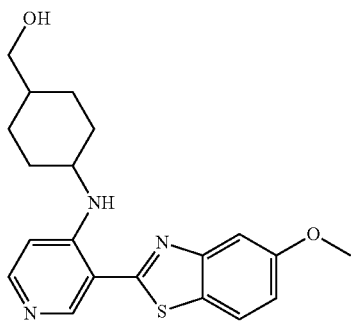 [SMILES: COc1ccc2sc(-c3cnccc3NC3CCC(CO)CC3)nc2c1]

Step-7 (4-((3-(5-methoxybenzo[d]thiazol-2-yl)pyridin-4-yl)amino)cyclohexyl)methanol To a stirred solution of methyl 4-((3-(5-methoxybenzo[d]thiazol-2-yl)pyridin-4-yl)amino)cyclohexane-1-carboxylate (PST-166) (synthesized via step-6 of Scheme 3, by following similar synthetic procedures as described in Example-3A, but using methyl 4-aminocyclohexane-1-carboxylate in step-2 instead of 1-Boc 4-aminopiperidine) (0.075 g, 0.188 mmol) in THF (5 ml) was added LAH (1.0 M in THF) (0.4 ml, 1.321 mmol) at 0° C. under nitrogen atmosphere. The reaction mixture was stirred at ambient temperature for 2 h. The reaction mixture was poured into saturated $NH_4Cl$ (30 ml) and extracted with EtOAc (2×20 ml). The resulting crude material was purified by flash chromatography (90% ethyl acetate in hexane) yielding (4-((3-(5-methoxybenzo[d]thiazol-2-yl)pyridin-4-yl)amino)cyclohexyl)methanol (PST-173) (0.01 g, 0.027 mmol). MS: ES+ 370.15 (M+1); 1H NMR (400 MHz, DMSO-$d_6$) δ ppm: 9.25 (d, J=6.8 Hz, 1H), 8.60-8.80 (m, 1H), 8.10-8.25 (m, 1H), 7.99 (d, J=8.4 Hz, 1H), 7.60 (d, J=2.0 Hz, 1H), 7.10 (dd, 8.8, 2.4 Hz, 1H), 6.89 (s, 1H), 4.49 (t, J=5.2 Hz, 1H), 3.89 (s, 3H), 3.49-3.59 (m, 1H), 3.27 (t, J=5.6 Hz, 2H), 2.10-2.20 (m, 2H), 1.80-1.90 (m, 2H), 1.32-1.51 (m, 3H), 1.08-1.20 (m, 2H).

Example 3D 3-(5-methoxybenzo[d]thiazol-2-yl)-N-phenylpyridin-4-amine (PST-128)

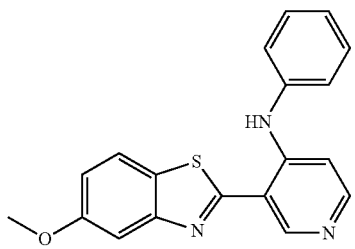 [SMILES: COc1ccc2sc(-c3cnccc3Nc3ccccc3)nc2c1]

The title compound (PST-128) was synthesized via step-2 of Scheme 3, following similar synthetic procedures as mentioned for Example-3A whilst using aniline in step-2 instead of 1-Boc 4-aminopiperidine.

LCMS: Method A, 3.454 min, MS: ES+(M+1); 1H NMR (400 MHz, DMSO-$d_6$) δ ppm: 11.06 (s, 1H), 8.88 (s, 1H), 8.23 (d, J=6.0 Hz, 1H), 8.04 (d, J=8.8 Hz, 1H), 7.74 (d, J=2.8 Hz, 1H), 7.43-7.52 (m, 4H), 7.28 (t, J=7.2 Hz, 1H), 7.13 (dd, J=8.8, 2.4 Hz, 1H), 7.07 (d, J=6.0 Hz, 1H), 3.87 (s, 3H).

Example 3E

N-benzyl-3-(5-methoxybenzo[d]thiazol-2-yl)pyridin-4-amine (PST-150)

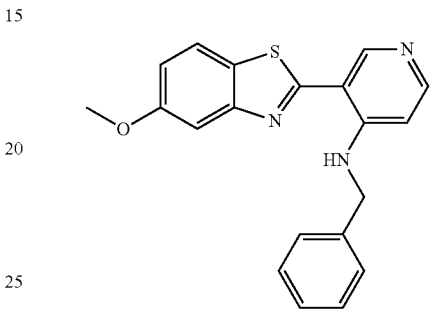

The title compound (PST-150) was synthesized via step-2 of Scheme 3, following similar synthetic procedures as mentioned for Example-3A whilst using phenylmethanamine in step-2 instead of 1-Boc 4-aminopiperidine LCMS: Method A, 3.159 min, MS: ES+ 348.17 (M+1); 1H NMR (400 MHz, DMSO-$d_6$, 80° C.) δ ppm: 9.62 (m, 1H), 8.73 (s, 1H), 8.16 (d, J=6.0 Hz, 1H), 7.98 (d, J=8.8 Hz, 1H), 7.72 (d, J=5.6 Hz, 1H), 7.39-7.45 (m, 4H), 7.28-7.31 (m, 1H), 7.12 (dd, J=8.8, 2.8 Hz, 1H), 6.78 (d, J=6.0 Hz, 1H), 4.68 (d, J=5.6 Hz, 2H), 3.89 (s, 3H).

Example 3F

N-(2-chloro-4-methoxyphenyl)-3-(5-methoxybenzo[d]thiazol-2-yl)pyridin-4-amine (PST-120)

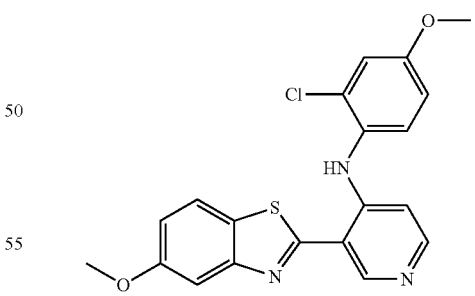

The title compound (PST-120) was synthesized via step-2 of Scheme 3, following similar synthetic procedures as mentioned for Example-3A whilst using 2-chloro-4-methoxyaniline in step-2 instead of 1-Boc 4-aminopiperidine LCMS: Method A, 3.341 min, MS: ES+ 398.1 (M+1); 1H NMR (400 MHz, DMSO-$d_6$) δ ppm: 10.92 (s, 1H), 8.8 (s, 1H), 8.20 (d, J=6.0 Hz, 1H), 8.05 (d, J=8.0 Hz, 1H), 7.66 (d, J=2.4 Hz, 1H), 7.54 (d, J=8.8 Hz, 1H), 7.29 (d, J=2.8 Hz, 1H), 7.14 (dd, =8.8, 2.4 Hz, 1H), 7.07 (dd, J=8.8, 2.8 Hz, 1H), 6.62 (d, J=6.0 Hz, 1H), 3.86 (s, 3H), 3.84 (s, 3H).

Example 3G 3-(5-methoxybenzo[d]thiazol-2-yl)-N-(4-methoxy-cyclohexyl)pyridin-4-amine (PST-206)

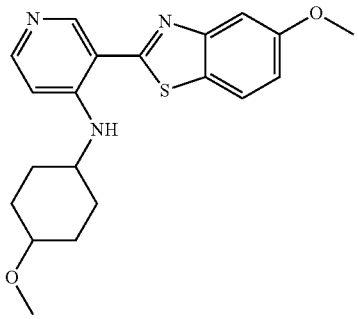 [SMILES: COc1ccc2sc(-c3cnccc3NC3CCC(OC)CC3)nc2c1]

The title compound (PST-206) was synthesized via step-2 of Scheme 3, following similar synthetic procedures as mentioned for Example-3A whilst using 4-methoxycyclohexan-1-amine in step-2 instead of 1-Boc 4-aminopiperidine LCMS: Method C, 2.242 min, MS: ES+ 370.17 (M+1)

Example 3H 2-(4-(2-chloro-4-methoxyphenoxy)pyridin-3-yl)-5-methoxybenzo[d]thiazole (PST-129)

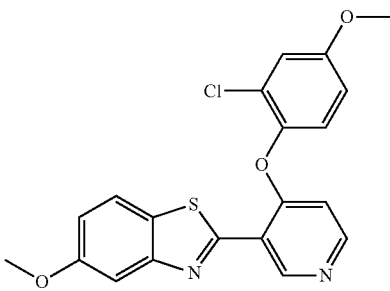

Step-8 2-(4-(2-chloro-4-methoxyphenoxy)pyridin-3-yl)-5-methoxybenzo[d]thiazole

To a stirred solution 2-(4-chloropyridin-3-yl)-5-methoxybenzo[d]thiazole (Step-1 product, Example 3A) (0.025 g, 0.090 mmol) in DMF (2.5 ml) were added $CS_2CO_3$ (0.035 g, 0.096 mmol) and 2-Chloro 4-Methoxyphenol (0.015 g, 0.094 mmol). The reaction mixture was stirred at 90° C. for 20 h. The resulting reaction mixture was poured into Water (250 ml) and extracted with EtOAc (3×15 ml) yielding 2-(4-(2-chloro-4-methoxyphenoxy)pyridin-3-yl)-5-methoxybenzo[d]thiazole (PRI-98=PST-0000129) (0.087 g, 0.175 mmol). MS: ES+ 398.99 (M+1); 1H NMR (400 MHz, DMSO-$d_6$) δ ppm: 9.51 (s, 1H), 8.53 (d, J=6.0 Hz, 1H), 8.05 (d, J=8.8 Hz, 1H), 7.70 (d, J=2.4 Hz, 1H), 7.51 (d, J=8.8 Hz, 1H), 7.34 (d, J=2.8 Hz, 1H), 7.09-7.15 (m, 2H), 6.73 (d, J=5.6 Hz, 1H), 3.90 (s, 3H), 3.85 (s, 3H).

Example 3I

Step-8 2-(4-(2-chloro-4-methoxyphenoxy)pyridin-3-yl)-5-methoxybenzo[d]thiazole (PST131)

The title compound (PST-131) was synthesized via step-2 of Scheme 3, following similar synthetic procedures as mentioned for Example-3A whilst using 2-fluoro-4-methoxyaniline in step-2 instead of 1-Boc 4-aminopiperidine.

Example 3J 4-((3-(5-methoxybenzo[d]thiazol-2-yl)pyridin-4-yl)amino)piperidine-1-carboxamide (PST-151)

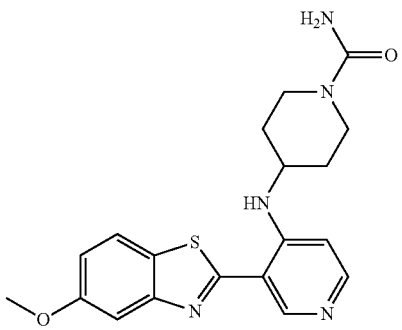 [SMILES: COc1ccc2sc(-c3cnccc3NC3CCN(C(N)=O)CC3)nc2c1]

Step-9 4-((3-(5-methoxybenzo[d]thiazol-2-yl)pyridin-4-yl)amino)piperidine-1-carboxamide To a stirred solution 2-(4-chloropyridin-3-yl)-5-methoxybenzo[d]thiazole (the product of Step-3 of Example 3A) (0.1 g, 0.29 mmol) in THF (3 ml) were added trimethylsilylisocynate (0.084 g, 0.73 mmol)) and stirred for 24 h. The resulting reaction mixture was poured into Water (50 ml) and extracted with EtOAc (3×15 ml). The resulting crude material was purified by flash chromatography (5% MeOH in DCM) yielding 4-((3-(5-methoxybenzo[d]thiazol-2-yl)pyridin-4-yl)amino)piperidine-1-carboxamide (PST-151) (0.05 g, 0.130 mmol). MS: ES+ 384.17 (M+1); 1H NMR (400 MHz, DMSO-$d_6$) δ ppm: 9.35 (d, J=8.0 Hz, 1H), 8.70-8.80 (m, 1H), 8.15-8.25 (m, 1H), 8.00 (d, J=8.4 Hz, 1H), 7.61 (d, J=2.0 Hz, 1H), 7.10 (dd, J=8.8, 2.4 Hz, 1H), 6.87 (d, J=5.2 Hz, 1H), 6.00 (s, 2H), 3.80-3.95 (m, 6H), 2.97-3.05 (m, 2H), 1.95-2.05 (m, 2H), 1.40-1.55 (m, 2H).

Scheme-4

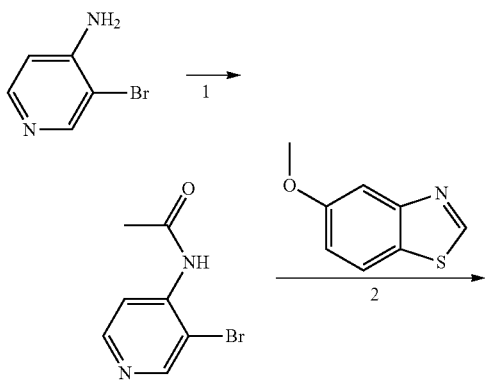

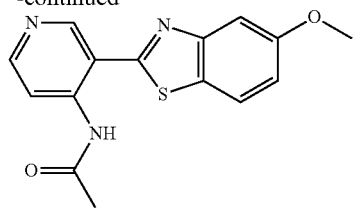

Example 4A

N-(3-(5-methoxybenzo[d]thiazol-2-yl)pyridin-4-yl) acetamide (PST-087)

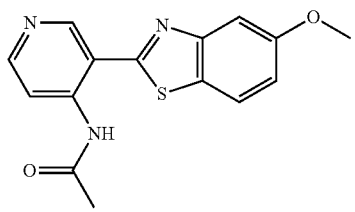 [SMILES: COc1ccc2sc(-c3cnccc3NC(C)=O)nc2c1]

Step-1 N-(3-bromopyridin-4-yl)acetamide

To a stirred solution 3-bromopyridin-4-amine (0.5 g, 2.890 mmol) in dichloromethane (5.0 ml) were added DIPEA (0.45 g, 3.179 mmol) and acetyl chloride (0.22 g, 3.179 mmol) at 0° C. The reaction mixture was stirred for 18 h. The resulting reaction mixture was poured into saturated NaHCO₃ solution (100 ml) and extracted with DCM (2×50 ml). The resulting crude material was purified by flash chromatography (20% EtOAc in hexane) yielding N-(3-bromopyridin-4-yl)acetamide (0.63 g, 2.944 mmol). MS: ES+ 215.0 (M+1).

Step-2 N-(3-(5-methoxybenzo[d]thiazol-2-yl)pyridin-4-yl)acetamide

To a stirred solution of 5-Methoxybenzo[d]thiazole (0.15 g, 0.908 mmol) in toluene (5.0 ml) were added Cs₂CO₃ (0.88 g, 2.726 mmol) and N-(3-bromopyridin-4-yl)acetamide (0.3 g, 1.272 mmol). Cu(I)Br (0.024 g, 0.363 mmol), Pd(OAc)₂ (0.05 g, 0.109 mmol) and Xantphos (0.1 g, 0.182 mmol) were added and heated to 110° C. for 48 h. The resulting reaction mixture was cooled to ambient temperature and poured into water (50 ml) and extracted with EtOAc (3×40 ml). The resulting crude material was purified by flash chromatography (42% EtOAc in hexane) yielding N-(3-(5-methoxybenzo[d]thiazol-2-yl)pyridin-4-yl)acetamide (PST-087) (0.1 g, 0.334 mmol). MS: ES+ 300.2 (M+1); 1H NMR (400 MHz, DMSO-d₆) δ ppm: 12.25 (s, 1H), 9.05 (s, 1H), 8.51-8.56 (m, 2H), 8.07 (d, J=8.8 Hz, 1H), 7.74 (d, J=2.4 Hz, 1H), 7.17 (dd, J=8.8, 2.4 Hz, 1H), 3.90 (s, 3H), 2.33 (s, 3H).

Example 4B

N-(5-(5-methoxybenzo[d]thiazol-2-yl)-2-methylpyridin-4-yl)acetamide (PST-157)

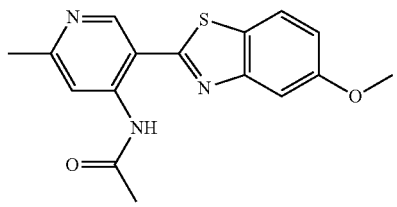

The title compound (PST-157) was synthesized via step-1 & 2 of Scheme 4, following similar synthetic procedures as mentioned for Example-4A whilst using 5-bromo-2-methylpyridin-4-amine in step-1 instead of 3-bromopyridin-4-amine.

MS: ES+ 314.16 (M+1); 1H NMR (400 MHz, DMSO-d₆) δ ppm: 12.22 (s, 1H), 8.95 (s, 1H), 8.42 (s, 1H), 8.07 (d, J=8.8 Hz, 1H), 7.74 (d, J=2.4 Hz, 1H), 7.17 (dd, J=8.8, 2.8 Hz, 1H), 3.90 (s, 3H), 2.52 (s, 3H), 2.33 (s, 3H).

Example 4C

N-(5-(5-methoxybenzo[d]thiazol-2-yl)pyridin-2-yl) acetamide (PST-082)

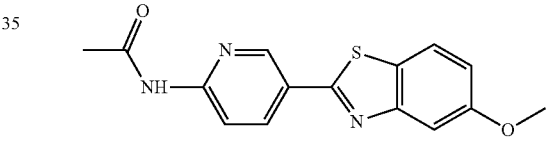

The title compound (PST-082) was synthesized via step-1 & 2 of Scheme 4, following similar synthetic procedures as mentioned for Example-4A whilst using 5-bromopyridin-2-amine in step-1 instead of 3-bromopyridin-4-amine.

MS: ES+ 300.04 (M+1); 1H NMR (400 MHz, DMSO-d₆) δ ppm): 10.89 (s, 1H), 8.98 (dd, J=2.4, 0.4 Hz, 1H), 8.41 (dd, J=8.8, 2.4 Hz, 1H), 8.27 (d, J=8.8 Hz, 1H), 8.02 (d, J=8.8 Hz, 1H), 7.61 (d, J=2.4 Hz, 1H), 7.11 (dd, J=8.8, 2.8 Hz, 1H), 3.97 (s, 3H), 2.15 (s, 3H).

Example 4D

N-(5-(5-methoxybenzo[d]thiazol-2-yl)pyridin-3-yl) isobutyramide (PST-076)

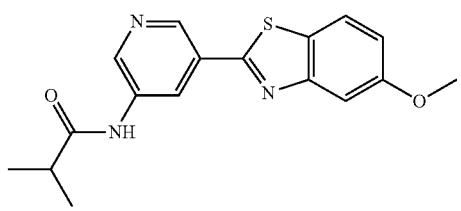 [SMILES: COc1ccc2sc(-c3cncc(NC(=O)C(C)C)c3)nc2c1]

The title compound (PST-076) was synthesized via step-1 & 2 of Scheme 4, following similar synthetic procedures as mentioned for Example-4A whilst using 5-bromopyridin-3-amine in step-1 instead of 3-bromopyridin-4-amine & Isobutyryl chloride instead of acetyl chloride.

MS: ES+ 328.51 (M+1); 1H NMR (400 MHz, DMSO-d$_6$) δ ppm): 10.35 (s, 1H), 8.81-8.91 (m, 3H), 8.06 (d, J=8.8 Hz, 1H), 7.67 (d, J=2.4 Hz, 1H), 7.15 (dd, J=8.8, 2.4 Hz, 1H), 3.88 (s, 3H), 2.60-2.70 (m, 2H), 1.16 (d, J=6.8 Hz, 6H).

Example 4E

N-(5-(5-methoxybenzo[d]thiazol-2-yl)pyridin-3-yl)propionamide (PST-075)

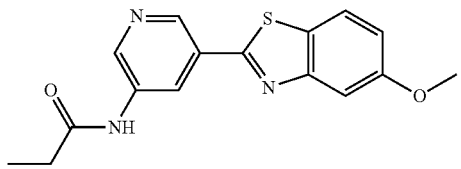 [SMILES: CCC(=O)Nc1cncc(-c2nc3cc(OC)ccc3s2)c1]

The title compound (PST-075) was synthesized via step-1 & 2 of Scheme 4, following similar synthetic procedures as mentioned for Example-4A whilst using 5-bromopyridin-3-amine in step-1 instead of 3-bromopyridin-4-amine & Propionyl chloride instead of acetyl chloride.

MS: ES+ 314.5 (M+1); 1H NMR (400 MHz, DMSO-d$_6$) δ ppm): 10.38 (s, 1H), 8.80-8.90 (m, 3H), 8.06 (d, J=8.8 Hz, 1H), 7.67 (d, J=2.4 Hz, 1H), 7.15 (dd, J=8.8, 2.8 Hz, 1H), 3.88 (s, 3H), 2.41 (q, J=15.2, 7.6 Hz, 2H), 1.13 (t, J=7.6 Hz, 3H).

Example 4F 2-(4-acetamidopyridin-2-yl)-N-methylbenzo[d]thiazole-5-carboxamide (PST-164)

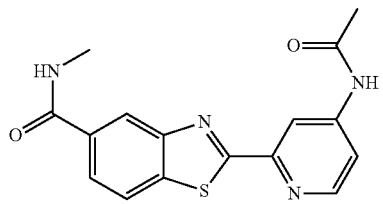 [SMILES: CNC(=O)c1ccc2sc(-c3cc(NC(C)=O)ccn3)nc2c1]

Synthesis of N-methylbenzo[d]thiazole-5-carboxamide

To stirred a solution of benzothiazole 5-carboxylic acid (2.0 g, 11.160 mmol) in THF (80 ml) were added DIPEA (5.76 g, 44.640 mmol), EDC.HCl (4.3 g, 22.320 mmol) and HOBT (3.0 g, 22.320 mmol) at 0° C. The reaction mixture was stirred at 0° C. for 45 min. Methylamine (2M in THF) (0.69 g, 22.320 mmol) was added in to the reaction mixture at 0° C. and stirred for 1 h. The resulting reaction mixture was poured in to water (200 ml) and extracted with EtOAc (200 ml×2). The resulting crude material was purified by flash chromatography (4.0% MeOH in DCM) yielding 5-(5-methoxybenzo[d]thiazol-2-yl)-N,N-dimethylpicolinamide (3.75 g, 19.528 mmol). MS: ES+ 193.01 (M+1).

The title compound (PST-164) was synthesized via step-1 & 2 of Scheme 4, following similar synthetic procedures as mentioned for Example-4A whilst using 2-bromopyridin-4-amine in step-1 instead of 3-bromopyridin-4-amine & N-methylbenzo[d]thiazole-5-carboxamide in step-2 instead of 5-methoxybenzo[d]thiazole.

MS: ES+ 327.13 (M+1); 1H NMR (400 MHz, DMSO-d$_6$) δ ppm): 12.16 (br s, 1H), 9.13 (s, 1H), 8.68-8.74 (m, 1H), 8.64 (d, J=1.2 Hz, 1H), 8.58-8.62 (m, 1H), 8.51-8.56 (m, 1H), 8.31 (d, J=8.4 Hz, 1H), 8.00 (dd, J=8.4, 1.6 Hz, 1H), 2.86 (d, J=4.4 Hz, 3H), 2.34 (s, 3H).

Scheme-5

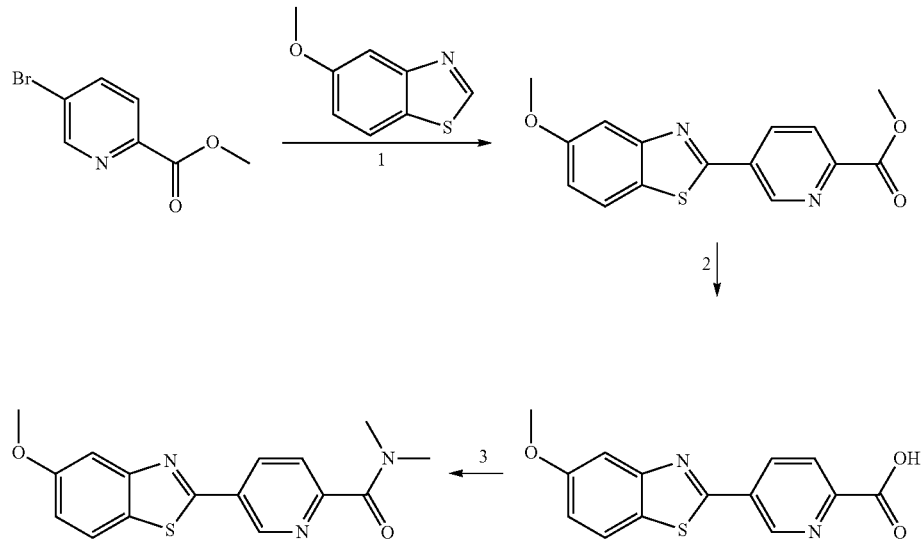

Example 5A 5-(5-methoxybenzo[d]thiazol-2-yl)-N,N-dimethylpicolinamide (PST-162)

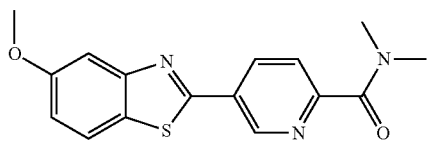 [SMILES: COc1ccc2sc(-c3ccc(C(=O)N(C)C)nc3)nc2c1]

Step-1 Methyl 5-(5-methoxybenzo[d]thiazol-2-yl)picolinate (PST-154)

The material was synthesized via step-1 of Scheme 5, following similar synthetic procedures as mentioned for Example-3A whilst using methyl 5-bromopicolinate in step-1 instead of 3-bromo-4-chloropyridine.

LCMS: Method B, 4.502 min, MS: ES+ 301.0 (M+1); 1H NMR (400 MHz, DMSO-$d_6$) δ ppm): 9.37 (dd, J=2.4, 0.8 Hz, 1H), 8.59 (dd, J=8.4, 2.4 Hz, 1H), 8.22 (dd, J=8.0. 0.4 Hz, 1H), 8.10 (d, J=8.8 Hz, 1H), 7.70 (d, J=2.4 Hz, 1H), 7.18 (dd, J=8.8, 2.4 Hz, 1H), 3.93 (s, 3H), 3.89 (s, 3H).

Step-2 5-(5-methoxybenzo[d]thiazol-2-yl)picolinic acid

To a stirred solution Methyl 5-(5-methoxybenzo[d]thiazol-2-yl)picolinate (0.2 g, 0.667 mmol) in THF:water (1:1, 3.0 ml) was added LiOH.$H_2O$ (0.056 g, 1.333 mmol) and stirred for 18 h. The resulting reaction mixture was poured into dilute HCl (50 ml) and extracted with $CHCl_3$:MeOH (9:1, 2×50 ml) yielding 5-(5-methoxybenzo[d]thiazol-2-yl)picolinic acid. MS: ES+ 287 (M+1).

Step-3 5-(5-methoxybenzo[d]thiazol-2-yl)-N,N-dimethylpicolinamide

To stirred a solution of 5-(5-methoxybenzo[d]thiazol-2-yl)picolinic acid (0.17 g, 0.594 mmol) in DMF (5.0 ml) were added HATU (0.45 g, 1.188 mmol) and DIPEA (0.23 g, 1.783 mmol). The reaction mixture was stirred for 45 min before dimethylamine hydrochloride (0.24 g, 2.972 mmol) was added and further stirred for 2 h. The resulting reaction mixture was poured in to water (100 ml) and extracted with EtOAc (100 ml×2). The resulting crude material was purified by flash chromatography (2.5% MeOH in DCM) yielding 5-(5-methoxybenzo[d]thiazol-2-yl)-N,N-dimethylpicolinamide (PST-162) (0.015 g, 0.048 mmol). MS: ES+ 314 (M+1); 1H NMR (400 MHz, DMSO-$d_6$) δ ppm): 9.25 (d, J=1.6 Hz, 1H), 8.54 (dd, J=8.0, 2.4 Hz, 1H), 8.09 (d, J=8.8 Hz, 1H), 7.76 (d, J=8.0 Hz, 1H), 7.68 (d, J=2.4 Hz, 1H), 7.17 (dd, J=8.8, 2.4 Hz, 1H), 3.89 (s, 3H), 3.05 (s, 3H), 2.99 (s, 3H).

Scheme-7

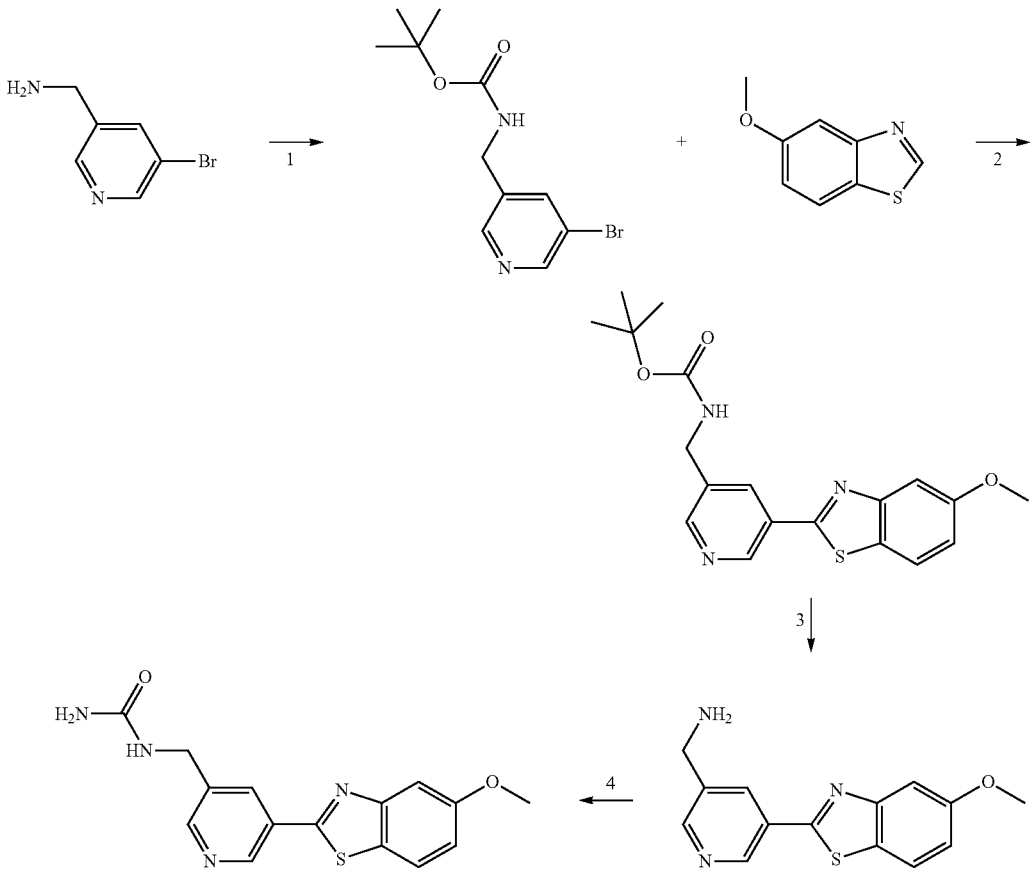

Example 7A tert-butyl ((5-(5-methoxybenzo[d]thiazol-2-yl)pyridin-3-yl)methyl)carbamate (PST-122)

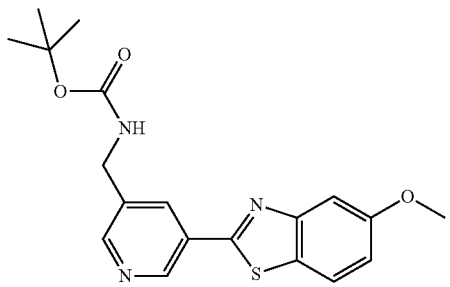 [SMILES: COc1ccc2sc(-c3cncc(CNC(=O)OC(C)(C)C)c3)nc2c1]

The title compound (PST-122) was synthesized via step-1 & 2 of Scheme 7, following similar synthetic procedures as mentioned for Example-6A whilst using 2 (5-bromopyridin-3-yl)methanamine in step-2 instead of 1-(5-bromopyridin-3-yl)-N-methylmethanamine & 5-methoxybenzo[d]thiazole in step-4 instead of methyl benzo[d]thiazole-5-carboxylate.

LCMS: Method A, 2.804 min, MS: ES+ 372.2 (M+1); 1H NMR (400 MHz, DMSO-$d_6$) δ ppm: 9.16 (br s, 1H), 8.66 (br s, 1H), 8.29 (s, 1H), 8.07 (d, J=9.1 Hz, 1H), 7.66 (d, J=2.4 Hz, 1H), 7.61 (t, J=6.0 Hz, 1H), 7.15 (dd, J=8.8, 2.8 Hz, 1H), 4.28 (d, J=6.0 Hz, 1H), 3.88 (s, 3H), 1.41 (s, 9H).

Example 7B 1-((5-(5-methoxybenzo[d]thiazol-2-yl)pyridin-3-yl)methyl)urea (PST-096)

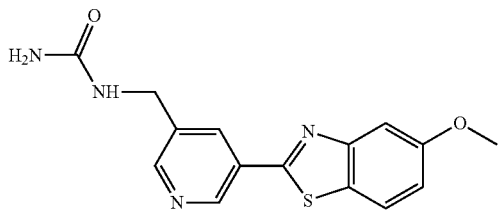

PRI-51

The title compound (PST-096) was synthesized via step-1, 2, 3 & 4 of Scheme 7, following similar synthetic procedures as mentioned for Example-3I whilst using tert-butyl ((5-(5-methoxybenzo[d]thiazol-2-yl)pyridin-3-yl)methyl)carbamate in step-9 instead of 3-(5-methoxybenzo[d]thiazol-2-yl)-N-(piperidin-4-yl)pyridin-4-amine.

LCMS: Method A, 2.057 min, MS: ES+ 315 (M+1); 1H NMR (400 MHz, DMSO-$d_6$) δ ppm: 9.09 (d, J=2.0 Hz, 1H), 8.63 (d, J=2.0 Hz, 1H), 8.30 (s, 1H), 8.06 (d, J=8.8 Hz, 1H), 7.68 (d, J=2.4 Hz, 1H), 7.15 (dd, J=9.2, 2.8 Hz, 1H), 6.74 (t, J=6.0 Hz, 1H), 5.73 (s, 2H), 4.32 (d, J=6.0 Hz, 2H), 3.88 (s, 3H).

Example 7C 1-((5-(5-methoxybenzo[d]thiazol-2-yl)pyridin-3-yl)methyl)-1-methyl urea (PST-095)

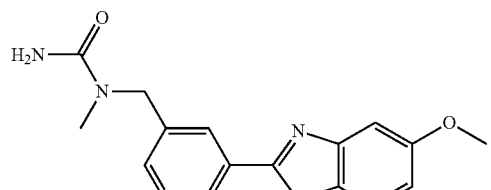

The title compound (PST-095) was synthesized via step-1, 2, 3 & 4 of Scheme 7, following similar synthetic procedures as mentioned for Example-7B whilst using tert-butyl ((5-bromopyridin-3-yl)methyl)(methyl)carbamate (the product of Step-2 of Example 6A) in step-2 instead of tert-butyl ((5-bromopyridin-3-yl)methyl)carbamate.

MS: ES+ 329 (M+1); 1H NMR (400 MHz, DMSO-$d_6$) δ ppm: 9.12 (s, 1H), 8.62 (s, 1H), 8.27 (s, 1H), 8.06 (d, J=8.8 Hz, 1H), 7.70 (s, 1H), 7.16 (dd, J=8.8, 2.8 Hz, 1H), 6.10 (s, 2H), 4.56 (s, 2H), 3.88 (s, 3H), 2.84 (s, 3H).

Scheme-8

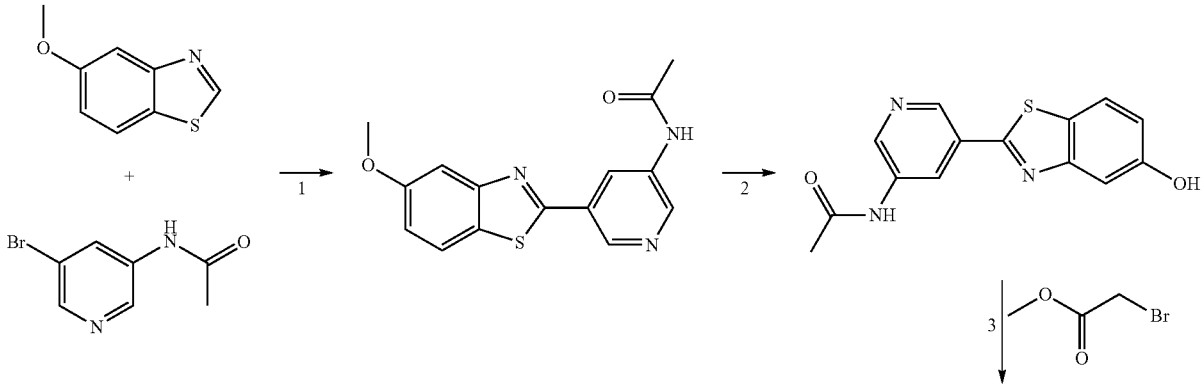

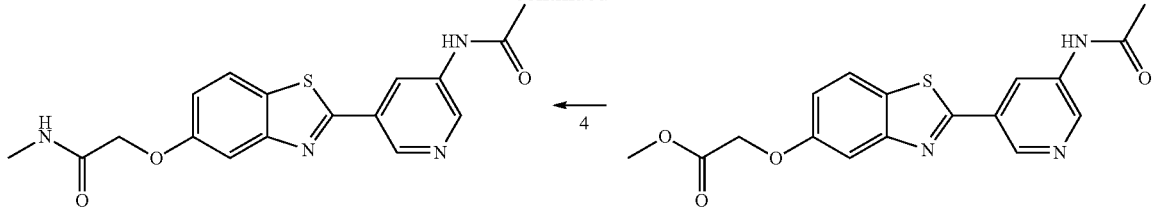

Example 8A

N-(5-(5-hydroxybenzo[d]thiazol-2-yl)pyridin-3-yl)acetamide (PST-110)

Example 8B 2-((2-(5-acetamidopyridin-3-yl)benzo[d]thiazol-5-yl)oxy)-N-methylacetamide (PST-098)

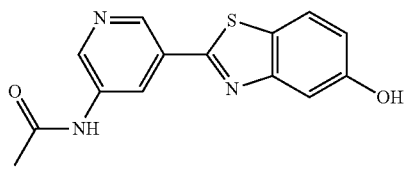 [SMILES: CC(=O)Nc1cncc(-c2nc3cc(O)ccc3s2)c1]

Step-2 N-(5-(5-hydroxybenzo[d]thiazol-2-yl)pyridin-3-yl)acetamide

To a solution of N-(5-(5-methoxybenzo[d]thiazol-2-yl)pyridin-3-yl)acetamide (PST-001) (which was synthesized via step-1 of Scheme 8, following similar synthetic procedures as described in Example-2A, but using N-(5-bromopyridin-3-yl)acetamide in step-1 instead of 5-bromopyridin-3-amine) (0.35 g, 1.170 mmol) in dichloroethane (12.0 ml) was added $AlCl_3$ (1.5 g, 1.170 mmol). The reaction mixture was stirred at 60° C. for 4 h before pouring into saturated $NH_4Cl$ solution and extracted with EtOAc (2×50 ml). The resulting crude was purified by flash chromatography (6.0% MeOH in DCM) yielding N-(5-(5-hydroxybenzo[d]thiazol-2-yl)pyridin-3-yl)acetamide (PST-110) (0.1 g, 0.350 mmol). MS: ES+ 286 (M+1); 1H NMR (400 MHz, DMSO-$d_6$) δ ppm: 10.44 (s, 1H), 9.86 (s, 1H), 8.88 (d, J=2.0 Hz, 1H), 8.77-8.82 (m, 2H), 7.95 (d, J=8.8 Hz, 1H), 7.42 (d, J=2.4 Hz, 1H), 7.01 (dd, J=8.4, 2.4 Hz, 1H), 2.13 (s, 3H).

Step-3 Methyl 2-((2-(5-acetamidopyridin-3-yl)benzo[d]thiazol-5-yl)oxy)acetate

To a stirred solution N-(5-(5-hydroxybenzo[d]thiazol-2-yl)pyridin-3-yl)acetamide (0.2 g, 0.701 mmol) in DMF (10.0 ml) were added $K_2CO_3$ (0.38 g, 2.806 mmol) and methyl 2-bromoacetate (0.16 g, 1.052 mmol). The reaction mixture was stirred at 150° C. for 18 h and poured into water (50 ml). The resulting mixture was extracted with EtOAc (2×40 ml). The resulting crude was purified by flash chromatography (5.5% methanol in DCM) yielding methyl 2-((2-(5-acetamidopyridin-3-yl)benzo[d]thiazol-5-yl)oxy)acetate (0.03 g, 0.084 mmol). MS: ES+ 357.9 (M+1); 1H NMR (400 MHz, DMSO-$d_6$) δ ppm: 10.46 (s, 1H), 8.90 (d, J=2.0 Hz, 1H), 8.81-8.84 (m, 2H), 8.08 (d, J=8.8 Hz, 1H), 7.66 (d, J=2.4 Hz, 1H), 7.19 (dd, J=9.2, 2.8 Hz, 1H), 4.96 (s, 2H), 3.73 (s, 3H), 2.14 (s, 3H).

Step-4 2-((2-(5-acetamidopyridin-3-yl)benzo[d]thiazol-5-yl)oxy)-N-methylacetamide To a stirred solution N-(5-(5-hydroxybenzo[d]thiazol-2-yl)pyridin-3-yl)acetamide (0.025 g, 0.070 mmol) in MeOH (2.0 ml) was added methyl amine (33% solution in MeOH) (0.004 g, 0.140 mmol). The reaction mixture was stirred at 70° C. for 18 h and poured into water (10 ml) and extracted with EtOAc (2×15 ml). The resulting crude material was purified by flash chromatography (6.0% methanol in DCM) yielding 2-((2-(5-acetamidopyridin-3-yl)benzo[d]thiazol-5-yl)oxy)-N-methylacetamide (PST-098) (0.005 g, 0.014 mmol). MS: ES+ 357 (M+1); 1H NMR (400 MHz, DMSO-$d_6$) δ ppm: 10.46 (s, 1H), 8.82-8.91 (m, 3H), 8.09-8.15 (m, 2H), 7.65 (d, J=2.0 Hz, 1H), 7.23 (dd, J=8.8, 2.4 Hz, 1H), 4.61 (s, 2H), 2.68 (d, J=4.8 Hz, 3H), 2.14 (s, 3H).

Scheme-9

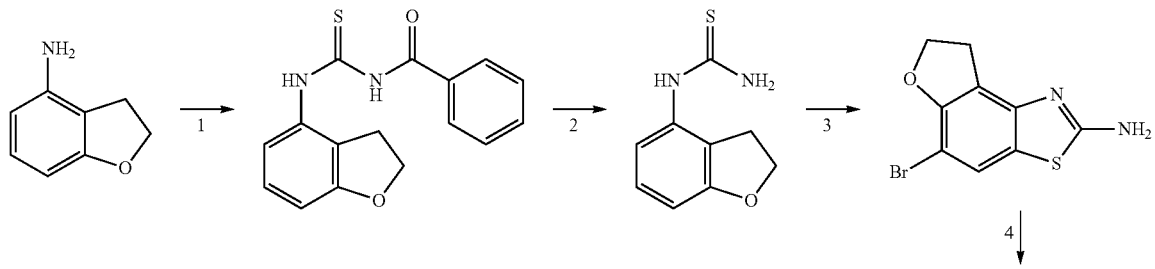

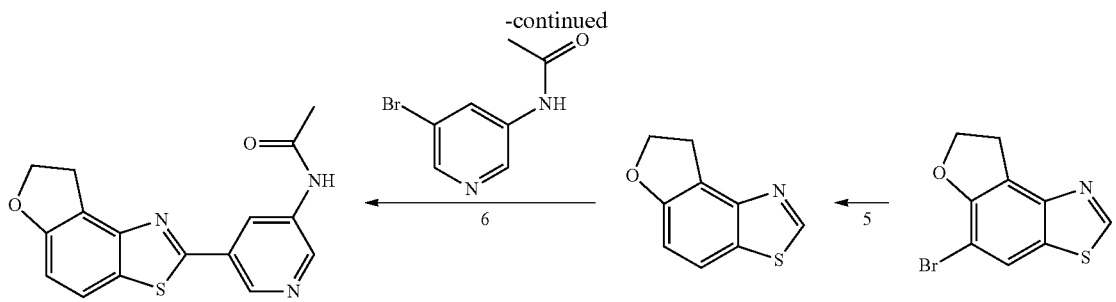

Example 9A

N-(5-(7,8-dihydrobenzofuro[4,5-d]thiazol-2-yl)pyridin-3-yl)acetamide (PST-201)

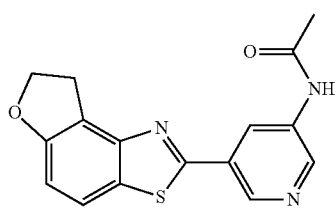 [SMILES: CC(=O)Nc1cncc(-c2nc3c4c(ccc3s2)OCC4)c1]

Step-1 N-((2,3-dihydrobenzofuran-4-yl)carbamothioyl)benzamide

To a stirred solution 2,3-dihydrobenzofuran-4-amine (0.95 g, 7.033 mmol) in acetone (3.0 ml) was added benzoyl isothiocyanate (1.3 g, 7.736 mmol). The reaction mixture was stirred for 2 h before pouring into cold water (100 ml) and extracted with EtOAc (2×100 ml) yielding N-((2,3-dihydrobenzofuran-4-yl)carbamothioyl)benzamide (2.0 g, 6.709 mmol) MS: ES+ 299.0 (M+1)

Step-2 1-(2,3-dihydrobenzofuran-4-yl)thiourea

To a stirred solution N-((2,3-dihydrobenzofuran-4-yl)carbamothioyl)benzamide (2.0 g, 6.709 mmol) in THF:water (2:1, 30.0 ml) was added NaOH (0.54 g, 13.419 mmol). The reaction mixture was stirred at 60° C. for 18 h before pouring into cold water (100 ml) and extracted with EtOAc (3×100 ml) yielding 1-(2,3-dihydrobenzofuran-4-yl)thiourea (0.95 g, 4.895 mmol). MS: ES+ 195.28 (M+1).

Step-3 5-bromo-7,8-dihydrobenzofuro[4,5-d]thiazol-2-amine

To a stirred solution 1-(2,3-dihydrobenzofuran-4-yl)thiourea (0.95 g, 4.895 mmol) in acetic acid (10.0 ml) was added LiBr (0.64 g, 7.343 mmol). The reaction mixture was cooled to 10° C. followed by dropwise addition of $Br_2$ (0.63 g, 3.916 mmol). The reaction mixture was stirred at 70° C. for 1 h. The resulting reaction mixture was poured into saturated $NaHCO_3$ solution and extracted with EtOAc (3×60 ml). The resulting crude material was purified by flash chromatography (45% EtOAc in hexane) yielding 5-bromo-7,8-dihydrobenzofuro[4,5-d]thiazol-2-amine (0.45 g, 1.666 mmol). MS: ES+ 271.0 (M+1).

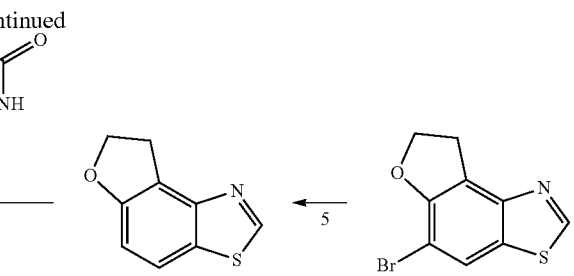

Step-4 5-bromo-7,8-dihydrobenzofuro[4,5-d]thiazole

To a stirred solution 5-bromo-7,8-dihydrobenzofuro[4,5-d]thiazol-2-amine (0.4 g, 1.481 mmol) in THF (4.0 ml) was added t-butyl nitrite (0.27 g, 2.666 mmol). The reaction mixture was stirred at 70° C. for 1 h before pouring into water (50 ml) and extracted with EtOAc (2×60 ml). The resulting crude material was purified by flash chromatography (4.5% EtOAc in hexane) yielding 5-bromo-7,8-dihydrobenzofuro[4,5-d]thiazole (0.17 g, 0.667 mmol). MS: ES+ 255.9 (M+1).

Step-5 7,8-dihydrobenzofuro[4,5-d]thiazole

To a stirred solution 5-bromo-7,8-dihydrobenzofuro[4,5-d]thiazole (0.13 g, 0.509 mmol) in DMF (6.0 ml) was added ammonium formate (0.15 g, 2.549 mmol). The reaction mixture was purged with $N_2$ gas for 15 min and tetrakis (0.05 g, 0.0509 mmol) was added. The reaction mixture was stirred at 80° C. for 2 h before pouring into water (40 ml) and extracted with EtOAc (2×40 ml). The resulting crude material was purified by flash chromatography (4.5% EtOAc in hexane) yielding 7,8-dihydrobenzofuro[4,5-d]thiazole (0.067 g, 0.378 mmol). MS: ES+ 178.1 (M+1).

Step-6 N-(5-(7,8-dihydrobenzofuro[4,5-d]thiazol-2-yl)pyridin-3-yl)acetamide To a stirred solution of 7,8-dihydrobenzofuro[4,5-d]thiazole (0.06 g, 0.338 mmol) in DMF (6.0 ml) were added $K_2CO_3$ (0.14 g, 1.016 mmol) and N-(5-bromopyridin-3-yl)acetamide (which was synthesized by following similar synthetic procedures as described in Example-4A, but using 5-bromopyridin-3-amine in step-1 instead of 3-bromopyridin-4-amine) (0.08 g, 0.373 mmol). The reaction mixture was purged with Ar before Cu(I)Br (0.019 g, 0.136 mmol), Pd(OAc)$_2$ (0.009 g, 0.041 mmol) and P (t-Bu)$_3$ (0.016 g, 0.081 mmol) were added. The reaction mixture was heated at 150° C. for 18 h before pouring into water (80 ml) and extracted with EtOAc (2×40 ml). The resulting crude material was purified by flash chromatography (78.2% EtOAc in hexane) yielding N-(5-(7,8-dihydrobenzofuro[4,5-d]thiazol-2-yl)pyridin-3-yl)acetamide (PST-201) (0.02 g, 0.064 mmol). MS: ES+ 312 (M+1); 1H NMR (400 MHz, DMSO-$d_6$) δ ppm: 10.46 (s, 1H), 8.85-8.91 (m, 2H), 8.74 (s, 1H), 7.91 (d, J=8.8 Hz, 1H), 7.04 (d, J=8.8 Hz, 1H), 4.71 (t, J=8.8 Hz, 2H), 3.57 (t, J=8.8 Hz, 2H), 2.13 (s, 3H).

Scheme-10

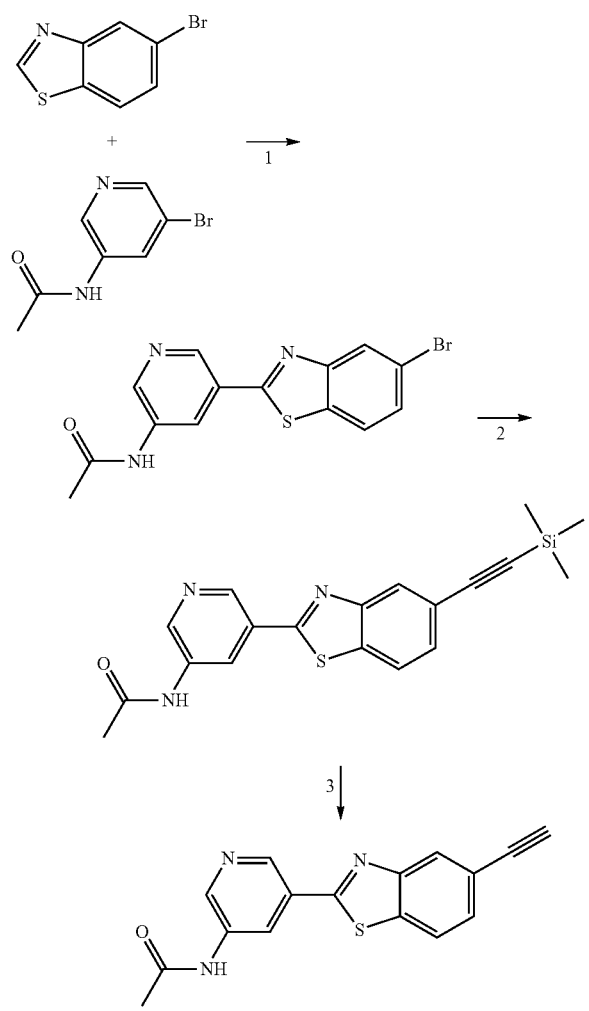

Example 10A

N-(5-(5-ethynylbenzo[d]thiazol-2-yl)pyridin-3-yl)acetamide (PST-147)

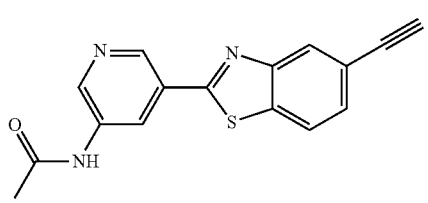 [SMILES: C#Cc1ccc2sc(-c3cncc(NC(C)=O)c3)nc2c1]

Step-1 N-(5-(5-bromobenzo[d]thiazol-2-yl)pyridin-3-yl)acetamide

To a stirred solution of 5-bromobenzothiazole (0.5 g, 2.335 mmol) in toluene (10 ml) were added $CS_2CO_3$ (1.9 g, 5.838 mmol) and N-(5-bromopyridin-3-yl)acetamide (which was synthesized by following similar synthetic procedures as described in Example-4A, but using 5-bromopyridin-3-amine in step-1 instead of 3-bromopyridin-4-amine) (0.499 g, 2.335 mmol). The reaction mixture was purged with before Cu(I)Br (0.067 g, 0.467 mmol), Pd(OAc)$_2$ (0.026 g, 0.117 mmol) and Xantphos (0.27 g, 0.467 mmol) were added. The reaction mixture was heated at 110° C. for 16 h before pouring into water (150 ml) and extracted with EtOAc (3×100 ml). The resulting crude material was purified by flash chromatography (8% MeOHc in MDC) yielding N-(5-(5-bromobenzo[d]thiazol-2-yl)pyridin-3-yl)acetamide (0.32 g, 0.922 mmol) MS: ES+ 348, 350 (M+1).

Step-2 N-(5-(5-(((trimethylsilyl)ethynyl)benzo[d]thiazol-2-yl)pyridin-3-yl)acetamide To a stirred solution of N-(5-(5-bromobenzo[d]thiazol-2-yl)pyridin-3-yl)acetamide (0.5 g, 1.441 mmol) in THF (12 ml) were added ethynyltrimethylsilane (0.424 g, 4.323 mmol), Cu(I)I (0.011 g, 0.057 mmol) and diisopropylamine (0.88 g, 8.646 mmol). The reaction mixture was purged with before Pd(dppf)Cl$_2$ (0.042 g, 0.058 mmol) was added. The reaction mixture was heated at 70° C. for 16 h, poured into water (100 ml) and extracted with EtOAc (2×100 ml). The resulting crude material was purified by flash chromatography (48% EtoAc in Hexane) yielding N-(5-(5-(((trimethylsilyl)ethynyl)benzo[d]thiazol-2-yl)pyridin-3-yl)acetamide (0.35 g, 0.967 mmol). MS: ES+ 366 (M+1).

Step-3 N-(5-(5-ethynylbenzo[d]thiazol-2-yl)pyridin-3-yl)acetamide

To a stirred solution of N-(5-(5-(((trimethylsilyl)ethynyl)benzo[d]thiazol-2-yl)pyridin-3-yl)acetamide (0.2 g, 0.547 mmol) in methanol (5 ml) was added $K_2CO_3$ (0.23 g, 1.641 mmol) and stirred for 2 h. The mixture was concentrated under reduced pressure, resuspended in water (15 ml) and extracted with EtOAc (2×20 ml), yielding N-(5-(5-ethynylbenzo[d]thiazol-2-yl)pyridin-3-yl)acetamide (0.08 g, 0.273 mmol). MS: ES+ 294.06 (M+1); 1H NMR (400 MHz, DMSO-d$_6$) δ ppm: 10.84 (s, 1H), 8.86-8.91 (m, 3H), 8.15-8.40 (m 2H), 7.58 (d, J=8.4 Hz, 1H), 4.35 (s, 1H), 2.14 (s, 3H)

Scheme-11

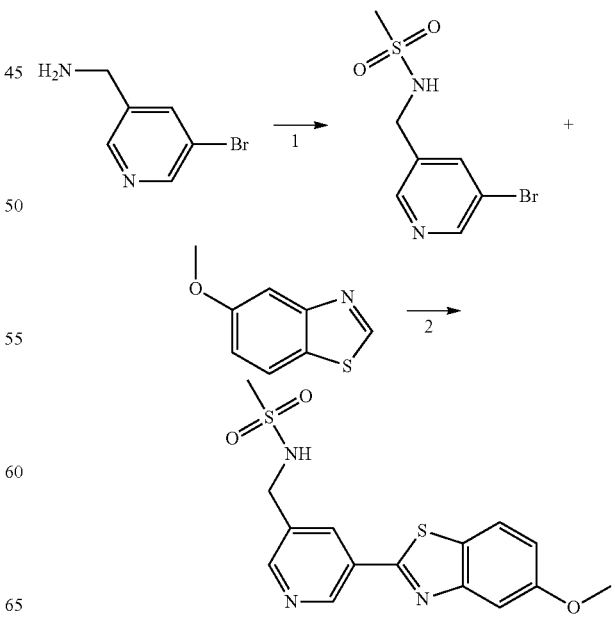

Example 11A

N-{[5-(5-methoxy-1,3-benzothiazol-2-yl)pyridin-3-yl]methyl}methanesulfonamide (PST-097)

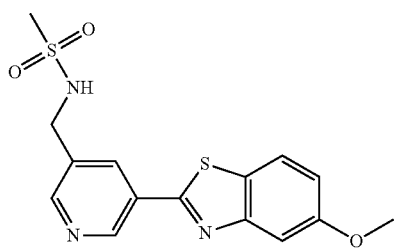 [SMILES: COc1ccc2sc(-c3cncc(CNS(C)(=O)=O)c3)nc2c1]

Step-1
N-((5-bromopyridin-3-yl)methyl)methanesulfonamide

To a stirred solution (5-bromopyridin-3-yl)methanamine (0.2 g, 1.069 mmol) in THF (5.0 ml) were added $K_2CO_3$ (0.3 g, 2.139 mmol) and mesyl chloride (0.2 g, 1.603 mmol) and stirred at ambient temperature for 2 h. The resulting reaction mixture was poured into saturated $NaHCO_3$ solution and extracted with EtOAc (2×20 ml) yielding N-((5-bromopyridin-3-yl)methyl)methanesulfonamide (0.4 g, 1.515 mmol) 3.251 min, MS: ES+ 264.8 (M+1).

Step-2 N-{[5-(5-methoxy-1,3-benzothiazol-2-yl)pyridin-3-yl]methyl}methanesulfonamide The title compound (PST-097) was synthesized following similar synthetic procedures as mentioned for Example-3A whilst using methyl N-((5-bromopyridin-3-yl)methyl)methanesulfonamide in step-1 instead of 3-bromo-4-chloropyridine.

MS: ES+ 249.9 (M+1); 1H NMR (400 MHz, DMSO-$d_6$) δ ppm: 9.23 (br s, 1H), 8.80 (br s, 1H), 8.43 (s, 1H), 8.08 (d, J=8.8 Hz, 1H), 7.79 (t, J=6.0 Hz, 1H), 7.69 (d, J=2.4 Hz, 1H), 7.16 (dd, J=8.8, 2.4 Hz, 1H), 4.36 (d, J=6.0 Hz, 2H), 3.88 (s, 3H), 2.99 (s, 3H).

Example 11B 5-methoxy-2-(6-ethylpyridazin-3-yl)benzo[d]thiazole (PST-1001)

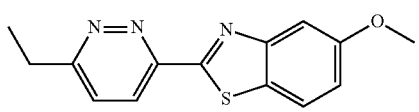 [SMILES: CCc1ccc(-c2nc3cc(OC)ccc3s2)nn1]

The title compound (PST-1001) can be synthesized following similar synthetic procedures as mentioned for Example-3A whilst using 3-bromo-6-ethylpyridazine in step-1 instead of 3-bromo-4-chloropyridine.

B. $IC_{50}$ Determination $IC_{50}$ values (in μM) against DYRK1A for the compounds of Example B are shown in Table 8 below. The methodology used to determine the $IC_{50}$ values was similar to that detailed above in Example A (see Table 5).

TABLE 8

| Compound Name | $IC_{50}$ value (μM) |
|---|---|
| PST-288 | 0.491 |
| PST-206 | 0.207 |
| PST-201 | 0.644 |
| PST-173 | 0.33 |
| PST-170 | 0.0437 |
| PST-169 | 0.281 |
| PST-166 | ND |
| PST-164 | 0.593 |
| PST-163 | 5.42 |
| PST-162 | 0.175 |
| PST-158 | 0.922 |
| PST-157 | 0.15 |
| PST-156 | 0.0938 |
| PST-155 | 0.0518 |
| PST-154 | 0.35 |
| PST-151 | 0.644 |
| PST-150 | ND |
| PST-148 | 0.171 |
| PST-147 | 0.487 |
| PST-141 | 0.637 |
| PST-134 | 0.789 |
| PST-131 | 0.351 |
| PST-129 | 3.86 |
| PST-128 | 0.808 |
| PST-122 | 0.413 |
| PST-120 | 0.534 |
| PST-110 | 0.658 |
| PST-098 | 0.0774 |
| PST-097 | 0.488 |
| PST-096 | 0.273 |
| PST-095 | 0.236 |
| PST-087 | 0.247 |
| PST-082 | ND |
| PST-077 | 0.337 |
| PST-076 | 0.904 |
| PST-075 | 0.306 |

ND = Not determined

EMBODIMENTS OF THE INVENTION INCLUDE

Embodiment 1

A compound of Formula (I'),

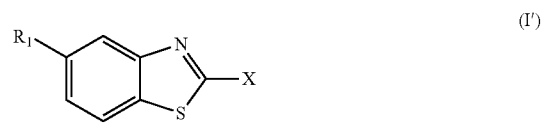

(I')

wherein
$R_1$ is selected from the group consisting of fluorine, an $OR_2$ group and a $CONHR_3$ group;
$R_2$ is hydrogen or a $C_{1-3}$ alkyl group;
$R_3$ is hydrogen or a $C_{1-3}$ alkyl group;
X is a five- or six-membered aromatic heterocyclic group, containing one or two nitrogen atoms in the ring, and which is substituted with a first substituent $R_4$, and optionally, a second substituent $R_5$, wherein $R_4$ and $R_5$, if present, are attached to a carbon atom in the heterocyclic group;
$R_4$ and $R_5$, which may be the same or different, are each a group represented by Formula (II),

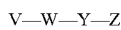

(II)

wherein
the covalent bonds V—W, W—Y, and Y—Z are single, double or triple bonds;

V represents C, N or F, if V is C, the C may be substituted by O, OH, F, $F_2$ or $F_3$, and if V is N, the N may be substituted by a $C_{1-3}$ alkyl group;

W represents C, N, O, S, or is absent, if W is C, the C may be substituted by O, OH, $CH_3$, F, $F_2$ or $F_3$, if W is N, the N may be substituted by a $C_{1-3}$ alkyl group and if W is S, the S is substituted by O or $(O)_2$, preferably $(O)_2$;

Y represents C or N, or is absent, if Y is C, the C may be substituted by O, OH, $CH_3$, F, $F_2$ or $F_3$;

Z represents C, N or is absent, if Z is C, the C may be substituted by O, OH or $NH_2$;

or W—Y—Z together form part of a 5- or 6-membered unsubstituted heterocyclic group, having at least one ring N atom and optionally also a further heteroatom in the ring selected from N and O;

or Y—Z together form part of a 5- or 6-membered aromatic heterocyclic group which contains 1 or 2 nitrogen atoms in the ring and is optionally substituted by one or two groups, which may be the same or different, selected from OH, $NH_2$, $NH(CO)CH_3$, $CH_2NH_2$, $CH_2NHC_{1-3}$ alkyl and $CH_2N(C_{1-3}$ alkyl$)_2$;

wherein if W, Y and Z are absent from $R_4$ and $R_5$ is also absent, V is not unsubstituted N or C;

wherein $R_5$, if present, comprises six or fewer non-hydrogen atoms;

or a pharmaceutically acceptable salt, hydrate, solvate or tautomer thereof,
but excluding the following compounds:

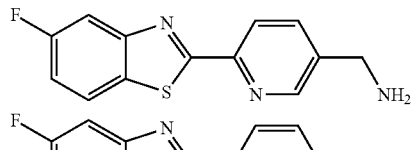
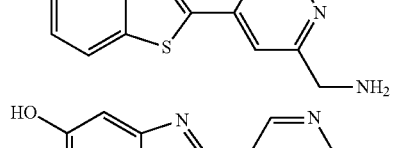
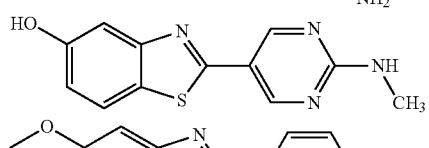
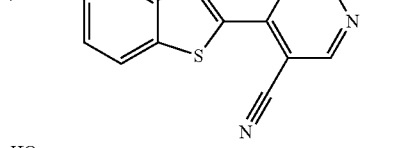
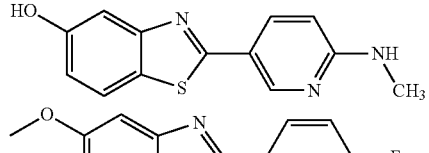
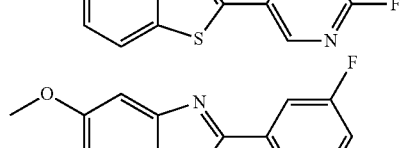
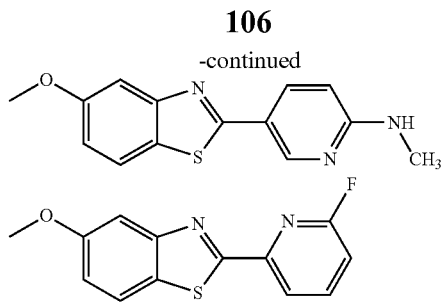

Embodiment 2

A compound as claimed in embodiment 1 of Formula (III)

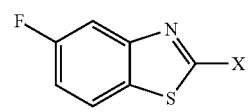

(III)

or Formula (IV)

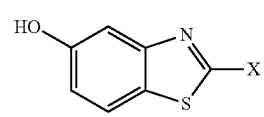

(IV)

or Formula (V)

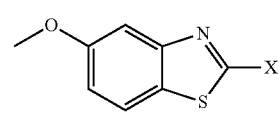

(V)

wherein X is as defined in claim 1.

Embodiment 3

A compound as claimed in embodiment 1 or embodiment 2 wherein X contains one nitrogen atom in the ring.

Embodiment 4

A compound as claimed in any one of embodiments 1 to 3 wherein X is a six-membered cyclic group.

Embodiment 5

A compound as claimed in embodiment 4 wherein the six-membered cyclic group has at least one nitrogen atom present in the meta-position.

Embodiment 6

A compound as claimed in any one of embodiments 1 to 5 wherein $R_4$ is selected from the substituents depicted in Table 1.

Embodiment 7

A compound as claimed in any one of embodiments 1 to 6 wherein $R_5$ is absent.

Embodiment 8

A compound as claimed in any one of embodiments 1 to 7 wherein $R_4$ has no more than 12 non-hydrogen atoms.

Embodiment 9

A compound as claimed in any one of embodiments 1 to 8, wherein if X is a six-membered group having a nitrogen atom present in the meta-position, then neither the $R_4$ substituent nor the $R_5$ substituent is present at the para-position.

Embodiment 10

A compound as claimed in any one of embodiments 1 to 9 wherein the $R_4$ substituent and if present the $R_5$ substituent, are present at the ortho- and/or meta-position, preferably the meta-position.

Embodiment 11

A compound as claimed in any of embodiments 1 to 10 wherein V represents unsubstituted C or N.

Embodiment 12

A compound as claimed in any of embodiments 1 to 11 wherein W represents unsubstituted C or C substituted by O, or S substituted by $(O)_2$.

Embodiment 13

A compound as claimed in any of embodiments 1 to 12 wherein Y represents unsubstituted N or C or C substituted by O or $CH_3$.

Embodiment 14

A composition comprising a compound as claimed in any one of embodiments 1 to 13 and a suitable carrier, diluent or excipient.

Embodiment 15

A compound or composition as claimed in any one of embodiments 1 to 14 for use in therapy.

Embodiment 16

A compound of formula (I') as defined in any one of embodiments 1 to 13 for use in the treatment or prevention of a neurodegenerative disorder.

Embodiment 17

A method of treating or preventing a neurodegenerative disorder in a subject comprising administering to said subject a therapeutically effective amount of a compound of formula (I') as defined in any one of embodiments 1 to 13.

Embodiment 18

Use of a compound of formula (I') as defined in any one of embodiments 1 to 13 in the manufacture of a medicament for the treatment or the prevention of a neurodegenerative disorder.

Embodiment 19

The compound for use of embodiment 16, the method of embodiment 17 or the use of embodiment 18 wherein the neurodegenerative disorder is Alzheimer's disease or Parkinson's disease.

Embodiment 20

The compound for use, the method or the use of embodiment 19 wherein the subject has Down Syndrome.

Embodiment 21

A compound of formula (I') as defined in any one of embodiments 1 to 13 for use in the treatment or prevention of diabetes mellitus.

Embodiment 22

A method of treating or preventing diabetes mellitus in a subject comprising administering to said subject a therapeutically effective amount of a compound of formula (I') as defined in any one of embodiments 1 to 13.

Embodiment 23

Use of a compound of formula (I') as defined in any one of embodiments 1 to 13 in the manufacture of a medicament for the treatment or the prevention of diabetes mellitus.

The invention claimed is:
1. A compound of Formula (I),

(I)

wherein
$R_1$ is selected from the group consisting of fluorine, an $OR_2$ group, a $CONHR_3$ group, $CH_2C(O)NHR_3$ and $-C\equiv CR_2$;
$R_2$ is hydrogen or a $C_{1-3}$ alkyl group;
$R_3$ is hydrogen or a $C_{1-3}$ alkyl group; and
$R_{1a}$ is H;
or
$R_1$ and $R_{1a}$ together form a 5- or 6-membered unsubstituted ring, optionally containing a heteroatom selected from N, O or S;
X is a five- or six-membered aromatic heterocyclic group, containing only one nitrogen atom in the ring, and which is substituted with a first substituent $R_4$, and optionally, a second substituent R$_5$, wherein R$_4$ and R$_5$, if present, are attached to a carbon atom in the heterocyclic group;

R$_4$ and R$_5$, which may be the same or different, are each a group represented by Formula (II),

V—W—Y—Z  (II)

wherein
the covalent bonds V—W, W—Y, and Y—Z are single, double or triple bonds;
V represents C, N or F, if V is C, the C may be substituted by O, OH, F, F$_2$ or F$_3$, and if V is N, the N may be substituted by a C$_{1-3}$ alkyl group;
W represents C, N, O, S, or is absent, if W is C, the C may be substituted by O, OH, CH$_3$, F, F$_2$ or F$_3$, if W is N, the N may be substituted by a C$_{1-3}$ alkyl group and if W is S, the S is substituted by O or (O)$_2$, preferably (O)$_2$;
or
W represents a 5- or 6-membered carbocyclic group, or a 5- or 6-membered heterocyclic group having at least one ring N atom and optionally also a further heteroatom in the ring selected from N, O and S, wherein W may optionally be substituted by one or two halogen atoms;
Y represents C, N, O, S or is absent, if Y is C, the C may be substituted by O, OH, CH$_3$, F, F$_2$ or F$_3$;
or
Y represents a 5- or 6-membered carbocyclic group, or a 5- or 6-membered heterocyclic group containing 1 or 2 nitrogen atoms in the ring, and optionally substituted by one or two groups, which may be the same or different, selected from OH, NH$_2$, NH(CO)CH$_3$, CH$_2$NH$_2$, CH$_2$NHC$_{1-3}$ alkyl and CH$_2$N(C$_{1-3}$ alkyl)$_2$;
Z represents C, N, O or is absent, if Z is C, the C may be substituted by O, OH, NH$_2$, or CH$_3$, if Z is N, the N may be substituted by C(O)C$_{1-4}$alkyl, S(O)$_2$C$_{1-4}$alkyl or CHR$^{4a}$COOH, wherein R$^{4a}$ is selected from H, CH$_3$, CH(CH$_3$)$_2$, CH$_2$OH or CH(OH)CH$_3$, if Z is O, the O may be substituted by C$_{1-4}$alkyl;
wherein if W, Y and Z are absent from R$_4$ and R$_5$ is also absent, V is not unsubstituted N or C;
wherein R$_5$, if present, comprises six or fewer non-hydrogen atoms;
or a pharmaceutically acceptable salt, hydrate, solvate or tautomer thereof,
but excluding the following compounds:

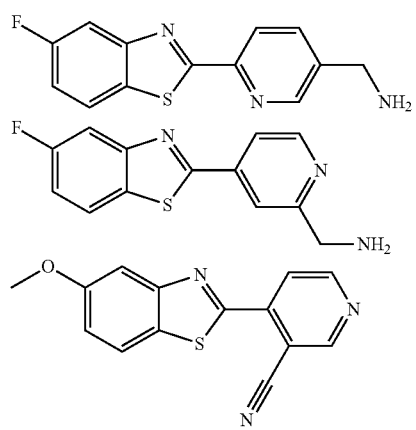

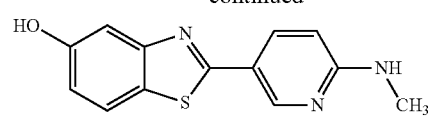
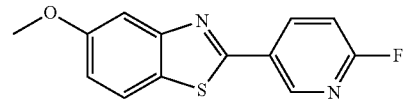
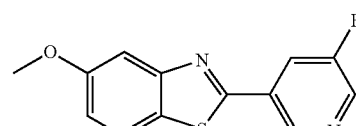
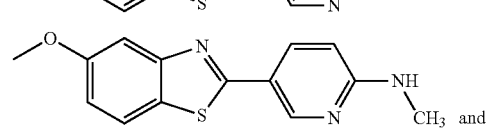
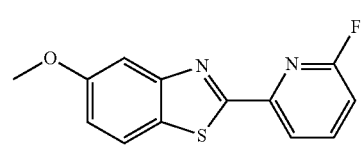

2. The compound as claimed in claim 1 of Formula (III)

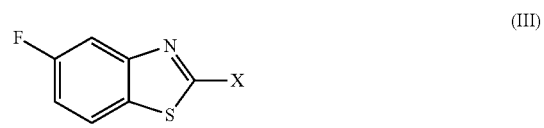

or Formula (IV)

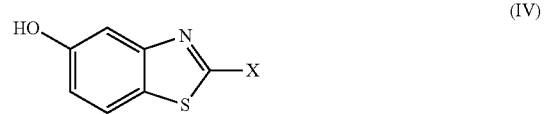

or Formula (V)

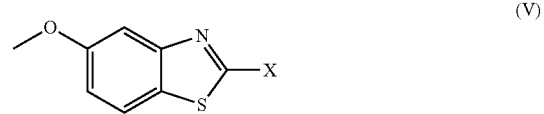

wherein X is as defined in claim 1.

3. The compound as claimed in claim 1 wherein X is a six-membered cyclic group.

4. The compound as claimed in claim 3 wherein the six-membered cyclic group has at least one nitrogen atom present in the meta-position.

5. The compound as claimed in claim 1 wherein R$_4$ is selected from the substituents depicted in Table 1, TABLE 1
| | |
|---|---|
| 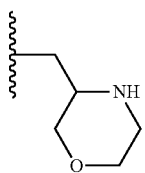 [SMILES: *CC1COCCN1] | 1) |
| 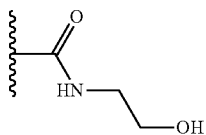 [SMILES: *C(=O)NCCO] | 2) |
| 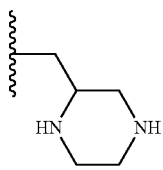 [SMILES: *CC1CNCCN1] | 3) |
| 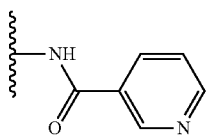 [SMILES: *NC(=O)c1cccnc1] | 4) |
| 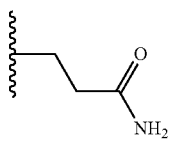 | 5) |
| 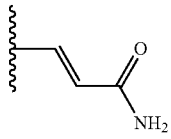 | 6) |
| 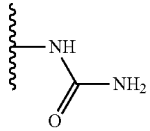 [SMILES: *NC(N)=O] | 7) |
| 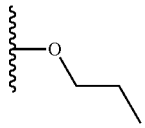 | 8) |
| 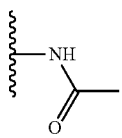 [SMILES: *NC(C)=O] | 9) |
| 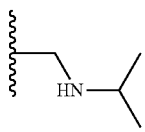 [SMILES: *CNC(C)C] | 10) |
TABLE 1-continued
| | |
|---|---|
| 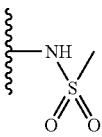 | 11) |
| 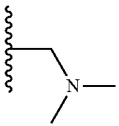 [SMILES: *CN(C)C] | 12) |
| 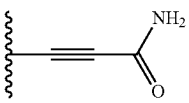 [SMILES: *C#CC(N)=O] | 13) |
| 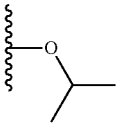 | 14) |
|  | 15) |
| 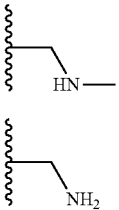 | 16) |
| 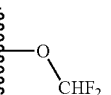 | 17) |
| 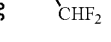 | 18) |
| 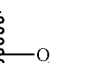 | 19) |
| 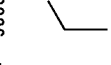 | 20) |
| 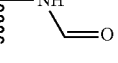 | 21) |
|  | 22) |
| 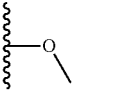 | 23) |
| | 24) |

TABLE 1-continued
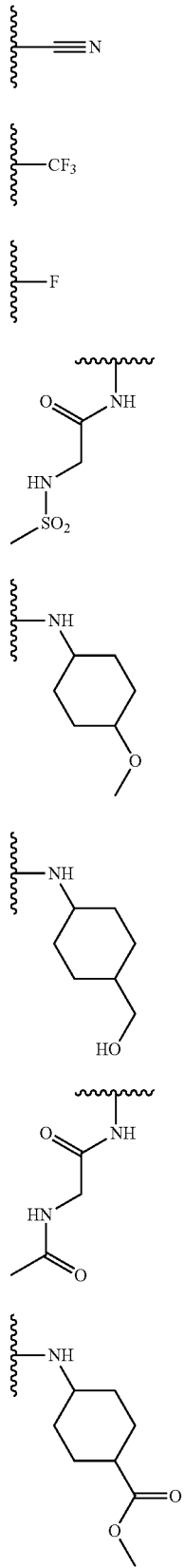
25)
26)
27)
28)
29)
30)
31)
32)
TABLE 1-continued
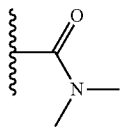 [SMILES: *C(=O)N(C)C] 33)
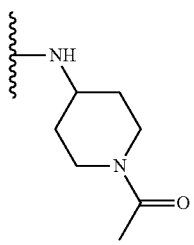 [SMILES: *NC1CCN(C(C)=O)CC1] 34)
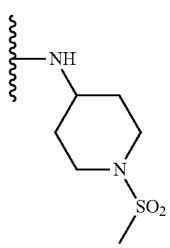 [SMILES: *NC1CCN(S(C)(=O)=O)CC1] 35)
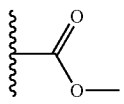 36)
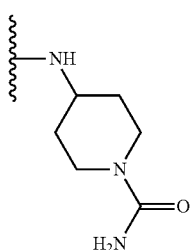 37)
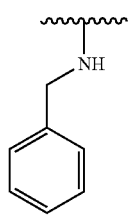 [SMILES: *NCc1ccccc1] 38)
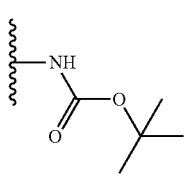 [SMILES: *NC(=O)OC(C)(C)C] 39)
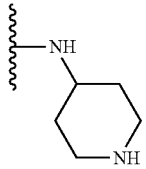 [SMILES: *NC1CCNCC1] 40)

TABLE 1-continued

41) 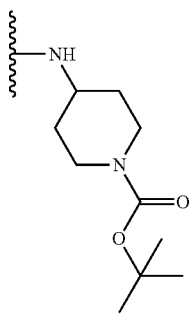 [SMILES: *NC1CCN(C(=O)OC(C)(C)C)CC1]

42) 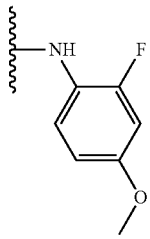 [SMILES: *Nc1ccc(OC)cc1F]

43) 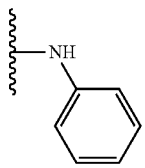 [SMILES: *Nc1ccccc1]

44) 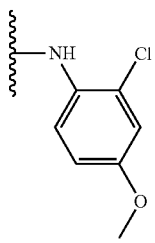 [SMILES: *Nc1ccc(OC)cc1Cl]

45) 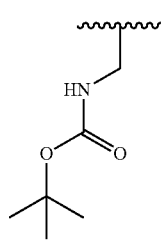 [SMILES: *CNC(=O)OC(C)(C)C]

46) 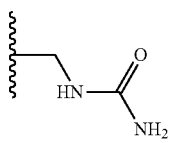

47) 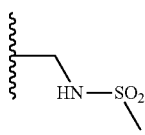

TABLE 1-continued

48) 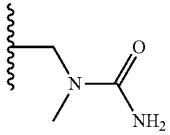

49) 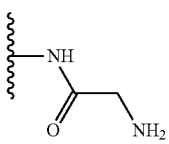

50) 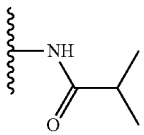 [SMILES: *NC(=O)C(C)C]

51) 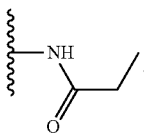

6. The compound as claimed in claim 1 wherein $R_5$ is absent.

7. The compound as claimed in claim 1 wherein $R_4$ has no more than 14 non-hydrogen atoms.

8. The compound as claimed in claim 1, wherein if X is a six-membered group having a nitrogen atom present in the meta-position, then neither the $R_4$ substituent nor the $R_5$ substituent is present at the para-position.

9. The compound as claimed in claim 1 wherein the $R_4$ substituent and if present the $R_5$ substituent, are present at the ortho- and/or meta-position, preferably the meta-position.

10. The compound as claimed in claim 1 wherein V represents unsubstituted C or N.

11. The compound as claimed in claim 1 wherein W represents unsubstituted C, unsubstituted N, C substituted by O, S substituted by $(O)_2$, a 6-membered carbocyclic group, or a 6-membered heterocyclic group having one ring N atom.

12. The compound as claimed in claim 1 wherein Y represents unsubstituted N or C or C substituted by O or $CH_3$.

13. A composition comprising a compound as claimed in claim 1 and a suitable carrier, diluent or excipient.

14. A method of treating a disease or disorder associated with abnormal activity of DYRK1A and/or DYRK1B in a subject comprising administering to said subject a therapeutically effective amount of a compound of formula (I) as defined in claim 1, wherein the disease or disorder is Alzheimer's disease or Parkinson's disease.

15. The method of claim 14 wherein the subject has Down Syndrome.

* * * * *